United States Patent
Walsh et al.

(10) Patent No.: US 7,460,958 B2
(45) Date of Patent: Dec. 2, 2008

(54) COMPUTER-IMPLEMENTED SYSTEM AND METHOD FOR ANALYZING MIXTURES OF GASES

(75) Inventors: Alicia Marie Walsh, Wilmington, DE (US); Kenneth S. Dahl, Wilmington, DE (US); Charles E. Miller, Spring, TX (US); Patricia A. Morris, Montchanin, DE (US); Michael Joseph Piovoso, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 184 days.

(21) Appl. No.: 11/242,749

(22) Filed: Oct. 4, 2005

(65) Prior Publication Data

US 2006/0155486 A1 Jul. 13, 2006

Related U.S. Application Data

(60) Provisional application No. 60/617,222, filed on Oct. 7, 2004.

(51) Int. Cl.
*G01N 31/00* (2006.01)
(52) U.S. Cl. .......................................... 702/24
(58) Field of Classification Search .................. 702/22, 702/23, 24, 29, 30, 104, 116; 73/23.2, 23.35, 73/1.02, 1.03, 1.06, 23.21; 422/105–109
See application file for complete search history.

(56) References Cited

U.S. PATENT DOCUMENTS

| | | | |
|---|---|---|---|
| 4,007,435 A | 2/1977 | Tien | |
| 4,151,503 A | 4/1979 | Cermak et al. | |
| 4,225,842 A | 9/1980 | Schlesselman et al. | |
| 4,234,542 A | 11/1980 | Romine | |
| 4,387,359 A | 6/1983 | Tien et al. | |
| 4,457,161 A | 7/1984 | Iwanaga | |
| 4,535,316 A | 8/1985 | Wertheimer et al. | |
| 4,542,640 A | 9/1985 | Clifford | |
| 4,770,760 A | 9/1988 | Noda et al. | |
| 5,239,483 A | 8/1993 | Weir | |
| 5,402,665 A * | 4/1995 | Hart et al. | 73/1.06 |
| 5,426,934 A | 6/1995 | Hunt | |

(Continued)

FOREIGN PATENT DOCUMENTS

| | | |
|---|---|---|
| DE | 44 08 361 A1 | 9/1995 |
| DE | 44 08 504 A1 | 9/1995 |
| WO | WO 00/00808 A2 | 1/2000 |

OTHER PUBLICATIONS

H. Meixner et. al., Chemosensors for Motor Management Systems of the Future, Fresenius J. Anal. Chem., 1994, pp. 536-541, vol. 348.

(Continued)

*Primary Examiner*—Edward Raymond
*Assistant Examiner*—Mohamed Charioui

(57) ABSTRACT

A computer-implemented system and method for converting the resistances of an array of metal oxide sensors into constituents and concentrations of a multi-component gas provided around the sensor array. The method includes preprocessing the resistances of the sensor array; selecting a model that calculates the constituents and concentrations of the multi-component gas based on the preprocessed resistances; and post-processing the constituents and concentrations of the multi-component gas generated by the selected model to provide the actual constituents and concentrations of the multi-component gas.

36 Claims, 47 Drawing Sheets

U.S. PATENT DOCUMENTS

| | | | |
|---|---|---|---|
| 5,488,858 | A | 2/1996 | Achleitner |
| 5,554,273 | A * | 9/1996 | Demmin et al. ............ 205/785 |
| 5,630,920 | A | 5/1997 | Friese et al. |
| 5,731,510 | A | 3/1998 | Jones et al. |
| 5,736,028 | A | 4/1998 | Hjortsberg et al. |
| 5,776,601 | A | 7/1998 | Fournier et al. |
| 5,832,411 | A | 11/1998 | Schatzmann |
| 5,879,526 | A | 3/1999 | Dietz |
| 5,952,555 | A | 9/1999 | Mobius |
| 6,012,282 | A | 1/2000 | Kato et al. |
| 6,082,176 | A | 7/2000 | Kondo et al. |
| 6,084,418 | A | 7/2000 | Takami et al. |
| 6,085,576 | A | 7/2000 | Sunshine et al. |
| 6,109,095 | A | 8/2000 | Addiego |
| 6,170,318 | B1 | 1/2001 | Lewis |
| 6,235,243 | B1 | 5/2001 | Fleischer |
| 6,849,239 | B2 | 2/2005 | Morris |
| 6,890,715 | B1 | 5/2005 | Lewis |
| 6,960,476 | B2 | 11/2005 | Morris |
| 7,231,290 | B2 | 6/2007 | Steichen |
| 2001/0013026 | A1 | 8/2001 | Shaffer |
| 2002/0017467 | A1 | 2/2002 | Ando |
| 2002/0050161 | A1 * | 5/2002 | Warburton ............. 73/23.2 |
| 2003/0216855 | A1 | 11/2003 | Liang |
| 2005/0063873 | A1 | 3/2005 | Morris |
| 2007/0202012 | A1 | 8/2007 | Steichen |

OTHER PUBLICATIONS

Corrado Di Natale et. al., Performance Evaluation of an SNO2-Based Sensor Array for the Quantitative Measurement of Mixtures of H2S and NO2, Sensors and Actuators B., 1994, pp. 217-224, vol. 20.

Brent T. Marquis et. al., A Semiconducting Metal Oxide Sensor Array for the Detection of NOX and NH3, Sensors and Actuators B, 2001, pp. 100-110, vol. 77.

S.W. Moore et. al., A Modified Multilayer Perceptron Model for Gas Mixture Analysis, Sensors and Actuators B, 1993, pp. 344-348.

G. Huyberechts et. al., Simultaneous Quantification of Carbon Monoxide and Methane in Humid Air Using a Sensor Array and an Artifical Neural Network, Sensors and Actuators B, 1997, pp. 123-130, vol. 45.

Kazimierz Brudzewski et. al., Gas Analysis System Composed of a Solid-State Sensor Array and Hybrid Neural Network Structure, Sensors and Actuators B, 1999, pp. 38-46, vol. 55.

P.C. Jurs et. al., Computational Methods for the Analysis of Chemical Sensor Array Data From Volatile Analytes, Chem. Rev., 2000, pp. 2649-2678, vol. 100.

Keith J. Albert et. al., Cross-Reactive Chemical Sensor Arrays, Chem. Rev., 2000, pp. 2595-2626, vol. 100.

H. Meixner et. al., Metal Oxide Sensors, Sensors and Actuators B, 1996, pp. 198-202, vol. 33.

J. Getino et. al., Integrated Sensor Array for Gas Analysis in Combustion Atmospheres, Sensors and Actuators B, 1996, pp. 128-133, vol. 33.

Corrado Di Natale et. al., Study of the Effect of the Sensor Operating Temperature on SN02-Based Sensor Array Performance, Sensors and Actuators B, 1995, pp. 187-191, vol. 23.

Gardner et. al., Solid State Chemical and Biochemical Sensors, Advances in Science and Technology, 1999, pp. 335-345, vol. 26.

Antonio Pardo et. al., Nonliner Inverse Dynamic Models of Gas Sensing Systems Based on Chemical Sensor Arrays for Quantitative Measurements, IEEE Transactions on Instrumentation and Measurement, 1998, pp. 644-651, vol. 47.

B.S. Hoffheins et. al., Performance of Simpllfled Chemical Sensor Arrays in a Neural Network-Based Analytical Instrument, Analusis, 1992, pp. 201-207, vol. 20.

H. E. Endres et al; A thin film $SnO_2$ sensor system for simultaneous detection of CO and $NO_2$ with neural signal evaluation; Sensors and Actuators, B 35-36 (1996) 353-357; Elsevier; New York.

PCT International Search Report and Written Opinion in Appl. No. PCT/US2005/036265, Jan. 3, 2007.

* cited by examiner

Figure 17B
Uncorrected sensor element response
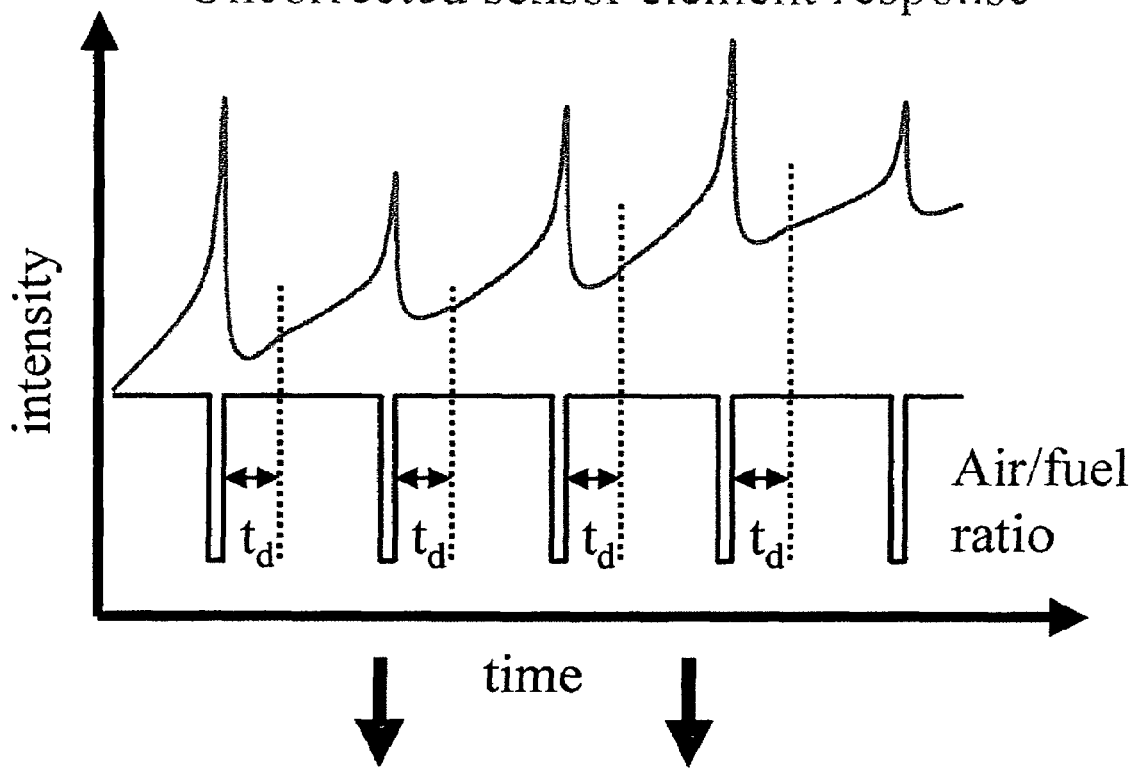
*Corrected* sensor element response
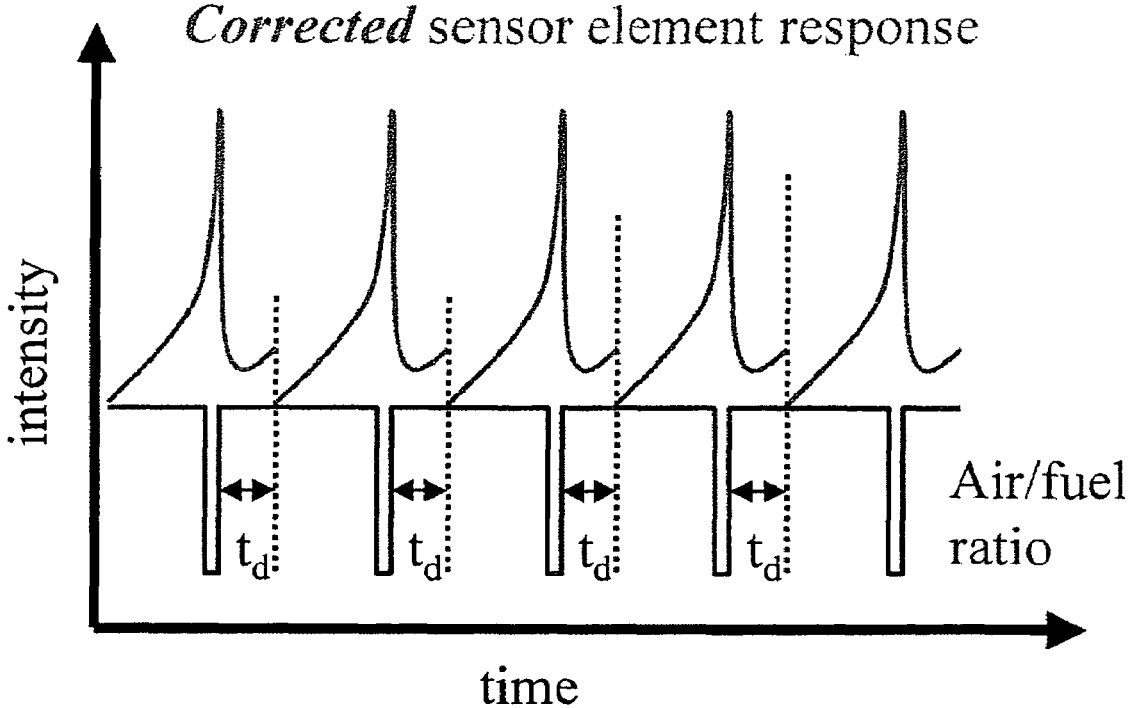

Figure 26
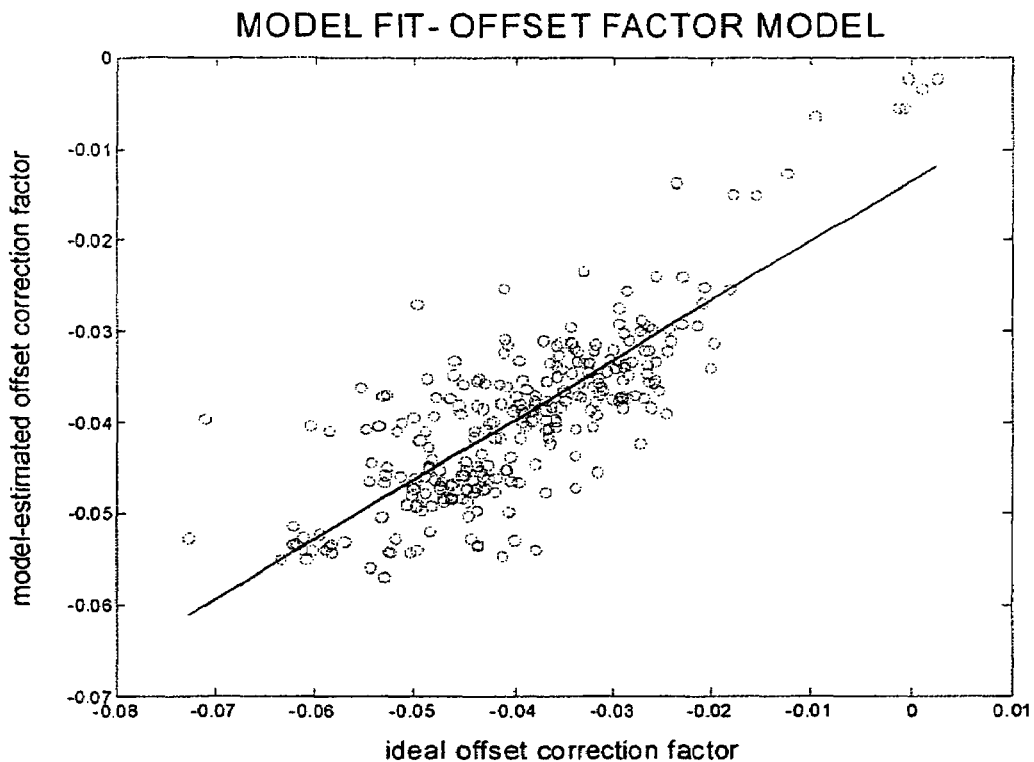
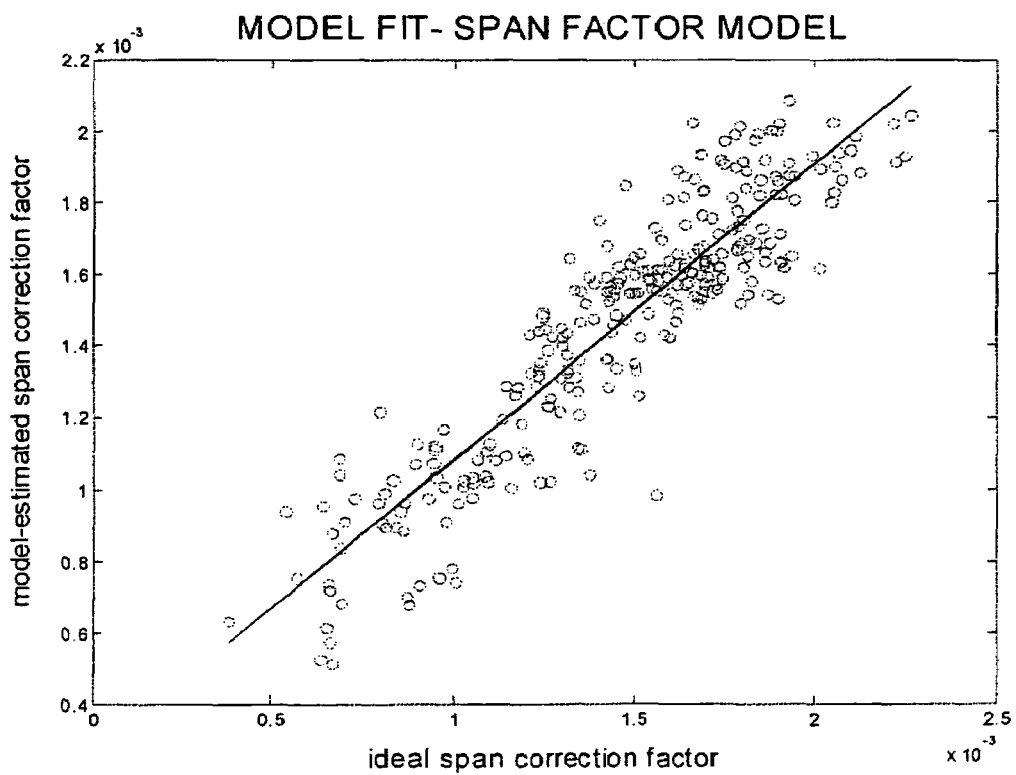

Figure 27
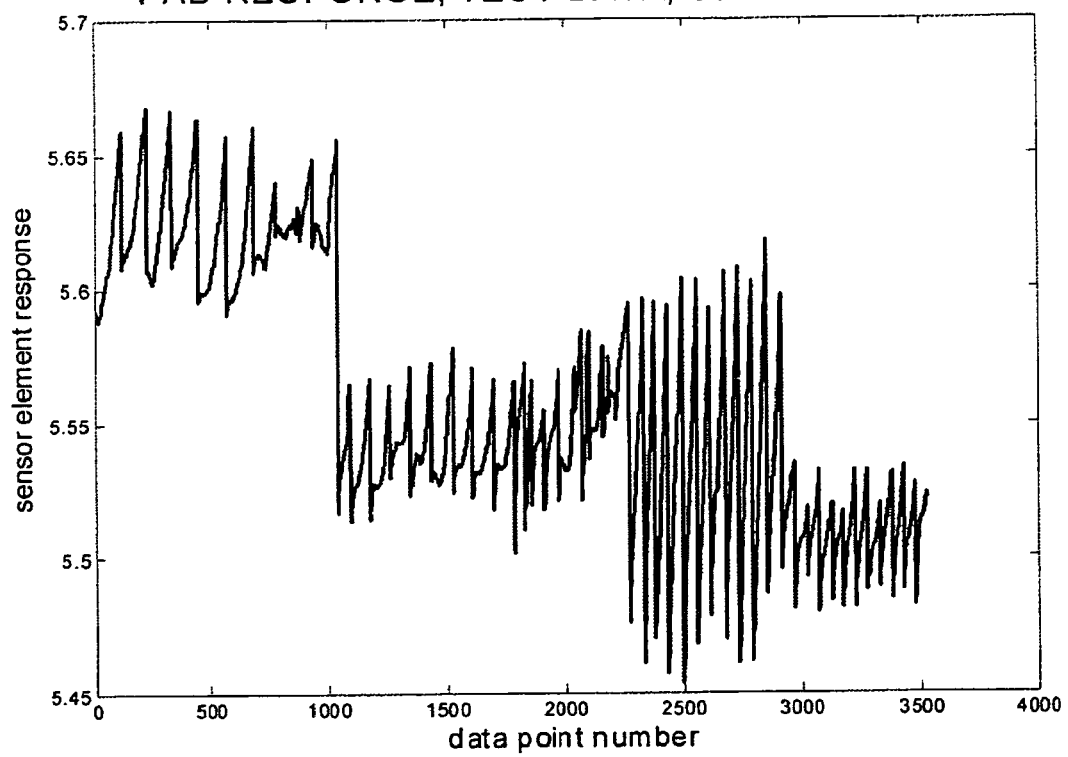
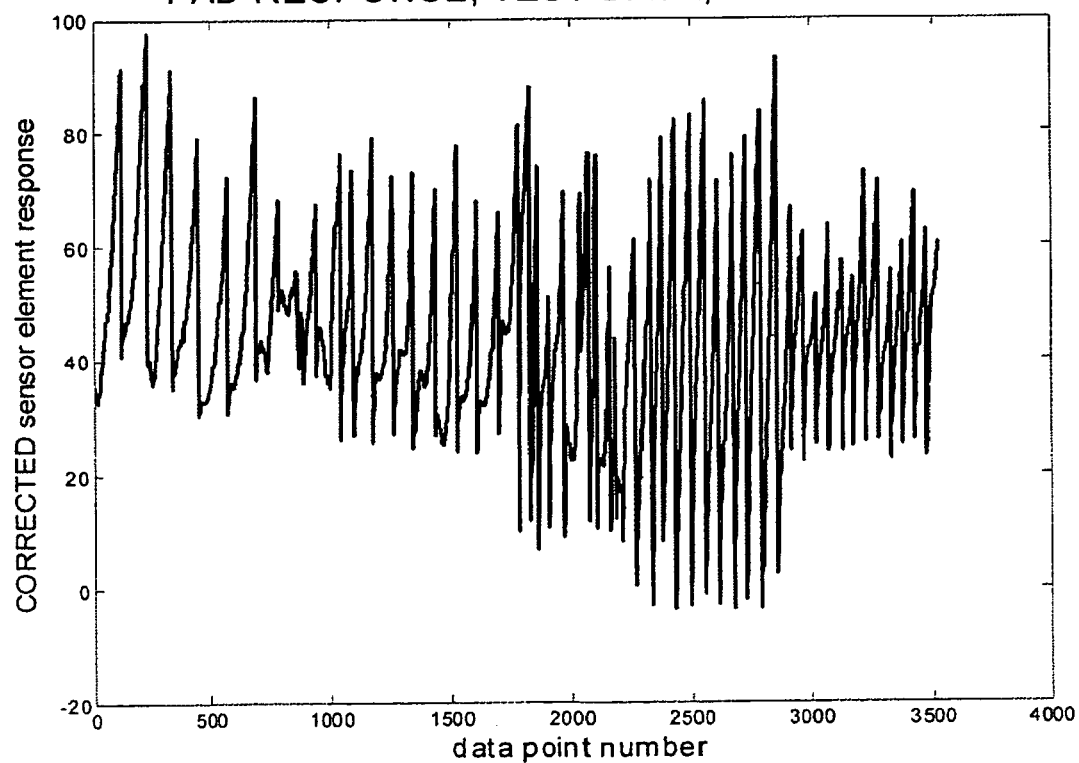

COMPUTER-IMPLEMENTED SYSTEM AND METHOD FOR ANALYZING MIXTURES OF GASES

CLAIM FOR PRIORITY

The present application claims priority benefit of U.S. Provisional Patent Application Ser. No. 60/617,222, filed Oct. 7, 2004, which is incorporated in its entirety as a part hereof for all purposes.

REFERENCE TO RELATED APPLICATIONS

The present application relates to U.S. patent application Ser. No. 10/117,472, filed Apr. 5, 2002, which is a continuation-in-part of U.S. patent application Ser. No. 09/977,791, filed Oct. 15, 2001, which claimed the benefit of U.S. Provisional Application Ser. No. 60/240,619, filed Oct. 16, 2000, and U.S. Provisional Application Ser. No. 60/246,946, filed Nov. 9, 2000, the disclosures of the above-referenced applications being incorporated by reference herein in their entireties.

BACKGROUND

A. Technical Field

The present invention relates generally to a system and method for sensing and analyzing certain gases, including $NO_x$, hydrocarbons, carbon monoxide and oxygen in a multi-component gas system using chemical sensors and chemical sensor arrays.

B. Description of the Related Art

The use of chemical sensing devices to detect certain gases is known. Many attempts have been made to find a material with selectivity and sensitivity for a specific gas. For example, U.S. Pat. No. 4,535,316 discloses a resistive sensor for measuring oxygen. See also H. Meixner et al., *Sensors and Actuators B: Chem.*, vol. 33, pp. 198-202 (1996). It is apparent that different materials must be used for each gas to be detected. However, when a gas is part of a multi-component system, using one material to detect a specific gas is difficult because of the cross-sensitivities of the material to the various component gases of the mixture.

One example of a multi-component gaseous system is a combustion gas emission, which can include oxygen, carbon monoxide, nitrogen oxides, hydrocarbons, $CO_2$, $H_2S$, sulfur dioxide, hydrogen, water vapor, halogens and ammonia. See H. Meixner et al., *Fresenius' J. Anal. Chem.*, vol. 348, pp. 536-541 (1994). In many combustion processes, there is a need to determine whether the gas emissions meet requirements established by federal and state air quality regulations in various jurisdictions. Several types of gas sensors have been developed to address this need. See U.S. Pat. No. 5,630,920, which discloses an electrochemical oxygen sensor; U.S. Pat. No. 4,770,760, which discloses a sensor for detecting oxygen and oxides of nitrogen; and U.S. Pat. No. 4,535,316, which discloses a resistive sensor for measuring oxygen. It would be advantageous to be able to simultaneously analyze two or more components of a mixture such as a combustion gas emission, to calculate concentration for example, in terms only of data generated by direct contact of the gases with a sensor and without having to separate any of the gases in the mixture. Prior art methods do not currently meet this need.

Numerous sensors have been disclosed to detect gases evolving from foods and from other relatively low temperature applications. See K. Albert et al., *Chem. Rev.*, vol. 200, pp. 2595-2626 (2000). Arrays of several undoped and doped tin oxide sensors have also been disclosed for use in detecting various combustion gases up to 450° C. See C. DiNatale et al., *Sensors and Actuators B: Chem.*, vol. 20, pp. 217-224 (1994); J. Getino et al., *Sensors and Actuators B: Chem.*, vol. 33, pp. 128-133 (1996); and C. DiNatale et al., *Sensors and Actuators B: Chem.*, vol. 23, pp. 187-191 (1995). However, at higher temperatures and in the highly corrosive environment in which one would use chemical sensors to monitor combustion gases, operating temperature can alter or impair the performance of the sensor array. That being the case, high temperature environments require the use of materials that are both chemically and thermally stable and that maintain measurable responses to the gases of interest. The effect of the operating temperature on the response of tin oxide-based sensor arrays was studied up to 450° C. See C. DiNatale et al., *Sensors and Actuators B: Chem.*, vol. 23, pp. 187-191 (1995). However, materials in addition to those previously known in the art are still needed to be able to provide a system and method capable of directly monitoring the gas emissions of multi-component gas systems at higher temperatures, such as would be encountered in the operation of combustion gas systems. Detecting circuits and analytical devices are also needed for such chemical sensors to provide a system and method capable of processing the chemical sensor outputs and providing useful information in determining the components and constituents of the monitored multi-component gas system.

Addressing this need would permit the use of a chemical sensor to measure combustion emissions, such as automobile exhausts, and determine whether those emissions meet functional and mandated requirements. In addition, it has surprisingly been found that the system and method of this invention that are useful for analyzing high temperature gases, such as automotive emissions, may be employed with equal effect in analyzing low temperature gases.

SUMMARY OF VARIOUS EMBODIMENTS OF THE INVENTION

The present invention satisfies these needs by providing a computer-implemented system and method for sensing and analyzing certain gases, including $NO_x$, hydrocarbons, carbon monoxide and oxygen in a multi-component gas system using novel chemical sensors and chemical sensor arrays, detecting circuits, and analytical devices.

Additional advantages of the invention will be set forth in part in the description which follows, and in part will be learned from the description, or may be learned by practice of the invention. The advantages of the invention will be realized and attained by means of the elements and combinations particularly pointed out in the appended claims, and equivalents thereof. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention. In the drawings:

FIG. 17B is a graph illustrating the execution of a adaptive offset and span correction method on sensor response in a GDI engine;

FIG. 26 provides graphs showing the fit of the factor regression models for the offset and span correction factors for the sensing element in the example;

FIG. 27 are graphs showing a comparison of sensor element responses in the test set data before adaptive correction (top) and after adaptive correction (bottom) using correction factors estimated from the correction factor models shown in FIG. 26 (bottom);

FIGS. 38A-38E are a series of graphs showing an analysis that applies the residual ratio (RR) quality factor and the contributions to it from individual sensor elements to diagnose that one sensor element in an array of twelve had malfunctioned, wherein FIG. 38A is a graph of the residual ratio (RR) quality factor during two in-engine tests, FIG. 38B is a bar graph of the contributions to the residual during the first in-engine test at time 1495, FIG. 38C is a bar graph of the contributions to the residual during the second in-engine test at time 2736, FIG. 38D is a bar graph of the contributions to the residual during the second in-engine test at time 5941, and FIG. 38E is a graph of the resistances for three sensor elements during the two in-engine tests.

DETAILED DESCRIPTION

Reference will now be made in detail to the present embodiments of the invention, examples of which are illustrated in the accompanying drawings. Wherever possible, the same reference numbers will be used throughout the drawings to refer to the same or like parts.

Figure 1:
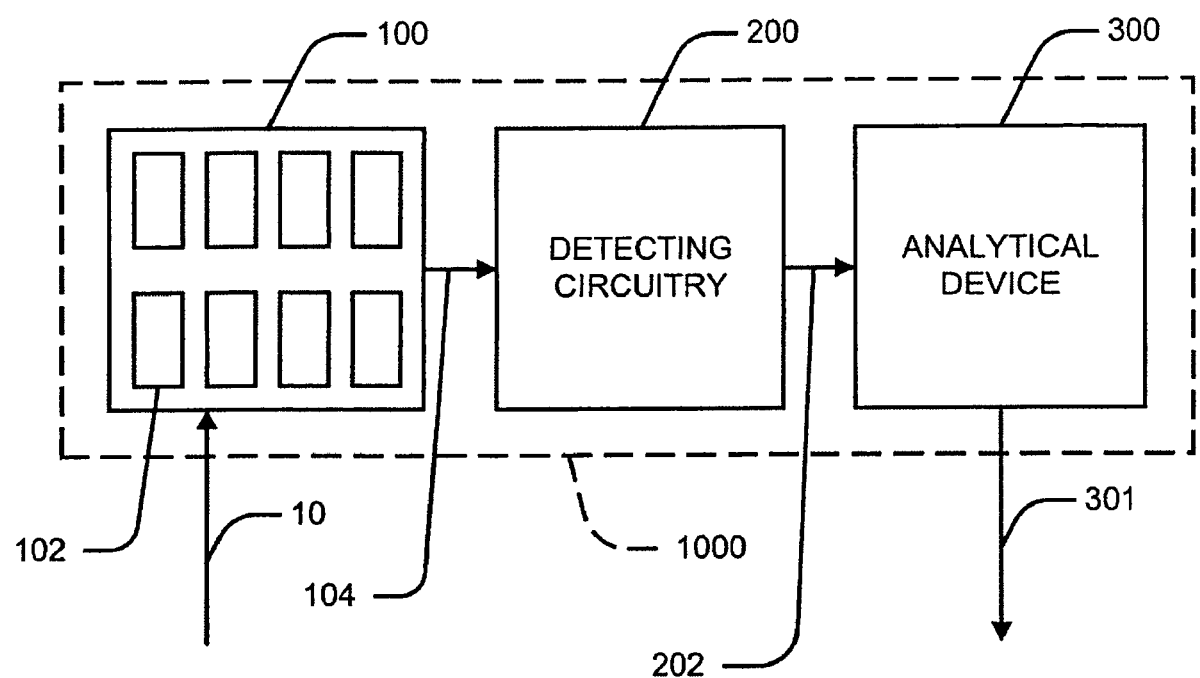
FIG. 1 is a schematic diagram showing a system of the present invention, the system including a chemical sensor array, detecting circuitry, and an analytical device.

The present invention is broadly drawn to a system and method for directly sensing gases in multi-component gas systems under ambient to high temperature conditions, as generally shown by reference numeral 1000 in FIG. 1. The system is also useful for simultaneously and directly measuring the concentration of at least one gas in a multi-component gas system at temperature ranges from about ambient to about 1000° C. By "directly sensing" is meant that the array will be present in the gas stream and the response will be a function of the concentrations of the gases themselves, and that the gases do not have to be physically separated in the gas stream in order to be detected. Direct sensing may also refer to what is known in the art as indirect sensing, soft sensing, or inferential sensing.

The system and method can be used to detect and measure the concentrations of combustion gases, such as oxygen, carbon monoxide, nitrogen oxides, hydrocarbons, such as butane, $CO_2$, $H_2S$, sulfur dioxide, halogens, and ammonia at lower and higher temperatures in automobile emissions. In this application, the system can be used at the high temperatures found in automotive emission systems, typically in the range of from about 450° C. to about 1000° C. In addition there are a variety of other combustion processes for which this system could be applied, including diesel engines and home heating. These applications make use of the detection of gases such as nitrogen oxides, carbon monoxide, hydrocarbons and oxygen at the ppm to percent levels, typically in a highly corrosive environment. This system and method is also useful for detecting gases in other gas systems such as those found in manufacturing processes, waste streams, and environmental monitoring.

The system described herein utilizes an array of sensing materials to detect the components of the gas system. By "array" is meant at least two different materials that are spatially separated. The materials used are chemo-electro-active materials. As used herein, "chemo-electro-active materials" are materials that have an electrical response to certain gases. Some metal oxide semiconducting materials, mixtures thereof, or mixtures of metal oxide semiconductors with other inorganic compounds are chemo-electro-active and are particularly useful in the system and method of the present invention. The various chemo-electro-active materials used herein exhibit changes to different degrees in the presence of different gases. As a result, an array of appropriately chosen chemo-electro-active materials can be used to determine the presence of certain gases in a gas stream. These chemo-electro-active materials can be used at temperatures from ambient to about 1000° C. Preferably, the mole percentages of the major components of these materials differ.

The measurement of the gas concentrations using chemo-electro-active materials can be based on the change in AC impedances of the materials in response to the concentration of adsorbed gas molecules at their surfaces, or can be based on, for example, capacitance, voltage, current, resistance or temperature differential. By using an array of these materials, a pattern of the respective responses can be used to simultaneously and directly measure the concentration of at least one gas in a multi-component gas system at temperature ranges from about ambient to about 1000° C.

As seen in FIG. 1, the system 1000 provides a chemical sensor or chemical sensor array comprising a substrate 100 and one or more chemo-electro-active materials 102 chosen to detect the presence and/or concentration of one or more gases in a multi-component gas stream 10. The system 1000 further comprises detecting circuitry 200 to detect changes in the AC impedances of the materials 104 in response to the concentration of adsorbed gas molecules at their surfaces. The system 1000 further comprises an analytical device 300 to measure or analyze the detected gases 202 such that the presence of the gases are identified and their concentrations are measured and outputted 301. Analytical device 300 may include instrumentation or equipment that is capable of performing chemometrics, neural networks or other pattern recognition and/or predictive techniques. In some embodiments, the analytical device 300 may be incorporated into the AC impedance determining circuitry 200. The system 1000 may further comprise a housing for substrate 100 and array of chemo-electro-active materials 102, the detecting circuitry 200, and analytical device 300, although analytical device 300 may be separate from the housing. The chemical sensors 100, detecting circuitry 200, and analytical device 300 will each be described in detail below.

A. The Chemical Sensors

The chemical sensor array 100 of the present invention is disclosed in U.S. patent application Ser. Nos. 10/117,472 and 09/977,791, referenced above and incorporated herein by reference. The array 100 may be situated within the gas mixture 10, and more particularly within the source of the gas mixture 10, if desired. Alternatively, the array 100 may reside in a chamber to which the gas mixture 10 is directed from its source at another location. When gas is directed to a chamber in which an array is located, the gas mixture may be inserted in and removed from the chamber by piping, conduits, or any other suitable gas transmission equipment.

A response may be obtained upon exposure of the gas-sensing materials to the multi-component gas mixture, and the response will be a function of the concentrations of one or more of the analyte gases themselves in the gas mixture. The sensor materials will be exposed substantially simultaneously to each of the analyte gases, and an analyte gas does not have to be physically separated from the multi-component gas mixture for an analysis of the mixture and/or one or more components thereof to be conducted. This invention can be used, for example, to detect and/or measure the concentrations of combustion gases, such as oxygen, carbon monoxide, nitrogen oxides, hydrocarbons such as butane, $CO_2$, $H_2S$, sulfur dioxide, halogens, hydrogen, water vapor and ammonia, at variable temperatures in automobile emissions.

The system and method are therefore useful at the higher temperatures found in automotive emission systems, typically in the range of from about 400° C. to about 1000° C. In addition there are a variety of other combustion processes for which this invention could be applied, including diesel engines and home heating. These applications require the detection of gases such as nitrogen oxides, ammonia, carbon monoxide, hydrocarbons and oxygen at the ppm to percent levels, typically in a highly corrosive environment. The apparatus and method are also useful for detecting gases in other gas systems such as those found in manufacturing processes, waste streams, and environmental monitoring; or in systems in which odor detection is important and/or that are at lower temperature, such as in the medical, agricultural or food and beverage industries.

Figure 2:
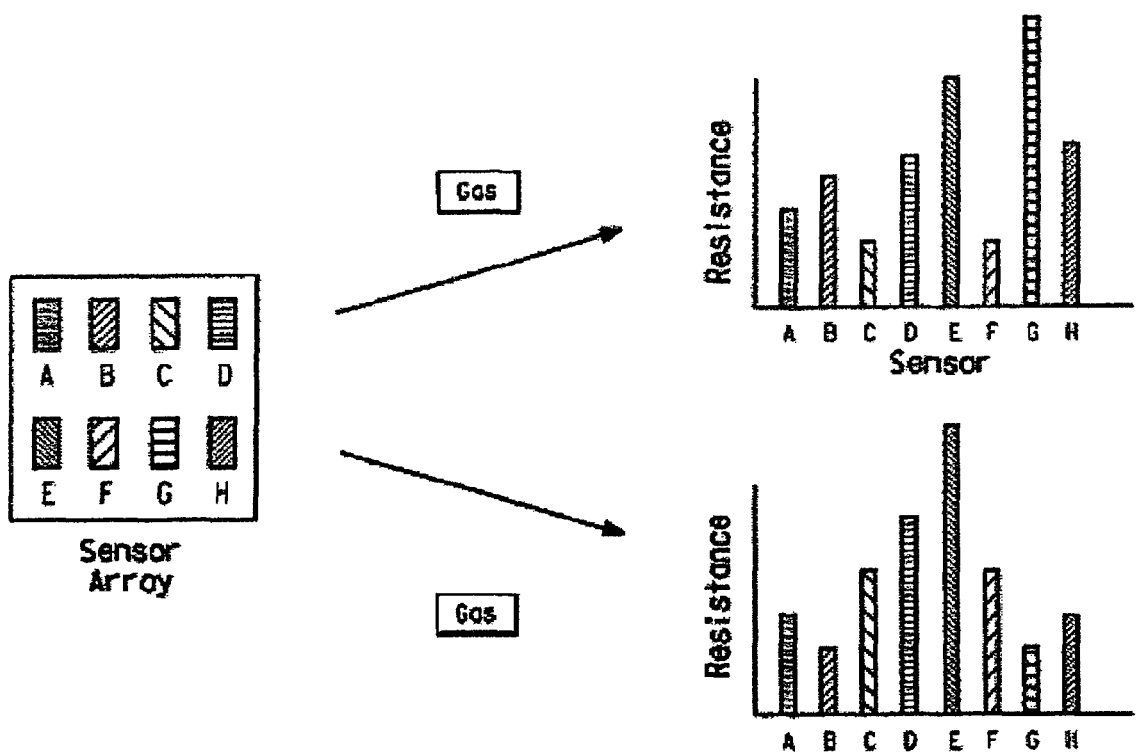
FIG. 2 depicts the sensor array concept of the system shown in FIG. 1.

The system and method utilize an array of sensing materials to analyze a gas mixture and/or the components thereof to, for example, detect the presence of and/or calculate the concentration of one or more individual analyte gas components in the system. By "array" is meant at least two different materials that are spatially separated, as shown for example in FIGS. 1 and 2. The array may contain, for example, 3, 4, 5, 6, 8, 10 or 12 gas-sensing materials, or other greater or lesser numbers as desired. It is preferred that there be provided at least one sensor material for each of the analyte gases or classes of analyte of gases in the mixture to be analyzed. It may be desirable to provide more than one sensor material that is responsive to an individual gas component and/or a particular subgroup in the mixture. For example, a group of at least 2, 3, 4, 5, 6, 7, 8, 9, 10, 11 or 12 sensors could be used to detect the presence of, and/or calculate the concentration of, one or more individual component gases and/or one or more subgroups of gases in the mixture. Different groups of sensors could be used for this purpose, which may or may not have members in common. A subgroup of gases that is an analyte as the subgroup may or may not contain as a member an individual gas that is itself an analyte. Preferably, the mole percentages of the major components of each gas-sensing material differ from that of each of the others.

The sensing materials used are chemo-electro-active materials. A "chemo-electro-active material" is a material that has an electrical response to at least one individual gas in a mixture. Some metal oxide semiconducting materials, mixtures thereof, or mixtures of metal oxide semiconductors with other inorganic compounds are chemo-electro-active, and are particularly useful in this invention. Each of the various chemo-electro-active materials used herein preferably exhibits an electrically detectable response of a different kind and/or extent, upon exposure to the mixture and/or an analyte gas, than each of the other chemo-electro-active materials. As a result, an array of appropriately chosen chemo-electro-active materials can be used to analyze a multi-component gas mixture, such as by interacting with an analyte gas, sensing an analyte gas, or determining the presence and/or concentration of one or more analyte gases in a mixture, despite the presence therein of interfering gases that are not of interest.

The system and method are useful for detecting those gases that are expected to be present in a gas stream. For example, in a combustion process, gases that are expected to be present include oxygen, nitrogen oxides (such as NO, $NO_2$, $N_2O$ or $N_2O_4$), carbon monoxide, hydrocarbons (such as $C_nH_{2n+2}$, and the same may be saturated or unsaturated, or be optionally substituted with hetero atoms; and cyclic and aromatic analogs thereof), ammonia or hydrogen sulfide, sulfur dioxide, $CO_2$, or methanol. Other gases of interest may include alcohol vapors, solvent vapors, hydrogen, water vapor, and those deriving from saturated and unsaturated hydrocarbons, ethers, ketones, aldehydes, carbonyls, biomolecules and microorganisms. The component of a multi-component gas mixture that is an analyte of interest may be an individual gas such as carbon monoxide; may be a subgroup of some but not all of the gases contained in the mixture, such as the nitrogen oxides ($NO_x$); or may be a combination of one or more individual gases and one or more subgroups. When a subgroup of gases is an analyte, a chemo-electro-active material will respond to the collective concentration within a multi-component gas mixture of the members of the subgroup together.

Obtaining information related to the compositional content of a gas mixture using these sensor materials, such as measurement of gas concentrations, can be based on a change in an electrical property, such as AC impedance, of at least one, but preferably each and all, of the materials upon exposure of the materials to a mixture containing one or more analyte gases. Analysis of a gas mixture can also be performed in terms of extent of change in other electrical properties of the sensor materials, such as capacitance, voltage, current or AC or DC resistance. Change in DC resistance may be determined, for example, by measuring change in temperature at constant voltage provided other heating or cooling sources are constant. The change in one of these illustrative properties of a sensor material is a function of the partial pressure of an analyte gas within the gas mixture, which in turn determines the concentration at which the molecules of the analyte gases become adsorbed on the surface of a sensor material, thus affecting the electrical response characteristics of that material. By using an array of chemo-electro-active materials, a pattern of the respective responses exhibited by the materials upon exposure to a mixture containing one or more analyte gases can be used to simultaneously and directly detect the presence of, and/or measure the concentration of, at least one gas in a multi-component gas system. The invention, in turn, can be used to determine the composition of the gas system. The concept is illustrated schematically in FIGS. 1 and 2, and is exemplified below.

To illustrate, consider the theoretical example below of the exposure of a sensor material to a mixture containing an analyte gas. Where a response is obtained, the event is depicted as positive (+), and where no response is obtained, the event is depicted as negative (−). Material 1 responds to Gas 1 and Gas 2, but shows no response to Gas 3. Material 2 responds to Gas 1 and Gas 3, but shows no response to Gas 2, and Material 3 responds to Gas 2 and Gas 3, but shows no response to Gas 1.

|       | Material 1 | Material 2 | Material 3 |
|-------|------------|------------|------------|
| Gas 1 | +          | +          | −          |
| Gas 2 | +          | −          | +          |
| Gas 3 | −          | +          | +          |

Therefore, if an array consisting of Materials 1, 2, and 3 gives the following response to an unknown gas,

|             | Material 1 | Material 2 | Material 3 |
|-------------|------------|------------|------------|
| Unknown Gas | +          | −          | +          | then the unknown gas would be identified as Gas 2. The response of each sensor material would be a function of the partial pressure within the mixture of, and thus the concentration of, an analyte gas or the collective concentration of a subgroup of analyte gases; and the response could be quantified or recorded as a processible value, such as a numerical value. In such case, the values of one or more responses can be used to generate quantitative information about the concentration within the mixture of one or more analyte gases.

The chemo-electro-active material can be of any type, but especially useful are semiconducting metal oxides such as ZnO, $TiO_2$, $WO_3$, and $SnO_2$. These particular materials are advantageous due to their chemical and thermal stability. The chemo-electro-active material can be a mixture of two or more semiconducting materials, or a mixture of a semiconducting material with an inorganic material, or combinations thereof. The semiconducting materials of interest can be deposited on a suitable solid substrate that is an insulator such as, but not limited to, alumina or silica and is stable under the conditions of the multi-component gas mixture. The array then takes the form of the sensor materials as deposited on the substrate. Other suitable sensor materials include single crystal or polycrystalline semiconductors of the bulk or thin film type, amorphous semiconducting materials, and semiconductor materials that are not composed of metal oxides.

The chemo-electro-active materials used as sensor materials in this invention may, for example, be metal oxides of the formula $M^1O_x$, $M^1_aM^2_bO_x$, or $M^1_aM^2_bM^3_cO_x$; or mixtures thereof, wherein $M^1$, $M^2$ and $M^3$ are metals that form stable oxides when fired in the presence of oxygen above 500° C.; $M^1$ is selected from Periodic Groups 2-15 and the lanthanide group; $M^2$ and $M^3$ are independently selected from Periodic Groups 1-15 and the lanthanide group, but $M^2$ and $M^3$ are not the same in $M^1_aM^2_bM^3_cO_x$; a, b, and c are each independently in the range of about 0.0005 to about 1; and x is a number sufficient so that the oxygen present balances the charges of the other elements in the compound.

The metal oxides that contain more than one metal do not have to be a compound or solid solution, but can be a mixture of discrete metal oxides. They may exhibit composition gradients, and can be crystalline or amorphous. Suitable metal oxides are those that: (1) when at a temperature of about 400° C. or above, have a resistivity of about 1 to about $10^6$ ohm-cm, preferably about 1 to about $10^5$ ohm-cm, and more preferably about 10 to about $10^4$ ohm-cm; (2) show a chemo/electro response to at least one gas of interest; and (3) are stable and have mechanical integrity, that is are able to adhere to the substrate and not degrade at the operating temperature. The metal oxides may also contain minor or trace amounts of hydration and elements present in the precursor materials.

In certain preferred embodiments, the metal oxide materials may include those in which: $M^1$ is selected from the group consisting of Ce, Co, Cu, Fe, Ga, Nb, Ni, Pr, Ru, Sn, Ti, Tm, W, Yb, Zn, and Zr; and/or $M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same in $M^1_aM^2_bM^3_cO_x$.

In certain other preferred embodiments, the metal oxide materials may include those in which:

$M^1O_x$ is $Ce_aO_x$, $CoO_x$, $CuO_x$, $FeO_x$, $GaO_x$, $NbO_x$, $NiO_x$, $PrO_x$, $RuO_x$, $SnO_x$, $Ta_aO_x$, $TiO_x$, $TmO_x$, $WO_x$, $YbO_x$, $ZnO_x$, $ZrO_x$, $SnO_x$ with Ag additive, $ZnO_x$ with Ag additive, $TiO_x$ with Pt additive, $ZnO_x$ with frit additive, $NiO_x$ with frit additive, $SnO_x$ with frit additive, or $WO_x$ with frit additive; and/or $M^1_aM^2_bO_x$ is $Al_aCr_bO_x$, $Al_aFe_bO_x$, $Al_aMg_bO_x$, $Al_aNi_bO_x$, $Al_aTi_bO_x$, $Al_aV_bO_x$, $Ba_aCu_bO_x$, $Ba_aSn_bO_x$, $Ba_aZn_bO_x$, $Bi_aRu_bO_x$, $Bi_aSn_bO_x$, $Bi_aZn_bO_x$, $Ca_aSb_bO_x$, $Ca_aZn_bO_x$, $Cd_aSn_bO_x$, $Cd_aZn_bO_x$, $Ce_aFe_bO_x$, $Ce_aNb_bO_x$, $Ce_aTi_bO_x$, $Ce_aV_bO_x$, $Co_aCu_bO_x$, $Co_aGe_bO_x$, $Co_aLa_bO_x$, $Co_aMg_bO_x$, $Co_aNb_bO_x$, $Co_aPb_bO_x$, $Co_aSn_bO_x$, $Co_aV_bO_x$, $Co_aW_bO_x$, $Co_aZn_bO_x$, $Cr_aCu_bO_x$, $Cr_aLa_bO_x$, $Cr_aMn_bO_x$, $Cr_aNi_bO_x$, $Cr_aSi_bO_x$, $Cr_aTi_bO_x$, $Cr_aY_bO_x$, $Cr_aZn_bO_x$, $Cu_aFe_bO_x$, $Cu_aGa_bO_x$, $Cu_aLa_bO_x$, $Cu_aNa_bO_x$, $Cu_aNi_bO_x$, $Cu_aPb_bO_x$, $Cu_aSn_bO_x$, $Cu_aSr_bO_x$, $Cu_aTi_bO_x$, $Cu_aZn_bO_x$, $Cu_aZr_bO_x$, $Fe_aGa_bO_x$, $Fe_aLa_bO_x$, $Fe_aMo_bO_x$, $Fe_aNb_bO_x$, $Fe_aNi_bO_x$, $Fe_aSn_bO_x$, $Fe_aTi_bO_x$, $Fe_aW_bO_x$, $Fe_aZn_bO_x$, $Fe_aZr_bO_x$, $Ga_aLa_bO_x$, $Ga_aSn_bO_x$, $Ge_aNb_bO_x$, $Ge_aTi_bO_x$, $In_aSn_bO_x$, $K_aNb_bO_x$, $Mn_aNb_bO_x$, $Mn_aSn_bO_x$, $Mn_aTi_bO_x$, $Mn_aYb_bO_x$, $Mn_aZn_bO_x$, $Mo_aPb_bO_x$, $Mo_aRb_bO_x$, $Mo_aSn_bO_x$, $Mo_aTi_bO_x$, $Mo_aZn_bO_x$, $Nb_aNi_bO_x$, $Nb_aNi_bO_x$, $Nb_aSr_bO_x$, $Nb_aTi_bO_x$, $Nb_aW_bO_x$, $Nb_aZr_bO_x$, $Ni_aSi_bO_x$, $Ni_aSn_bO_x$, $Ni_aY_bO_x$, $Ni_aZn_bO_x$, $Ni_aZr_bO_x$, $Pb_aSn_bO_x$, $Pb_aZn_bO_x$, $Rb_aW_bO_x$, $Ru_aSn_bO_x$, $Ru_aW_bO_x$, $Ru_aZn_bO_x$, $Sb_aSn_bO_x$, $Sb_aZn_bO_x$, $Sc_aZr_bO_x$, $Si_aSn_bO_x$, $Si_aTi_bO_x$, $Si_aW_bO_x$, $Si_aZn_bO_x$, $Sn_aTa_bO_x$, $Sn_aTi_bO_x$, $Sn_aW_bO_x$, $Sn_aZn_bO_x$, $Sn_aZr_bO_x$, $Sr_aTi_bO_x$, $Ta_aTi_bO_x$, $Ta_aZn_bO_x$, $Ta_aZr_bO_x$, $Ti_aV_bO_x$, $Ti_aW_bO_x$, $Ti_aZn_bO_x$, $Ti_aZr_bO_x$, $V_aZn_bO_x$, $V_aZr_bO_x$, $W_aZn_bO_x$, $W_aZr_bO_x$, $Y_aZr_bO_x$, $Zn_aZr_bO_x$, $Al_aNi_bO_x$ with frit additive, $Cr_aTi_bO_x$ with frit additive, $Fe_aLa_bO_x$ with frit additive, $Fe_aNi_bO_x$ with frit additive, $Fe_aTi_bO_x$ with frit additive, $Nb_aTi_bO_x$ with frit additive, $Nb_aW_bO_x$ with frit additive, $Ni_aZn_bO_x$ with frit additive, $Ni_aZr_bO_x$ with frit additive, $Sb_aSn_bO_x$ with frit additive, $Ta_aTi_bO_x$ with frit additive, or $Ti_aZn_bO_x$ with frit additive; and/or $M^1_aM^2_bM^3_cO_x$ is $Al_aMg_bZn_cO_x$, $Al_aSi_bV_cO_x$, $Ba_aCu_bTi_cO_x$, $Ca_aCe_bZr_cO_x$, $Co_aNi_bTi_cO_x$, $Co_aNi_bZr_cO_x$, $Co_aPb_bSn_cO_x$, $Co_aPb_bZn_cO_x$, $Cr_aSr_bTi_cO_x$, $Cu_aFe_bMn_cO_x$, $Cu_aLa_bSr_cO_x$, $Fe_aNb_bTi_cO_x$, $Fe_aPb_bZn_cO_x$, $Fe_aSr_bTi_cO_x$, $Fe_aTa_bTi_cO_x$, $Fe_aW_bZr_cO_x$, $Ga_aTi_bZn_cO_x$, $La_aMn_bNa_cO_x$, $La_aMn_bSr_cO_x$, $Mn_aSr_bTi_cO_x$, $Mo_aPb_bZn_cO_x$, $Nb_aSr_bTi_cO_x$, $Nb_aSr_bW_cO_x$, $Nb_aTi_bZn_cO_x$, $Ni_aSr_bTi_cO_x$, $Sn_aW_bZn_cO_x$, $Sr_aTi_bV_cO_x$, $Sr_aTi_bZn_cO_x$, or $Ti_aW_bZr_cO_x$.

In certain other preferred embodiments, the metal oxide materials may include those that are in an array of first and second chemo-electro-active materials, wherein the chemo-electro-active materials are selected from the pairings in the group consisting of (i) the first material is $M^1O_x$, and the second material is $M^1_aM^2_bO_x$;

(ii) the first material is $M^1O_x$, and the second material is $M^1_aM^2_bM^3_cO_x$;

(iii) the first material is $M^1_aM^2_bO_x$, and the second material is $M^1_aM^2_bM^3_cO_x$;

(iv) the first material is a first $M^1_{Ox}$, and the second material is a second $M^1_{Ox}$;

(v) the first material is a first $M^1_aM^2_bO_x$, and the second material is a second $M^1_aM^2_bO_x$; and (vi) the first material is a first $M^1_aM^2_bM^3_cO_x$, and the second material is a second $M^1_aM^2_bM^3_cO_x$;

wherein $M^1$ is selected from the group consisting of Ce, Co, Cu, Fe, Ga, Nb, Ni, Pr, Ru, Sn, Ti, Tm, W, Yb, Zn, and Zr; $M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same in $M^1_aM^2_bM^3_cO_x$; a, b and c are each independently about 0.0005 to about 1; and and x is a number sufficient so that the oxygen present balances the charges of the other elements in the compound.

The sensor materials may optionally contain one or more additives to promote adhesion to a substrate, or that alter the conductance, resistance or selectivity of the sensor material. Examples of additives to promote adhesion are frits, which are finely ground glass, or finely ground inorganic minerals that are transformed into glass or enamel on heating. Illustrative frits include those designated as F2834, F3876, F2967, KH770, KH710 and KH375, available from DuPont iTechnologies. These may be used in amounts of up to 30 volume percent of the composition from which the sensor material is made. Examples of additives to alter the conductance, resistance, or selectivity include Ag, Au, or Pt, as well as frits.

If desired, the sensor materials may also contain additives that, for example, catalyze the oxidation of a gas of interest or promote the selectivity for a particular analyte gas; or contain one or more dopants that convert an n semiconductor to a p semiconductor, or vice versa. These additives may be used in amounts of up to 30 weight percent of the composition from which the sensor material is made. Any frits or other additives used need not be uniformly or homogeneously distributed throughout the sensor material as fabricated, but may be localized on or near a particular surface thereof as desired. Each chemo-electro-active material may, if desired, be covered with a porous dielectric overlayer. A suitable overlayer is QM44 from DuPont iTechologies.

Any method of depositing the chemo-electro-active material to a substrate is suitable. One technique used for deposition is applying a semiconducting material on an alumina substrate on which electrodes are screen-printed. The semiconducting material can be deposited on top of electrodes by hand painting semiconducting materials onto the substrate, nanopipetting materials into wells, thin film deposition, or thick film printing techniques. Most techniques are followed by a final firing to sinter the semiconducting materials.

Figure 3:
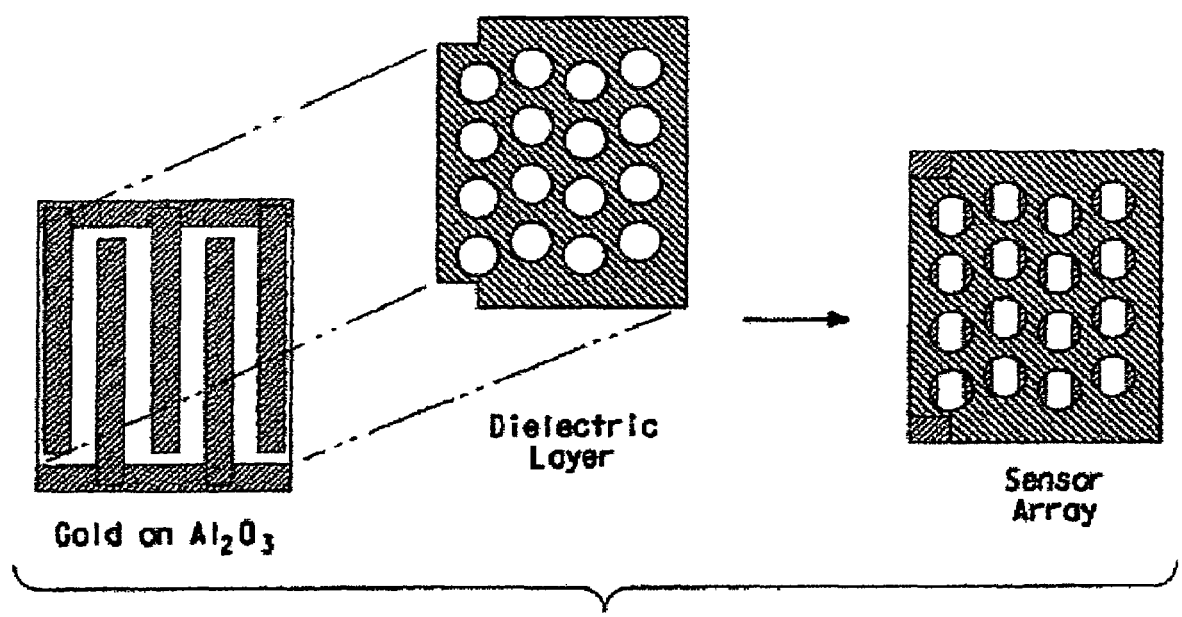
FIG. 3 is a schematic diagram of the pattern of interdigitated electrodes overlaid with the dielectric overlayer, forming sixteen blank wells of the chemical sensor array of the system shown in FIG. 1.
Figure 4A:
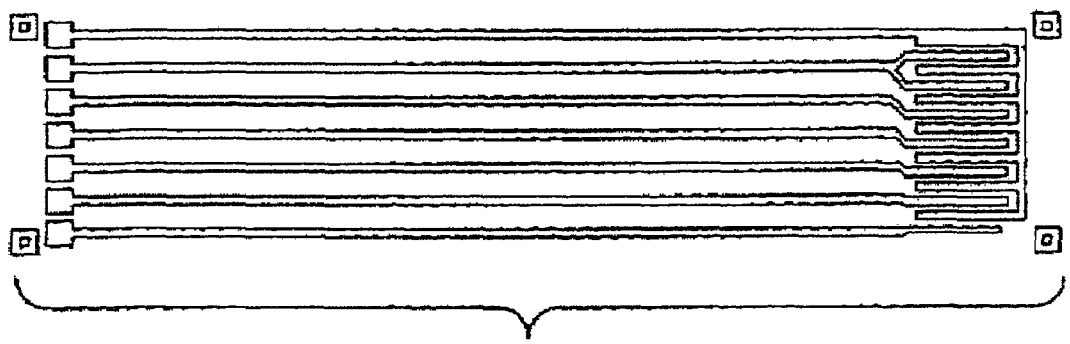
FIGS. 4A-4C depict the electrode pattern, dielectric pattern, and sensor material pattern used in preparing array chips for measurement in the chemical sensor array of the system shown in FIG. 1.
Figure 4B:
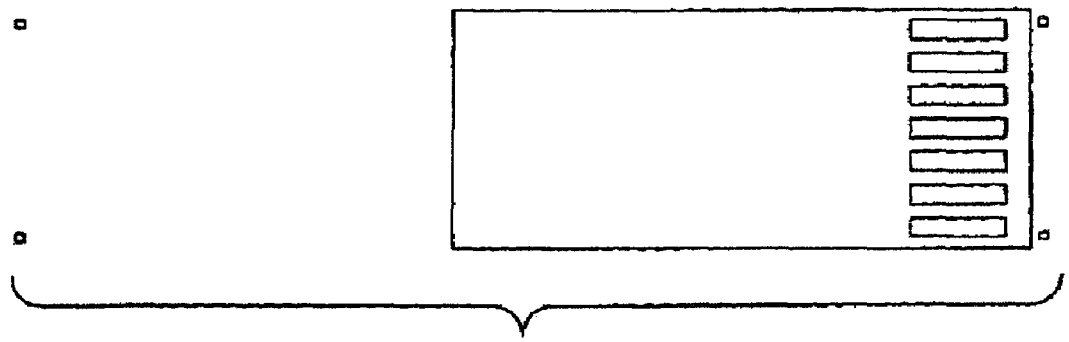
Figure 4C:

Techniques for screen-printing substrates with the electrodes and chemo-electro-active materials are illustrated in FIGS. 3 and 4A-4C. FIG. 3 depicts a method of using interdigitated electrodes overlaid with dielectric material, forming blank wells into which the chemo-electro-active materials can be deposited. FIGS. 4A-4C depict an electrode screen pattern for an array of 6 materials, which is printed on both sides of the substrate to provide for a 12-material array chip. Two of the electrodes are in parallel so it holds only 6 unique materials. Counting down from the top of the array shown in FIGS. 4A-4C, the top two materials can only be accessed simultaneously by the split electrode with which they have shared contact (FIG. 4A). Below that is the screen pattern for the dielectric material, which is screen printed on top of the electrodes on both sides of the substrate to prevent the material from being fouled by contact with the gas mixture, such as a deposit of soot that could cause a short (FIG. 4B). Below that is the screen pattern for the actual sensor materials (FIG. 4C). This is printed in the holes in the dielectric on top of the electrodes. When more than one material is used in the array, the individual materials are printed one at a time.

An electrical response is determined for each chemo-electro-active material upon exposure of the array to a gas mixture, and means for determining the response include conductors interconnecting the sensor materials. The conductors are in turn connected to electrical input and output circuitry (detecting circuitry 200), including data acquisition and manipulation devices (analytical device 300) as appropriate to measure and record a response exhibited by a sensor material in the form of an electrical signal. The value of a response, such as a measurement related to resistance, may be indicated by the size of the signal. One or more signals may be generated by an array of sensors as to each analyte component in the mixture, whether the analyte is one or more individual gases and/or one or more subgroups of gases.

An electrical response is determined for each individual chemo-electro-active material separately from that of each of the other chemo-electro-active materials. This can be accomplished by accessing each chemo-electro-active material with an electric current sequentially, using a multiplexer to provide signals differentiated between one material and another in, for example, the time domain or frequency domain. It is consequently preferred that no chemo-electro-active material be joined in a series circuit with any other such material. One electrode, by which a current is passed to a chemo-electro-active material, can nevertheless be laid out to have contact with more than one material. An electrode may have contact with all, fewer than all, of the chemo-electro-active materials in an array. For example, if an array has 12 chemo-electro-active materials, an electrode may have contact with each member of a group of 2, 3, 4, 5 or 6 (or, optionally, more in each instance) of the chemo-electro-active materials. The electrode will preferably be laid out to permit an electrical current to be passed to each member of such group of chemo-electro-active materials sequentially.

A conductor such as a printed circuit may be used to connect a voltage source to a sensor material, and, when a voltage is applied across the sensor material, a corresponding current is created through the material. Although the voltage may be AC or DC, the magnitude of the voltage will typically be held constant. The resulting current is proportional to both the applied voltage and the resistance of the sensor material. A response of the material in the form of either the current, voltage, or resistance may be determined, and means for doing so include commercial analog circuit components such as precision resistors, filtering capacitors and operational amplifiers (such as a OPA4340). As voltage, current, and resistance is each a known function of the other two electrical properties, a known quantity for one property may be readily converted to that of another.

Resistance may be determined, for example, in connection with the digitization of an electrical response. Means for digitizing an electrical response include an analog to digital (A/D) converter, as known in the art, and may include, for example, electrical components and circuitry (e.g., detecting circuitry 200 described below) that involve the operation of a comparator. An electrical response in the form of a voltage signal, derived as described above as a result of applying a voltage across a sensor material, may be used as an input to a comparator section (such as a LM339). The other input to the comparator may be driven by a linear ramp produced by charging a capacitor using a constant current source configured from an operational amplifier (such as a LT1014) and an external transistor (such as a PN2007a). The ramp may be controlled and monitored by a microcomputer (such as a T89C51CC01). A second comparator section may be also driven by the ramp voltage, but may be compared to a precise reference voltage. The microcomputer captures the length of time from the start of the ramp to the activation of the comparators to generate a signal based on the counted time.

The resistance of the sensor material is then calculated, or quantified as a value, by a microcomputer (e.g., analytical device 300 discussed below) from the ratio of the time signal derived from the voltage output of the material to a time signal corresponding to a known look-up voltage and, ultimately, to the resistance that is a function of the look-up voltage. A microprocessor chip, such as a T89C51CC01, can be used for this function. The microprocessor chip may also serve as means for determining a change in the resistance of a sensor material by comparing a resistance, determined as above, to a previously determined value of the resistance.

Electrical properties such as impedance or capacitance may be determined, for example, by the use of circuitry components such as an impedance meter, a capacitance meter or inductance meter.

Means for digitizing the temperature of an array of chemo-electro-active materials can include, for example, components as described above that convert a signal representative of a physical property, state, or condition of a temperature measuring device to a signal based on counted time.

In one embodiment, analysis of a multi-component gas mixture is complete upon the generation of an electrical response, such as resistance, in the manner described above. As a measurement of resistance exhibited by a sensor material upon exposure to a gas mixture is a function of the partial pressure within the mixture of one or more component gases, the measured resistance provides useful information about the composition of the gas mixture. The information may, for example, indicate the presence or absence within the mixture of a particular gas or subgroup of gases. In other embodiments, however, it may be preferred to manipulate, or further manipulate, an electrical response in the manner necessary to obtain information concerning the relative concentration within the mixture of one or more particular component gases or subgroups of gases, or to calculate the actual concentration within the mixture of one or more component gases or subgroups.

Means for obtaining information concerning the relative concentration within the mixture of one or more individual component gases and/or one or more subgroups of gases, or for detecting the presence of, or calculating the actual concentration of, one or more individual component gases and/or subgroups within the mixture, may include analytical device 300 (discussed in detail below) that incorporates either a PLS (Projection to Latent Structures) model or another linear modeling method; a back-propagation neural network model or another nonlinear modeling method; or a combination of the two, along with signal preprocessing and output post-processing. Signal preprocessing includes, but is not limited to, such operations as principle component analyses, simple linear transformations and scaling, logarithmic and natural logarithmic transformations, differences of raw signal values (e.g., resistances), and differences of logarithmic values. The analytical device 300 contains a model whose parameters have been previously determined, and that empirically models the relationship between the preprocessed input signal and information related to the gas concentration of the species of interest. Output post-processing includes, but is not limited to, all of the operations listed above for preprocessing, as well as their inverse operations.

The model is constructed using equations in which constants, coefficients or other factors are derived from predetermined values characteristic of a precisely measured electrical response of an individual sensor material to a particular individual gas or subgroup expected to be present as a component in the mixture to be analyzed. The equations may be constructed in any manner that takes temperature into account as a value separate and apart from the electrical responses exhibited by the sensor materials upon exposure to a gas mixture. Each individual sensor material in the array differs from each of the other sensors in its response to at least one of the component gases or subgroups in the mixture, and these different responses of each of the sensors is determined and used to construct the equations used in the model.

The analyte gas(es) contained in the mixture to which the chemo-electro-active material will be exposed can be a single gas, a subgroup of gases together, or one or more gases or subgroups mixed with an inert gas such as nitrogen. Particular gases of interest are donor and acceptor gases. These are gases that either donate electrons to the semiconducting material, such as carbon monoxide, $H_2S$ and hydrocarbons, or accept electrons from the semiconducting material, such as $O_2$, nitrogen oxides (commonly depicted as $NO_x$), and halogens. When exposed to a donor gas, an n-type semiconducting material will have a decrease in electrical resistance, increasing the current, and it, therefore, will show an increase in temperature due to $V^2/R$ heating. When exposed to an acceptor gas, an n-type semiconducting material will have an increase in electrical resistance, decreasing the current, and therefore will show a decrease in temperature due to $V^2/R$ heating. The opposite occurs in each instance with p-type semiconducting materials.

The geometry of a sensor material as fabricated in an array, including such characteristics as its thickness, selection of a compound or composition for use as the sensor, and the voltage applied across the array, can vary depending on the sensitivity required. The sensor materials are preferably connected in parallel in a circuit to which a voltage of about 1 to about 20, preferably about 1 to about 12 volts is applied across the sensor materials. When performing an analysis of a multi-component gas mixture, it is preferred that each chemo-electro-active sensor material in the array exhibit a different electrical response characteristic than each of the other chemo-electro-active materials in the array upon exposure to the mixture containing one or more analyte gases.

As noted, the types of electrical response characteristics that may be measured include AC impedance or resistance, capacitance, voltage, current or DC resistance. It is preferred to use resistance as the electric response characteristic of a sensor material that is measured to perform analysis of a gas mixture and/or a component therein. For example, a suitable sensor material may be that which, when at a temperature of about 400° C. or above, has a resistivity of at least about 1 ohm-cm, and preferably at least about 10 ohm-cm, and yet no more than about $10^6$ ohm-cm, preferably no more than about $10^5$ ohm-cm, and more preferably no more than about $10^4$ ohm-cm. Such a sensor material may also be characterized as that which exhibits, preferably at a temperature of about 400° C. or above, upon exposure to a gas mixture, a change in resistance of at least about 0.1 percent, and preferably at least about 1 percent, as compared to the resistance in the absence of exposure.

Regardless of the type of response characteristic that is measured for the purpose of analyzing a mixture and/or a gaseous component of interest therein, it is desirable that a sensor material be utilized for which a quantified value of that response characteristic is stable over an extended period of time. When the sensor material is exposed to a mixture containing the analyte, the concentration of the analyte being a function of the composition of the particular gas mixture in which it is contained, the value of the response of the sensor material will preferably remain constant or vary to only a small extent during exposure to the mixture over an extended period of time at a constant temperature. For example, the value of the response, if it varies, will vary by no more than about twenty percent, preferably no more than about ten percent, more preferably no more than about five percent, and most preferably no more than about one percent over a period of at least about 1 minute, or preferably a period of hours such as at least about 1 hour, preferably at least about 10 hours, more preferably at least about 100 hours, and most preferably at least about 1000 hours. One of the advantages of the types of sensor materials described above is that they are characterized by this kind of stability of response.

In applications in which the gas mixture is above about 400° C., the temperature of the sensor materials and the array may be determined substantially only, and preferably is determined solely, by the temperature of the gas mixture in which a gaseous analyst is contained. This is typically a varying temperature. When higher-temperature gases are being analyzed, it may be desirable to provide a heater with the array to bring the sensor materials quickly to a minimum temperature. Once the analysis has begun, however, the heater (if used) is typically switched off, and no method is provided to maintain the sensor materials at a preselected temperature. The temperature of the sensor materials thus rises or falls to the same extent that the temperature of the surrounding environment does. The temperature of the surrounding environment, and thus the sensors and the array, is typically determined by (or results from) substantially only the temperature of the gas mixture to which the array is exposed.

In applications in which the gas mixture is below about 400° C., it may be preferred to maintain the sensor materials and the array at a preselected temperature of about 400° C. or above. This preselected temperature may be substantially constant, or preferably is constant. The preselected temperature may also be about 500° C. or above, about 600° C. or above, or about 700° C. or above. This may be conveniently done with a heater incorporated with the array, in a manner as known in the art. The temperature of the gas mixture may also be below about 300° C., below about 200° C., or below about 100° C.

A change of temperature in the array may be indicated by a change in the quantified value of an electrical response characteristic, resistance for example, of a sensor material. At a constant partial pressure in the mixture of a gas of interest, the value of an electrical response characteristic of a sensor material may vary with a change in temperature of the array, and thus the material. This change in the value of an electrical response characteristic may be measured for the purpose of determining or measuring the extent of change of, and thus a value for, temperature. It is not required, but is preferred, that this measurement of temperature be made independently of information related to the compositional content of a gas mixture. This can be done by not using sensors that provide compositional information for the additional purpose of determining temperature, and, optionally, by connecting the temperature measuring device in parallel circuitry with the sensor materials, rather than in series. Means for measuring temperature include a thermocouple, a thermistor, or a pyrometer incorporated with an array of sensors. If the temperature-determining device is a thermistor, which is typically a material that is not responsive to an analyte gas, the thermistor is preferably made from a different material than the material from which any of the gas sensors is made. Regardless of the method by which temperature or change in temperature is determined, a temperature value or a quantified change in temperature is a desirable input, preferably in digitized form, from which an analysis of a mixture of gases and/or a component therein may be performed.

In the system and method of this invention, unlike various prior-art technologies, there is no need to separate the component gases of a mixture for purposes of performing an analysis, such as by a membrane or electrolytic cell. There is also no need when performing an analysis by means of this invention to employ a reference gas, such as for the purpose of bringing a response or analytical result back to a base line value. With the exception of preliminary testing, during which a standardized response value to be assigned to the exposure of each individual sensor material to each individual analyte gas is determined, the sensor materials are exposed only to the mixture in which an analyte gas and/or subgroup is contained. The sensor materials are not exposed to any other gas to obtain response values for comparison to those obtained from exposure to the mixture containing an analyte. The analysis of the mixture is, therefore, performed only from the electrical responses obtained upon exposure of the chemo-electro-active materials to the mixture containing the analyte. No information about an analyte gas and/or subgroup is inferred by exposure of the sensor materials to any gas other than the analyte itself as contained within the mixture.

This invention therefore provides systems and methods for directly sensing the presence and/or concentration of one or more gases in a multi-component gas system, comprising an array of at least two chemo-electro-active materials chosen to detect the gases in a multi-component gas stream. The multi-component gas system can be at essentially any temperature that is not so low or so high that the sensor materials are degraded or the sensor apparatus otherwise malfunctions. In one embodiment, the gas system may be at a lower temperature such as room temperature (about 25° C.) or elsewhere in the range of about 0° C. to less than about 100° C., whereas in another embodiment the gas mixture may at a higher temperature such as in the range of about 400° C. to about 1000° C.

The invention is applicable to gas mixtures that may be at higher temperatures—gases, for example, as found in combustion streams such as the exhaust or emission of an automobile, diesel engine, or home heating systems. The invention is also applicable, however, to gas mixtures derived from other sources, such as in manufacturing processes, waste streams, and environmental monitoring; or in systems in which odor detection is important and/or that are at lower temperature, such as in the medical, agricultural or food and beverage industries. An array of chemo-electro-active materials could be used, for example, to supplement the results of, or calibrate, a gas chromatograph. The gas mixture may therefore have a temperature that is about 100° C. or more, about 200° C. or more, about 300° C. or more, about 400° C. or more, about 500° C. or more, about 600° C. or more, about 700° C. or more, or about 800° C. or more, and yet is less than about 1000° C., is less than about 900° C., is less than about 800° C., is less than about 700° C., is less than about 600° C., is less than about 500° C., is less than about 400° C., is less than about 300° C., is less than about 200° C., or is less than about 100° C.

This invention also provides a chemical sensor for directly sensing the presence and/or concentration of one or more gases in a multi-component gas system, including a substrate, an array of at least two chemo-electro-active materials chosen to detect one or more predetermined gases in a multi-component gas stream, and a means to detect changes in electrical properties in each of the chemo-electro-active materials present upon exposure to the gas system.

A sensor that has the needed sensitivity, and that can operate to generate the types of analytical measurements and results described above, is obtained by selection of appropriate compositions of materials from which the sensor is made. Various suitable compositions of materials for this purpose are described above. The number of sensors in the array is typically greater than or equal to the number of individual gas components to be analyzed in the mixture.

The gas mixture to be analyzed may be emitted by a process, or may be a product of a chemical reaction that is transmitted to a device. In such instance, the invention may further include means for utilizing the electrical response of an array, and optionally a temperature measurement, for the purpose of controlling the process or the device.

Means for utilizing an electrical response of a sensor material, and optionally a temperature measurement, for controlling a process or device include a decision making routine to control, for example, the chemical reaction of combustion that occurs in an internal combustion engine, or to control the engine itself, or components or equipment associated therewith.

Combustion is a process in which the chemical reaction of the oxidation of a hydrocarbon fuel occurs in the cylinder of an engine. An engine is a device to which a result of that chemical reaction is transmitted, the result being the force generated by the combustion reaction to the work necessary to move the piston in the cylinder. Another example of a process that emits a multi-component mixture of gases is the chemical reaction that occurs in a fuel cell, and other examples of a device to which a product of a chemical reaction is transmitted is a boiler, such as used in a furnace or for power generation, or a scrubber in a stack to which waste gases are transmitted for pollution abatement treatment.

In the case of an engine, to control the process of combustion or the operation of the engine itself, a microcomputer (such as a T89C51CC01 from Atmel Corporation of San Jose, Calif.) may perform a multitude of decision-making routines about various parameters of the process of combustion or about operating characteristics of the engine. The microcomputer gathers information about the compositional content of the engine exhaust, and does so by obtaining the responses of an array of chemo-electro-active materials that have been exposed to the stream of exhaust, and optionally obtains a temperature measurement. The information is temporarily stored in a random access memory, and the microcomputer then applies one or more decision-making routines to the information.

A decision-making routine (e.g., analytical device 300) may utilize one or more algorithms and/or mathematical operations to manipulate the acquired information to generate a decision in the form of a value that is equivalent to a desired state or condition that should be possessed by a particular parameter of the process, or by an operating characteristic of the device. Based on the result of a decision-making routine, instructions are given by or are controlled by the microcomputer that cause an adjustment in the state or condition of a parameter of the process or an operating characteristic of the device. In the case of the process embodied by the chemical reaction of combustion, the process can be controlled by adjusting a parameter of the reaction, such as the relative amount of the reactants fed thereto. The flow of fuel or air to the cylinder, for example, can be increased or decreased. In the case of the engine itself, being a device to which a result of the reaction of combustion is transmitted, control can be accomplished by adjusting an operating characteristic of the engine such as torque or engine speed.

An internal combustion engine and the associated components and equipment, controlled by the systems and methods of this invention, can be used for many different purposes including, for example, in any type of vehicle for transportation or recreation such as a car, truck, bus, locomotive, aircraft, spacecraft, boat, jet ski, all-terrain vehicle, or snowmobile; or in equipment for construction, agriculture, maintenance or industrial operations such as pumps, lifts, hoists, cranes, generators, tractors, or equipment for demolition, earth moving, digging, drilling, mining or grounds keeping.

The examples set forth in U.S. patent application Ser. Nos. 10/117,472 and 09/977,791 are not repeated herein, but are incorporated by reference herein.

B. The Detecting Circuitry

As noted above, in accordance with the present invention there may be provided chemical sensors comprised of materials whose AC impedance changes when exposed to certain gases. Accordingly, several exemplary detecting circuits 200 according to the present invention for measuring such AC impedances will now be described. Some of the circuit concepts are found, for example, in U.S. Pat. No. 4,554,639, which is owned by the assignee hereof and which is incorporated herein by reference.

The sensor array 100 is based on the variation of resistance elements in response to known contaminants. The measurement of contamination is complicated by the variation in resistance due primarily to temperature changes in the environment of the sensor array 100. The presumption is that the sensor resistor elements are a function of temperature, T, and concentration, C, such that R(T,C) is of the form R(T)K(C). Important sensor element characteristics include: (1) the dynamic range of resistance values to be measured; (2) the expected sensitivity to the measured contamination; (3) the time response; and (4) the noise characteristics.

The system requirements, in conjunction with the resistor element characteristics, that dictate a measurement approach include: (1) measurement accuracy; (2) measurement resolution; (3) update rate; and (4) calculation complexity. Accuracy and resolution interact with the dynamic range and sensitivity. Being able to measure the resistance to 0.1% accuracy does not ensure that the concentration can be measured to the same precision. If the full-scale change in resistance is only 10% of the nominal resistance, the concentration reading is accurate to only 1% of the full-scale value.

The time response also affects the update rate. Shannon's sampling theorem states that the sample rate must be greater than twice the highest frequency component of a band limited signal. Since no physical signal is band limited, this condition can only be approximated. The response of a sensor to a particular excitation is dependent on the frequency characteristics of the excitation and the frequency response of the sensor. If the sensor is first-order with a 3 dB bandwidth of $f_n=1/(2\pi T_c)$ Hz, where $T_c$ is the time constant. The choice of sampling frequency determines the maximum errors introduced by sampling process. In this example, a sampling rate of $10*f_n$ would guarantee errors of less than 1% due to sampling regardless of the characteristic of the excitation. If the excitation is slowing varying, then smaller sampling times are appropriate. For most application, the sensor response is essentially instantaneous relative to the frequency of changes in gas composition. In this case, the sampling rate can be determined by considering the excitation only. Sampling rates are chosen so that errors from sampling are below the noise level of the signal. Filtering of the signals can reduce this noise even further.

Resolution is a different concept than accuracy. An analog-to-digital converter ("ADC") may have a resolution of 12 bits (1 in 4096) and still only have an accuracy of only 0.1%. The 12 bits, even if the ADC is accurate and linear to ±½ bit, can result in much lower accuracy of the measured value depending on the full-scale change.

Each sensor will also have different calibration constants that must be available to the microcontroller. It would be desirable to have the constants associated with the sensor if the sensor and electronics have to be separated. The ideal device for constant memory is a serial EEPROM. For a normal automotive temperature range (−40° C. to 125° C.), these devices are inexpensive, but so far, none have been found that can withstand the high temperature environment expected in the sensor itself. With a separate sensor and electronics unit, it is possible to integrate the memory chip in the connector between the two units.

Figure 5:
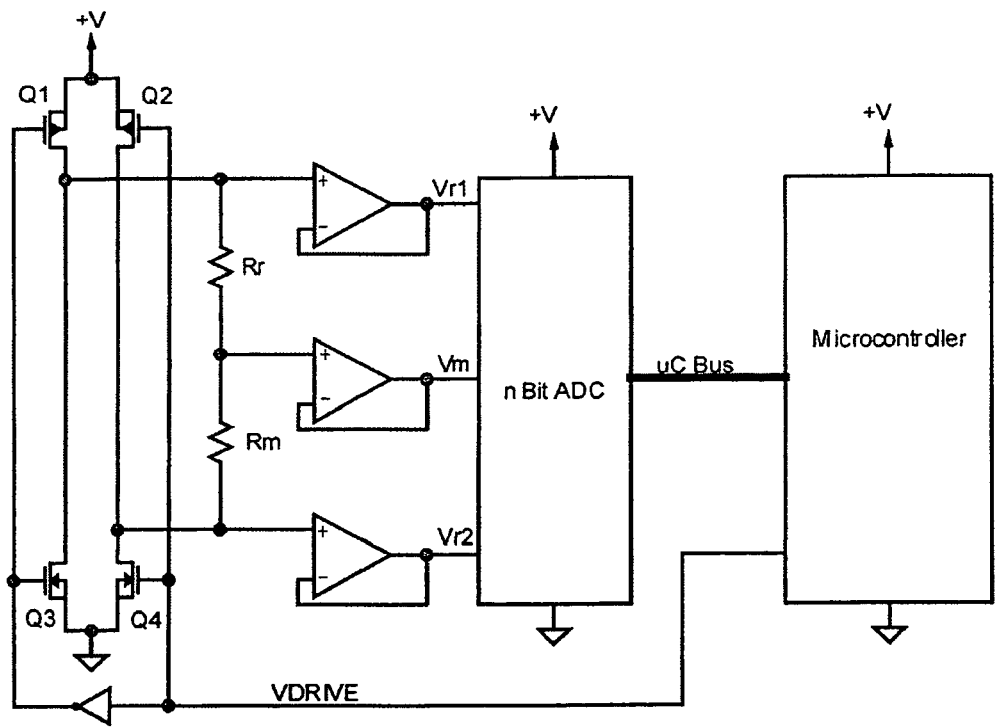
FIG. 5 is an electrical circuit schematic showing a linear resistance ratio measurement approach.

Since the resistor is to be driven AC complicates the measurement. A simple approach is to measure a resistor as a ratio against a reference resistor, as shown in FIG. 5. The technique requires two readings, first with the VDRIVE signal low and then with the VDRIVE signal high. In both cases the limits, Vr1 and Vr2, as well as, the divider point, Vm, are measured. These two measurements give the following result:

$$V1 = \frac{Rm}{Rm+Rr}, \text{ and}$$

$$V2 = \frac{Rr}{Rm+Rr}.$$

Thus, Rm=

$$Rr \cdot \frac{V1}{V2}.$$

The conductance, Gm, is simply an inversion of this equation.

The purpose of measuring the limits is to allow the readings to be corrected for voltage drops expected in the measurement technique. Since the measurement is made against a reference resistor, Rr, it must be stable and accurate. For this reason, it would be part of the measurement circuit, not in the sensor itself.

A virtue of this approach is that no absolute reference is needed in the measurement circuitry. Further, resolution and accuracy are determined by the minimum number of bits used. The exact dynamic range, D(n,m), for an ADC with n bits resolution and an estimate resolution of m bits, is given by, $D(n,m)=2^{n-m}-1$, and the resolution of the estimate of resistance ratio, E(m), is given by, $E(m)=2^m$.

The calculation of resistance in this example requires that the readings be corrected for the offsets of the drive level limits, and then performing a division. The ratio of Rm/Rr must be such that the expected range of change in Rm does not exceed the dynamic range limits. This approach is adaptable to reading multiple sensor resistors simultaneously by adding a buffer amplifier and local reference resistor for each sensor resistor. For a six-sensor system, an eight-channel ADC would be adequate to measure all sensors simultaneously. To measure more sensors would require multiplexing the inputs to the ADC. It is possible to make readings on all 12 channels in each cycle of a drive frequency of 100 Hz.

Figure 6:
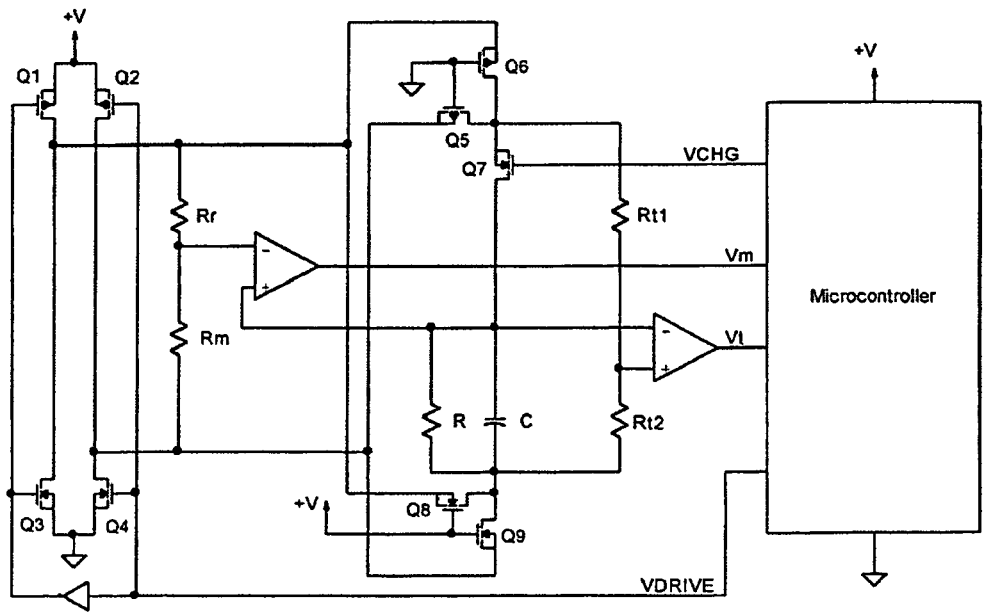
FIG. 6 is an electrical circuit schematic showing a measurement approach that uses a timing technique to produce a log measurement of an unknown resistance.

A variation in the above approach uses a timing technique to produce a log measurement of the unknown resistance. This approach is adaptable to direct interface to a microcontroller and requires no ADC as shown in FIG. 6. The microcontroller, via VDRIVE, controls field-effect transistors ("FETs"), Q1 to Q4, to alternate the direction of current flow through Rm and Rr. FETs, Q5, Q6, Q8 and Q9, undo the effects of FETs, Q1 to Q4, to maintain a unidirectional reference to the timing circuit. After setting the state of current flow, the microcontroller enables Q7 to charge capacitor C to the upper rail. The reference to the timing comparator, as established by Rt1 and Rt2, allows the measurement of the time constant, τ, of R and C. A timer is started when Q7 is turned off and the time that Vt and Vm are high is measured. On the next phase of VDRIVE, the process is repeated.

The first time measurement, t1, corresponds to voltage V1, such that, $$V1 = V \cdot e^{\frac{-t1}{\tau}} = V \cdot \frac{Rm}{Rm+Rr}.$$

The second time measurement, t2, corresponds to V2, $$\text{or } V2 = V \cdot e^{\frac{-t2}{\tau}} = V \cdot \frac{Rr}{Rm+Rr}.$$

Simplifying and solving for the natural log of Rm gives, $$\ln(Rm) = \frac{t1-t2}{\tau} + \ln(Rr).$$

Note that the time, τ, is measured on both halves of the cycle so minor variations in the values of timing components, R and C, are not significant. The measurement is actually based on the ratio of timing resistors, Rt1 and Rt2, and the stability and accuracy of the local reference resistor, Rr.

Figure 7:
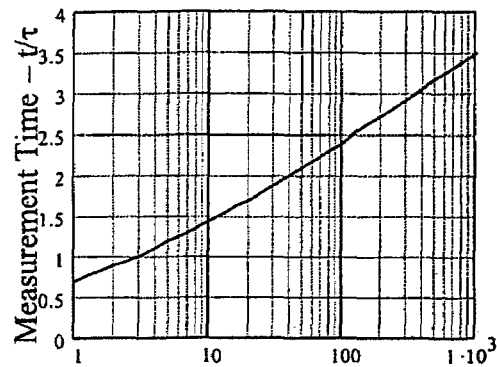
FIGS. 7 and 8 are graphs showing the timing characteristics of the electrical circuit shown in FIG. 6 normalized to $\tau$ as a function of the dynamic range of Rm, where FIG. 7 provides the total time (t) for the measurement and FIG. 8 provides the time difference ($\Delta t$) for the measurement.
Figure 8:
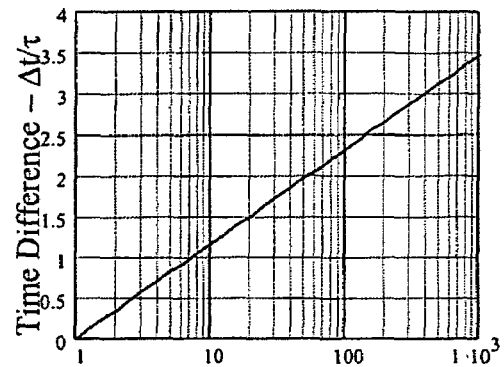

FIGS. 7 and 8 present timing characteristics normalized to τ as a function of the dynamic range of Rm, Dr. FIG. 7 gives the total time, t, for the measurement based on the equation, $t(Dr)=\tau \cdot \ln(\sqrt{Dr}+1)$. FIG. 8 gives the time difference, Δt, based on the equation, $\Delta t(Dr)=\tau \cdot \ln(\sqrt{Dr})$.

Figure 9:
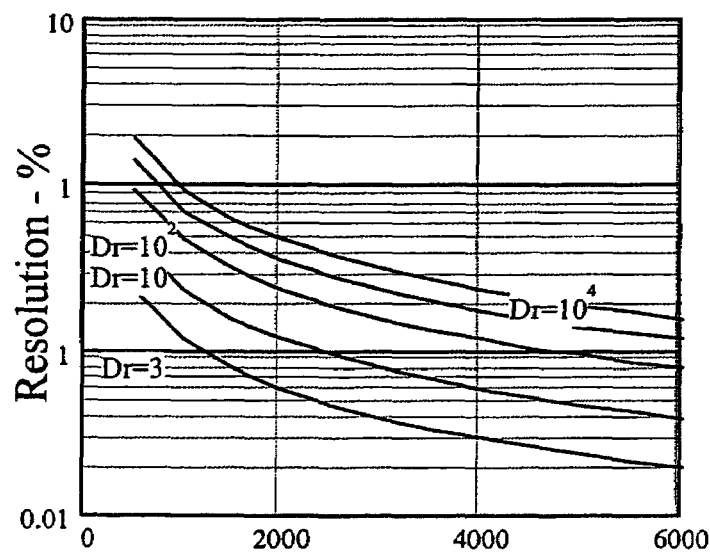
FIG. 9 is a graph showing the resolutions, in percents, as a function of the precision of the $\tau$ measurement, in counts, for the electrical circuit shown in FIG. 6.

The virtue of measuring the log of Rm is that accuracy of the measurement is a percent of the reading rather than a percent of the full-scale. FIG. 9 shows the resolutions, in percent, as a function of the precision of the τ measurement, in counts as given by, $$Res(Dr, N) = 100 \cdot \left(10^{\frac{\log(Dr)}{N}} - 1\right).$$

Five curves are given for dynamic ranges of 3, 10, 100, 103, and 104.

The penalty paid for added accuracy and wider dynamic range is measurement time. The primary factor impacting the measurement time is the maximum counting rate of the microcontroller. Several microcontrollers incorporate PCAs (programmable counter arrays) intended for high-speed timing functions. The microcontrollers can count at rates of ¼ the crystal frequency. For a practical 16 MHz crystal, the time resolution is thus 250 ns. From FIG. 9, for a dynamic range of 100 and a resolution of 0.1%, the value of τ required is approximately 1.25 ms. From FIG. 6 the required maximum time for the measurement is 2.4 times τ, or 3 ms.

The simplest microcontroller that could be used to implement this approach and meet the automotive temperature environment (125° C.) is the 8xFx51 series microcontroller available from Intel Corporation of Santa Clara, Calif. This microcontroller has a 5-channel PCA, which would allow simultaneous measurement of four sensor resistors. To measure more resistors requires multiple sample periods. This microcontroller does not have a built in CAN interface. The 8xC196 microcontroller, also available from Intel Corporation, is intended for automotive applications up to 125° C., has the capability of measuring up to 9 resistors simultaneously using this technique. Each unknown resistor to be measured requires a comparator and local reference resistor.

Figure 10:
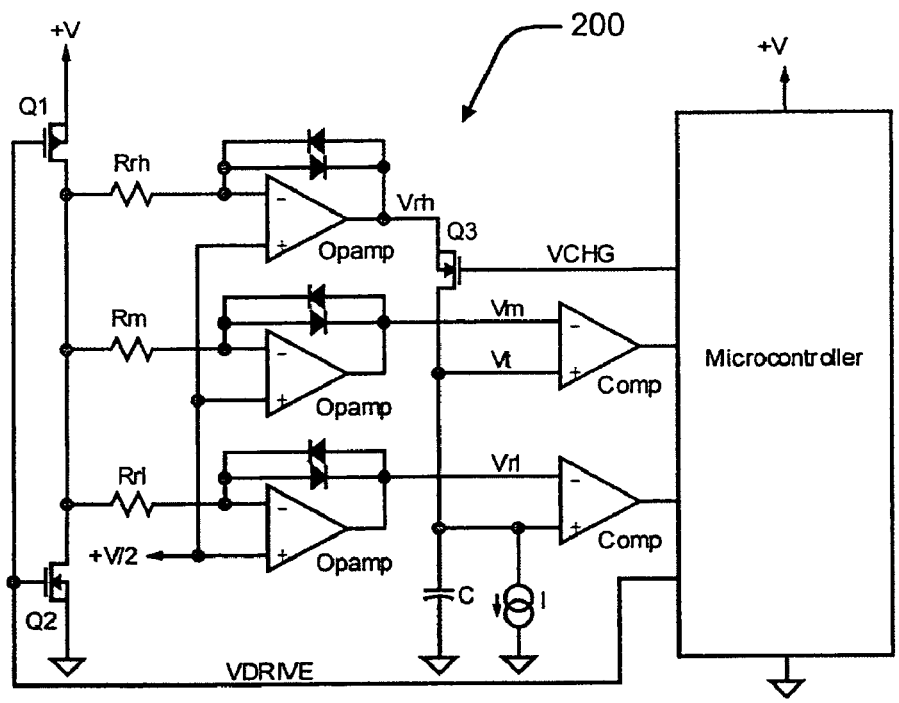
FIG. 10 is an electrical circuit schematic of an analog logged measurement in accordance with the present invention and for use in the detecting circuitry of the system shown in FIG. 1.

One measuring circuit in accordance with the detecting circuitry 200 of the present invention is shown in FIG. 10. In this circuit, Rm represents a material whose AC impedance will be determined. The material receives a drive frequency that is preferably 100 Hz.

As known in the art, the current and voltage relationship in a diode follows the equation, $$Vd = \frac{k \cdot T}{q} \cdot \ln\left(\frac{I}{I_o}\right) + V_o(I_o, T),$$

where, Vd is the voltage across the diode, I is the current through the diode, k is Boltzmann's Constant, T is the absolute temperature, q is the electron charge, $I_o$ is a reference current, and $V_o(I_o,T)$ is a voltage dependent on $I_o$ and T.

At normal room temperature, a change in current by a factor of 10 causes a change in the diode voltage Vd of 60 mV. Measurement of the voltage is complicated by the temperature sensitivity of both the measured value and the offset voltage $V_o$. However, assuming matched diodes, which are inherent in an integrated circuit, these unknowns can be eliminated by using similar circuits with known currents as in the present invention.

In the circuit of FIG. 10 measurements are only made while VDRIVE is high and the current is being drawn through FET Q2. On the opposite phase of VDRIVE, when FET Q1 is active, balanced current is drawn. After setting VDRIVE high, FET Q3 is activated to charge capacitor, C, to the upper reference voltage, Vrh, as determined by resistor, Rrh. Q3 is then turned off and C discharges linearly through the constant current source, I. Using its programmable counter arrays (PCA's), the microcontroller measures the times tm and tr for the timing voltage Vt to pass voltages Vm and Vr1. Vm is thus, $$Vm = \frac{tr - tm}{tr} \cdot (Vrh - Vrl) + Vrl.$$

From the diode equation, the voltages Vm, Vrh, and Vrl are given by, $$Vm = \frac{k \cdot T}{q} \cdot \ln\left(\frac{V}{Rm \cdot I_o}\right) + V_o(I_o, T),$$

$$Vrh = \frac{k \cdot T}{q} \cdot \ln\left(\frac{V}{Rrh \cdot I_o}\right) + V_o(I_o, T), \text{ and}$$

$$Vrl = \frac{k \cdot T}{q} \cdot \ln\left(\frac{V}{Rrl \cdot I_o}\right) + V_o(I_o, T).$$

Substituting for the voltages, and solving for ln(Rm) gives, $$\ln(Rm) = \ln(Rrh) + \frac{tm}{tr} \cdot \ln\left(\frac{Rrl}{Rrh}\right).$$

Because all the unknowns normalize out, the measurement of ln(Rm) is only a function of the values of resistors Rrl and Rrh. If more than one Rm is to be measured, an additional operational amplifier ("opamp") and diode pair must be added for each additional Rm. The outputs of the comparators can be multiplexed into the microcontroller timer inputs.

The resolution of the measurement is determined by the dynamic range Dr, the reference time tr and the counter resolution of the microcontroller. Assuming the ratio of Rrl/Rrh determines the dynamic range and a tm between zero and tr, the resolution data shown in FIG. 9 applies directly to this approach. Accordingly, for a dynamic range of 100, a resolution of 0.1%, and a microcontroller clock frequency of 16 MHz, the required time for measurement by the microcontroller is 1.25 ms.

Figure 11:
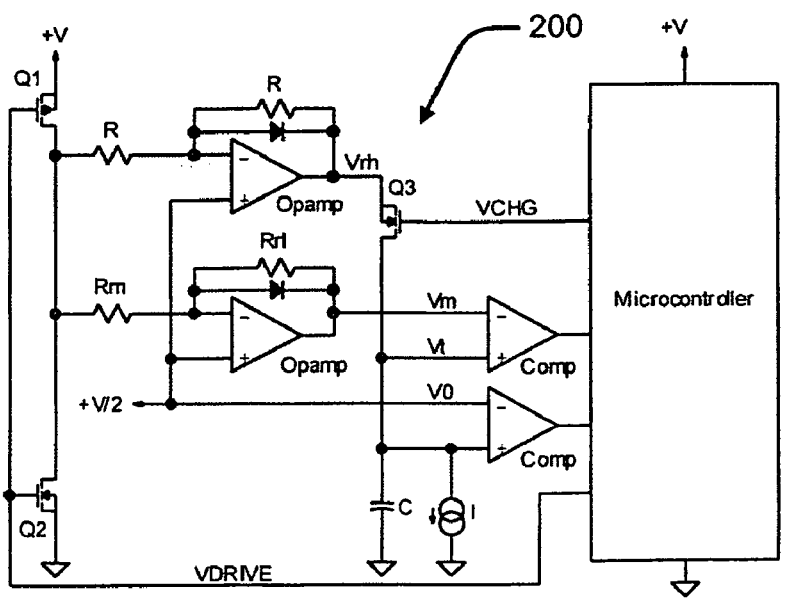
FIG. 11 is an electrical circuit schematic of a timed linear resistance measurement in accordance with the present invention and for use in the detecting circuitry of the system shown in FIG. 1.

Another variation of the approach of FIG. 10, and in accordance with the present invention, is shown in FIG. 11. Again, Rm represents a material whose AC impedance will be determined, and the material receives a drive frequency that is preferably 100 Hz. In this circuit, an operational amplifier is used to interface to Rm. The feedback resistor, Rrl, is selected to correspond to the minimum value of resistance expected in the unknown, Rm. This circuit only makes a measurement when VDRIVE is high. When VDRIVE is low, equal but opposite current is drawn through Rm. When Q2 is on, the timing capacitor, C, is charged to a reference voltage, Vrh, determined by two equal value resistors. If Rm is infinite, the measured voltage Vm is equal to V0 or +V/2. Again, the times for Vt to pass Vm and V0 are measured. The value of Rm is thus, $$Rm = \frac{Rrl}{1 - \frac{tm}{tr}}.$$

Expressing the result in terms of conductance, Gm, gives, $$Gm = Grl \cdot \left(1 - \frac{tm}{tr}\right).$$

Since this is a direct measurement of Rm, the resolution is strictly a function of the dynamic range and the timing resolution. By picking a unique reference resistor value for Rrl to go with each unknown resistor, the dynamic range and resolution of each resistor measurement path can be established independently.

Figure 12:
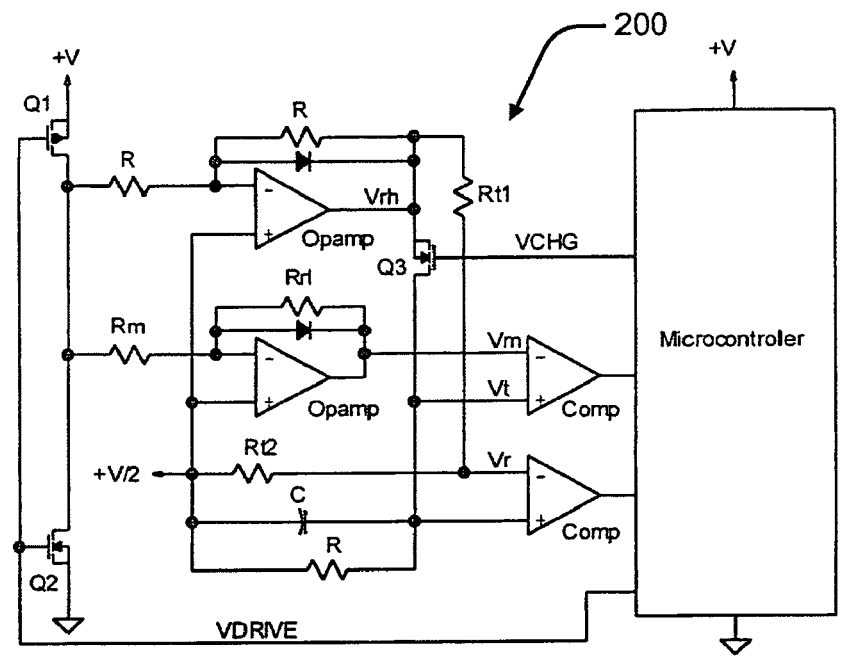
FIG. 12 is an electrical circuit schematic of a timed log measurement in accordance with the present invention and for use in the detecting circuitry of the system shown in FIG. 1.

A variation of the circuit of FIG. 11, as shown in FIG. 12, and in accordance with the present invention, results in a direct timed log measurement of the resistance of conductance. The current source of FIG. 11 is replaced with a resistor, and resistors Rt1 and Rt2 are added to establish a reference voltage, Vr. Assuming that Vr is set to be equal to that of one time constant, τ, the equations for ln(Rm) and ln(Gm) are, $$\ln(Rm) = \ln(Rrl) + \frac{tm}{t\tau}, \text{ and } \ln(Gm) = \ln(Grl) - \frac{tm}{t\tau}.$$

An advantage of this circuit over the circuit of FIG. 10 is that it can be configured without the requirements of matched diodes. It can thus be implemented with off-the-shelf components.

As many as 12 resistors may need to be measured. No available microcontrollers can measure that many resistors simultaneously using the timing technique. However, it is possible to measure 12 resistors using an ADC in conjunction with a multiplexer in accordance with the present invention. Using a timing approach, multiplexing can take place in various ways. The sensor interface circuitry can be duplicated and the outputs multiplexed at the input to the microcontroller. Multiplexer circuits at the inputs to the sensor interface circuit are also possible but not preferred.

Figure 13:
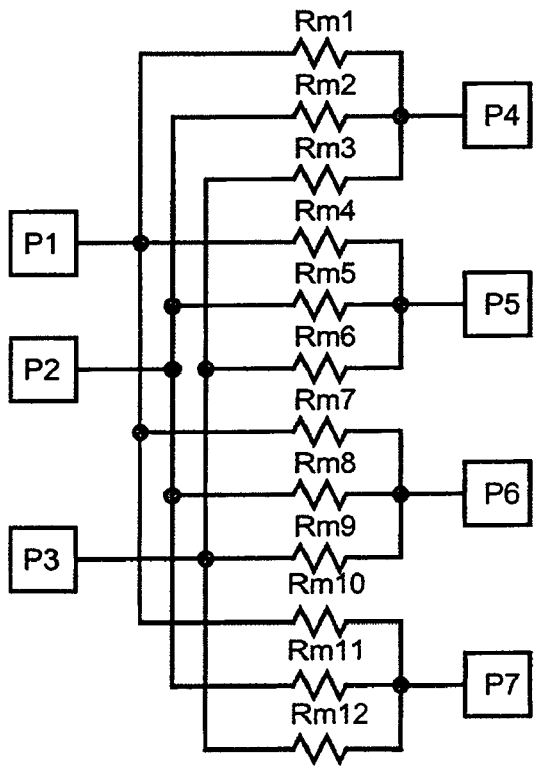
FIG. 13 is an electrical circuit schematic of a multiplexed sensor configuration in accordance with the present invention and for use in the detecting circuitry of the system shown in FIG. 1.

In circuit configurations using operational amplifiers to interface to the sensor resistors, such as those of FIGS. 10-12, a unique multiplexing technique of the present invention can be used. Assuming a 12-resistor sensor connected as shown in FIG. 13, only 7 wires need to be supplied to the sensor, rather than 13 wires. Pads, P4-P7, drive measurement interface circuits. Pads, P1-P3, are driven by separate, tri-state output circuits. By grouping sensor resistors with similar sensitivities, it is still possible to take advantage of tailoring the dynamic range and measurement resolution.

Drive multiplexing requires that transistors, Q1 and Q2, of FIGS. 10-12 be replicated for each drive path. The gates of all drive transistors must be driven independently to allow only one to be on at a time. A measurement of each resistor will require three cycles of the drive waveform. When the Rm are driven at 100 Hz, 33 measurements per second is practical and allows approximately 2.5 ms for each reading, or approximately 10,000 counts with a 16 MHz crystal.

Figure 14:
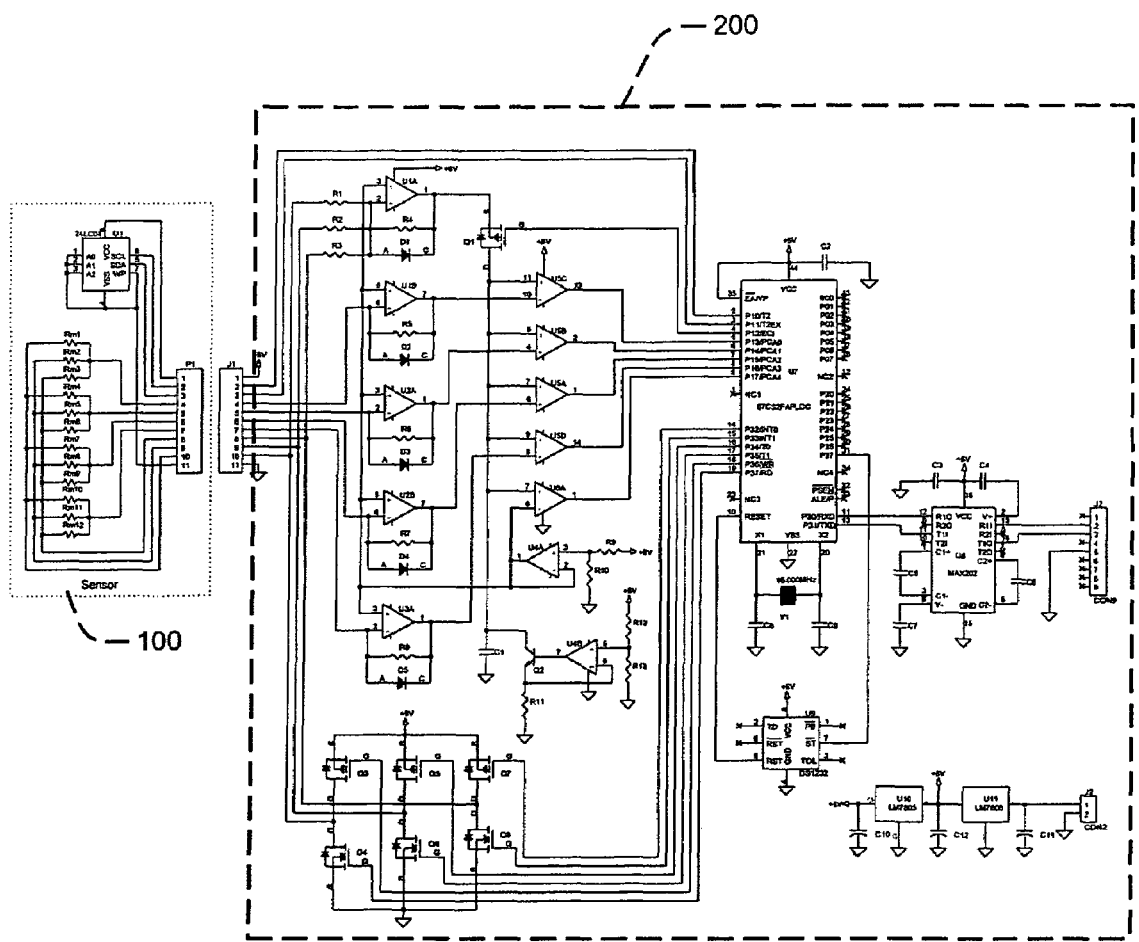
FIG. 14 is an expanded electrical circuit schematic in accordance with the present invention based on and adding additional capability to the electrical circuit shown in FIG. 11.

Shown in FIG. 14 is an expanded circuit in accordance with the present invention and based upon and adding additional capability to the circuit shown in FIG. 11. The circuit shown in FIG. 14 allows for the simulations measurement of 12 Rm. Such simultaneous measurement of 12 Rm using the timing techniques employed in the circuits of FIGS. 10 and 11 is not possible using currently-available microcontrollers. However, the circuit of FIG. 14 includes a multiplex interface, which overcomes this limitation. This multiplex interface circuit is shown in detail in FIG. 13.

For purposes of illustration, FIG. 14 shows the use of a 87C52 microcontroller (available from Intel Corporation) with five programmable counter arrays. However it will be obvious to those of skill in the art that other microcontrollers may be used. FIG. 14 additionally shows an EIA-232 (also known as RS-232) interface. A CAN interface, as is typically used in automotive applications, may be used in place of or in addition to the EIA-232 interface by wiring into the microcontroller's bus.

All measurement techniques presented rely on local reference resistors. No absolute reference is needed for any of the circuits. Self-compensation is inherent in all the approaches. In the circuits based on timing, variations in timing component values with temperature are normalized by calibrating the timing circuit along with each measurement. Thus, the only components necessary for accuracy are the local reference resistors.

C. The Analytical Device

The apparatus and method set forth in U.S. patent application Ser. Nos. 10/117,472 and 09/977,791 generate information, via detecting circuit that needs to be computer processed to calculate the concentration or constituents of a multi-component gas system. The analytical system and method of the present invention provides the mechanisms to calculate the concentration or constituents of one or more analyte gases in the mixture of the system.

1. Hardware of the Analytical Device

Figure 15:
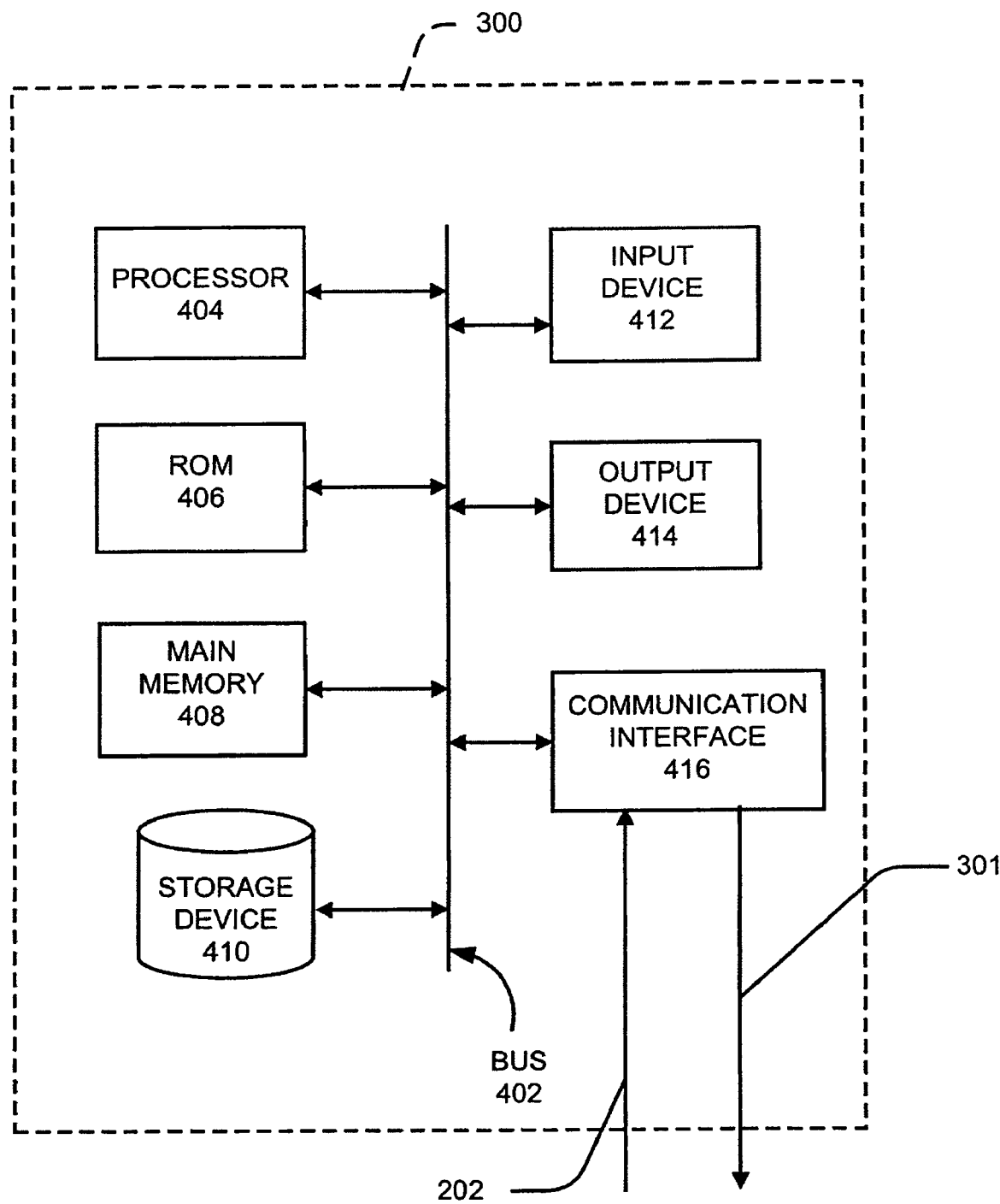
FIG. 15 is a schematic diagram showing a computing entity for use with the analytical device of the system shown in FIG. 1.

Analytical device 300 preferably comprises a conventional computing entity, or a series of connected conventional computing entities (e.g., a microcomputer such as the T89C51CC01 discussed above). As shown in FIG. 15, each computing entity may include a bus 402 interconnecting a processor 404 a read-only memory (ROM) 406, a main memory 408, a storage device 410, an input device 412, an output device 414, and a communication interface 416. Bus 402 is a network topology or circuit arrangement in which all devices are attached to a line directly and all signals pass through each of the devices. Each device has a unique identity and can recognize those signals intended for it. Processor 404 includes the logic circuitry that responds to and processes the basic instructions that drive the computer. ROM 406 includes a static memory that stores instructions and date used by processor 404.

Computer storage is the holding of data in an electromagnetic form for access by a computer processor. Main memory 408, which may be a RAM or another type of dynamic memory, makes up the primary storage of the computer. Secondary storage of the computer may comprise storage device 410, such as hard disks, tapes, diskettes, Zip drives, RAID systems, holographic storage, optical storage, CD-ROMs, magnetic tapes, and other external devices and their corresponding drives.

Input device 412 may include a keyboard, mouse, pointing device, sound device (e.g. a microphone, etc.), biometric device, or any other device providing input to the computer. Output device 414 may comprise a display, a printer, a sound device (e.g. a speaker, etc.), or other device providing output from the computer. Communication interface 416 may include network connections, modems, or other devices used for communications with other computer systems or devices.

As will be described below, analytical device 300 consistent with the present invention may calculate the concentration or constituents of a multi-component gas system. Device 300 performs this task in response to processor 404 executing sequences of instructions contained in a computer-readable medium, such as main memory 408. A computer-readable medium may include one or more memory devices and/or carrier waves.

Execution of the sequences of instructions contained in main memory 408 causes processor 404 to perform processes that will be described later. Alternatively, hardwired circuitry may be used in place of or in combination with software instructions to implement processes consistent with the present invention. Thus, the present invention is not limited to any specific combination of hardware circuitry and software.

2. Processing by the Analytical Device

Analytical device 300 receives inputs (e.g., resistances) 202 from the chemical sensor array 100, via detecting circuitry 200, and calculates the concentrations of constituents (e.g., $NO_x$) of a multi-component gas system based upon the received inputs. At any given point in time, the sensor array 100 provides a set of output resistances that must be converted into gas concentrations in a multi-component gas system.

a. Algorithm Development (Off-line Environment)

Figure 16:
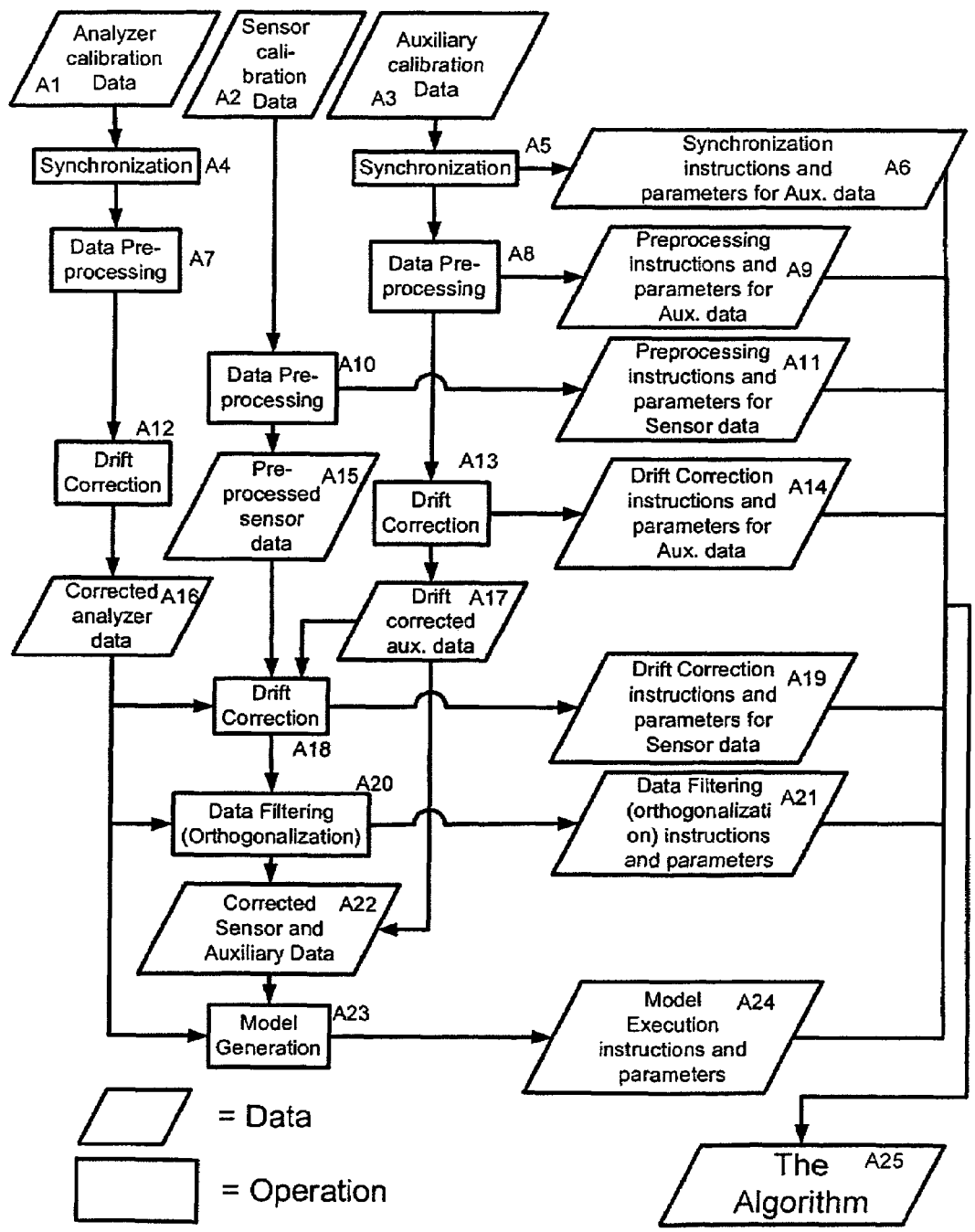
FIG. 16 is a flow chart showing an algorithm development process in the off-line environment of the present invention.

FIG. 16 shows the method or process by which calibration models capable of predicting analyte (gas) concentrations from sensor resistances can be generated. This process is required to obtain the parameters that can be used at a later time to make predictions in real-time and on-line.

(1) Algorithm Development Data Sources (a) Sensor Calibration Data

The "Sensor Calibration Data" parallelogram A2 corresponds to the sensor input resistances 202 discussed previously, which have been collected during one or more calibration experiments.

(b) Auxiliary Calibration Data

The "Auxiliary Calibration Data" parallelogram A3 represents inputs that can. be obtained on-line from other parts of the combustion system, the engine control unit (ECU) or other data sources located on the vehicle. These are matching data that were collected during the same calibration experiment(s) that were mentioned earlier (under "Sensor Calibration Data"). Such inputs can include, but are not limited to, the fuel-to-air ratio, the engine speed in revolutions per minute, the engine torque, the engine power, the engine inlet air temperature, and the exhaust gas temperature. They can be in the form of resistance, voltage, or current. However, they must be continuously available to the sensor when it is operating in real time.

(c) Analyzer Calibration Data

The "Analyzer Calibration Data" parallelogram A1 represents inputs obtained from one or more devices capable of measuring the concentration(s) of the exhaust gas(es) that the user would like the sensor to measure. These are matching data that were collected during the same one or more calibration experiments that were mentioned earlier (under "Sensor Calibration Data"). The inputs are typically available only in the off-line, algorithm development environment.

The following operations are commonly undertaken during off-line algorithm development. For a given application, it is not necessary that all of these operations be done, or that they be done in the sequence that they are listed below.

(2) The Algorithm Development Process (a) Synchronization

The "Synchronization" boxes A4 and A5 in the process flow from the "Auxiliary Calibration Data" and "Analyzer Calibration Data" parallelograms represent a step to align measurements obtained from these two data streams with those from the sensor on a common time basis. "Analyzer Calibration Data" often requires synchronization to account for, among other things, time lags introduced by the length of time a sample takes to arrive at the analyzer, the length of time the analyzer requires to measure the sample and the length of time the analyzer output takes to arrive at the data logging device. Typically, the length of time a sample takes to arrive at the analyzer is the major contributor to the time delay. "Auxiliary Calibration Data" often requires synchronization to account for, among other things, the length of time associated with other sensing devices' measurement lag times, the length of time associated with the location of each other device relative to the sensor array 100 in the combustion and exhaust system, and the length of time required to compute an output in the ECU.

If synchronization is required for the auxiliary calibration data A3, the parameters and instructions for such synchronization A6 are recorded, so that they can be properly implemented during real-time operation of the sensor.

(b) Data Pre-processing

The sensor inputs and the synchronized inputs from the analyzer(s) and auxiliary data sources can then be pre-processed (boxes A7, A8 and A10) to make the magnitude and range of each input compatible with the others. This step is often required to provide proper relative weight of each individual input source for the model building process, or to remove undesirable or irrelevant effects from the input source data.

Signal pre-processing includes one or more of the following mathematical operations: (1) to center the signal(s) to a mean value; (2) to scale the signal(s); (3) to normalize, or scale to unit variance, the signal(s); (4) to filter the signal(s) by digital means to remove dropped readings, such as for example, median filtering; or (5) to transform the signal(s), such as for example, by subjecting them to computing the first order (or another, higher order) derivative of the readings. Other means of pre-processing the signal(s) involve transforming the readings through one or more of the following mathematical operations: (1) compute the logarithm, or it's inverse, the exponential, of the signal(s); (2) compute a trigonometric, or inverse trigonometric, function of the signal(s); (3) compute a hyperbolic, or inverse hyperbolic, function of the signal(s); or (4) raise the signal(s) to a power n where n is a real number. Any of these operations may be conducted individually on the signal(s), or in a prescribed sequence.

The data that is output from the pre-processing operation(s) can contain any combination of un-preprocessed data with data that was pre-processed by various single operations or sequences of operations.

Once an optimal pre-processing is determined, the numerical parameters and pre-processing instructions must be recorded, so that they can be properly implemented during real-time operation of the sensor. These parameters and instructions can be stored in a processor that is embedded with the sensor device. The parallelograms named "Pre-processing Instructions and Parameters for Aux. Data" (A9) and "Pre-processing Instructions and Parameters for Sensor Data" (A11) in FIG. 16 represent these stored parameters and instructions for the two data streams.

(c) Drift Correction

As used herein, the term "drift" refers to a time-varying (temporal) change in one or more characteristics of the sensor pad response (i.e., baseline offset and span) that is irrelevant to the prediction of gas analyte concentration. Such time-varying changes do not necessarily have to be continuous/monotonic in time, but may also be discontinuous in time.

The pre-processed inputs from the sensor, the analyzer(s) and other available sources may include undesirable effects from hysteresis or drift in the measurements. Hysteresis and drift are commonly observed in chemical sensors, and they might be present in other data sources' inputs. Such effects in the sensor and auxiliary data inputs must be reduced in order for the sensor to maintain effective performance over long periods of time, and any such effects in the analyzer data must be reduced in order to develop effective algorithms for the sensor device. Therefore, drift and/or hysteresis correction procedures A12, A13 and A18 are often needed for all three data sources.

(i) Drift Correction—Background

Drift is a temporal change of a metrological characteristic of a measuring instrument. Such changes in gas sensing materials are typically irrelevant for predicting gas component concentrations, and often hinder the ability to develop an algorithm that can perform effectively over long periods of time. Drift can develop in a sensor when the sensor properties change over time due to component aging.

Significant work has been performed on drift-correction methods for sensor data. Most of this work applies to qualitative sensing applications only, where only a qualitative assessment or classification of the sample is required. Furthermore, most of the previous work that was applied to quantitative applications relies upon periodic measurement of a reference gas. Other methods have been proposed that do not require a reference gas, but these either require extensive on-line data processing, or an accurate long-term model of the drift behavior of the sensing materials. However, this prior work fails to address solutions to hysteresis and drift proposed by the present invention, where quantitative analysis is needed, a reference gas is not a practical possibility, the possibility of developing an accurate long-term drift model is unlikely, and the computing power of the on-board signal processing electronics is limited.

(ii) Drift Correction—Present Invention

The present invention utilizes application-specific drift correction methods that are specifically designed for the applications of the chemical sensors of the present invention. Such methods can employ input data from the sensor device, as well as any other on-line data that is available from the engine. During real-time operation, these inputs may be current inputs, inputs received before the current time, or a combination of these. They may also be time-derivatives of such current and historical data. The drift correction method may be fixed in time, or adaptive (time-varying) based upon more recent inputs from the sensor or auxiliary data. Furthermore, it may be executed at varying frequencies, based upon the nature of the application. It may involve a simple offset adjustment of a sensing element's response, a span adjustment of the response, or both. A separate drift correction method may be applied to each sensing element in the sensor array individually, or a single drift correction method may be applied to all sensing elements. Such a drift correction may use special in-engine sampling protocols that generate a sufficiently reproducible reference gas state. One method of creating a reproducible reference state consists of increasing the temperature of the sensor array, measuring lambda (i.e., the air-to-fuel ratio) in the environment around the sensor array, and scaling the resistances to the known reference resistance at that lambda and temperature. Another correction method might utilize specially engineered reference sensing materials that respond primarily to factors that cause drift, but respond minimally to changes in gas component concentrations. The drift correction method may be a separate step in the algorithm-building procedure as shown in FIG. 16, or it may be integrated with other steps in the procedure, such as the model generation or data preprocessing steps.

Selection of the appropriate drift correction method for a given application depends upon several considerations. Specifically, the selection depends upon the understanding of hysteresis and drift for the materials in the chemical sensors of the present invention. This involves characterizing the "functionality" of drift in the materials making up the chemical sensors, understanding the surface chemistry phenomena that lead to hysteresis and drift, discovering the effects of certain gases on hysteresis and drift in the materials making up the chemical sensors, and optimizing the material composition and microstructure to minimize hysteresis and drift effects. For example, in one application, it might be found through experimentation that drift has both a continuous monotonic component that is correlated to time, and a non-continuous ("structured") component that depends on specific variables in the sensing environment and the engine conditions.

Selection also depends upon materials and microstructure development. This is based upon previous work and targeted experimentation on the materials making up the chemical sensors, including optimization of material bulk chemistry, bulk microstructure, and surface functionality. For example, specific sensing materials may be chosen based not only on their sensitivities to the gas analytes of interest during such targeted experimentation, but also based on their drift characteristics, or the predictability of their drift characteristics, using sensor and auxiliary data that will be accessible during normal operation of the sensor in an engine.

Selection further depends upon the ability to generate reference sample states through in-engine referencing protocols. Reference gases may be used to monitor drift effects caused by longer-term changes in the sensor materials (e.g., adhesion, erosion, etc.). This requires some understanding of material-based sources of drift in the chemical sensors of the present invention. For example, in some applications, a reference sample state could be periodically generated by thermal, electrical, or magnetic excitation of the surfaces of the sensing elements. Also, for applications where periodic cycles in gas constituent concentrations are experienced, it might be possible to use the exhaust gas sample state during a fixed time during each cycle as a reference state.

The drift correction method might also require the development of reference materials. This involves monitoring the short-time-scale gas composition events that can result in sensor hysteresis and drift, which requires an understanding of the environmental sources of hysteresis and drift in the chemical sensors. Preferably the materials making up the chemical sensors would have a minimum response to analyte gases, but a maximum response to factors that cause hysteresis and drift. For example, if it is known that drift depends on certain environmental conditions of the exhaust gas, a specific sensing material could be developed that responds primarily to changes in these conditions, and responds minimally to changes in the analyte gas concentration. Such a material would enable the reduction of drift effects in the sensor responses during normal operation.

(iii) Drift Correction—Example

Figure 17A:
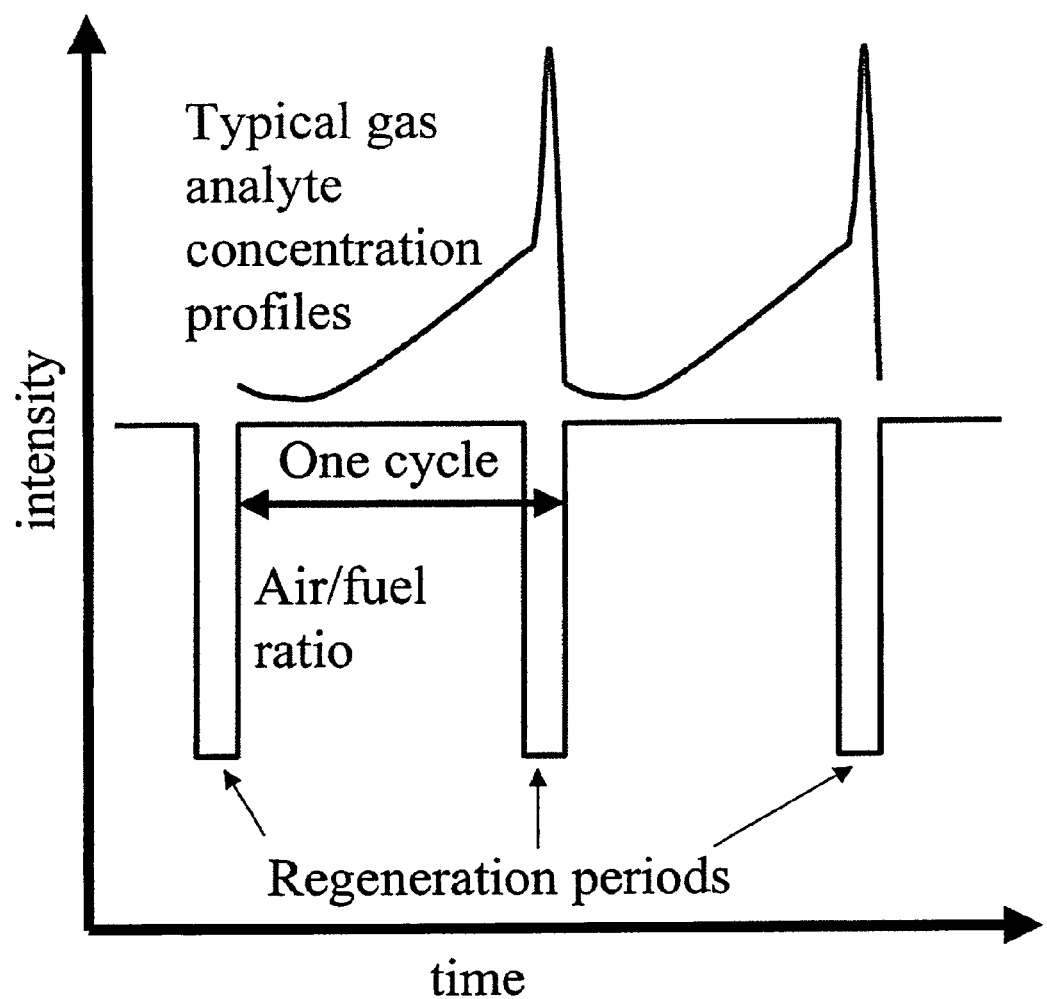
FIG. 17A is a graph showing the cyclical nature of exhaust gas concentrations in a gasoline direct injection (GDI) engine.

An example of an application-specific drift correction method is described below. The example was developed for use in sensing applications on a GDI (Gasoline Direct Injection) automotive engine. The normal operation of a GDI engine involves periodic regeneration/cleaning of a $NO_x$ storage catalyst by intermittently dropping the air/fuel ratio to produce a very rich-burning fuel in the engine feed gas mixture. This results in a cyclical pattern in the gas component concentrations in the exhaust, as illustrated in FIG. 17A.

EXAMPLE

Adaptive Drift Correction Background and Setup

This drift correction method applies both an offset (baseline response) and the span (sensitivity) correction that is specific to each sensing element in the array. The values of the offset and span correction factors are periodically updated at a specified point in time during each cycle of the GDI engine (hereby referred to as the "update time"). The update time for a given GDI cycle typically occurs shortly after the engine transitions from the rich regeneration state to the lean operating state. The execution of this drift correction method is illustrated in FIG. 17B to aid in its explanation. The optimal update time can be determined through analysis of data obtained from either a special experiment that is targeted towards determining this optimal time, or from a test of the sensor in an operating GDI engine. The time delay that is used to determine the update time for each cycle may be fixed for all sensing elements in the array, or it may be different for each of the sensing elements. Furthermore, it may be fixed over time, or it may vary over time. In the case of a fixed time delay, this optimal delay time may be calculated using sensor data, analyzer data, and auxiliary data obtained from the special experiment or an engine test. In the case of a time-varying (or adaptive) time delay, this time delay will also be adjusted using real-time sensor or auxiliary data.

During the update time for each cycle, the new values of the offset and span correction factors that are to be applied to the sensor responses are calculated by applying sensor-element-specific models (hereby referred to as "correction factor models") which use real-time and/or historical pre-processed sensor data A15 and drift-corrected auxiliary data A17 as inputs. The development of these correction factor models is described in the next paragraph.

Figure 17C:
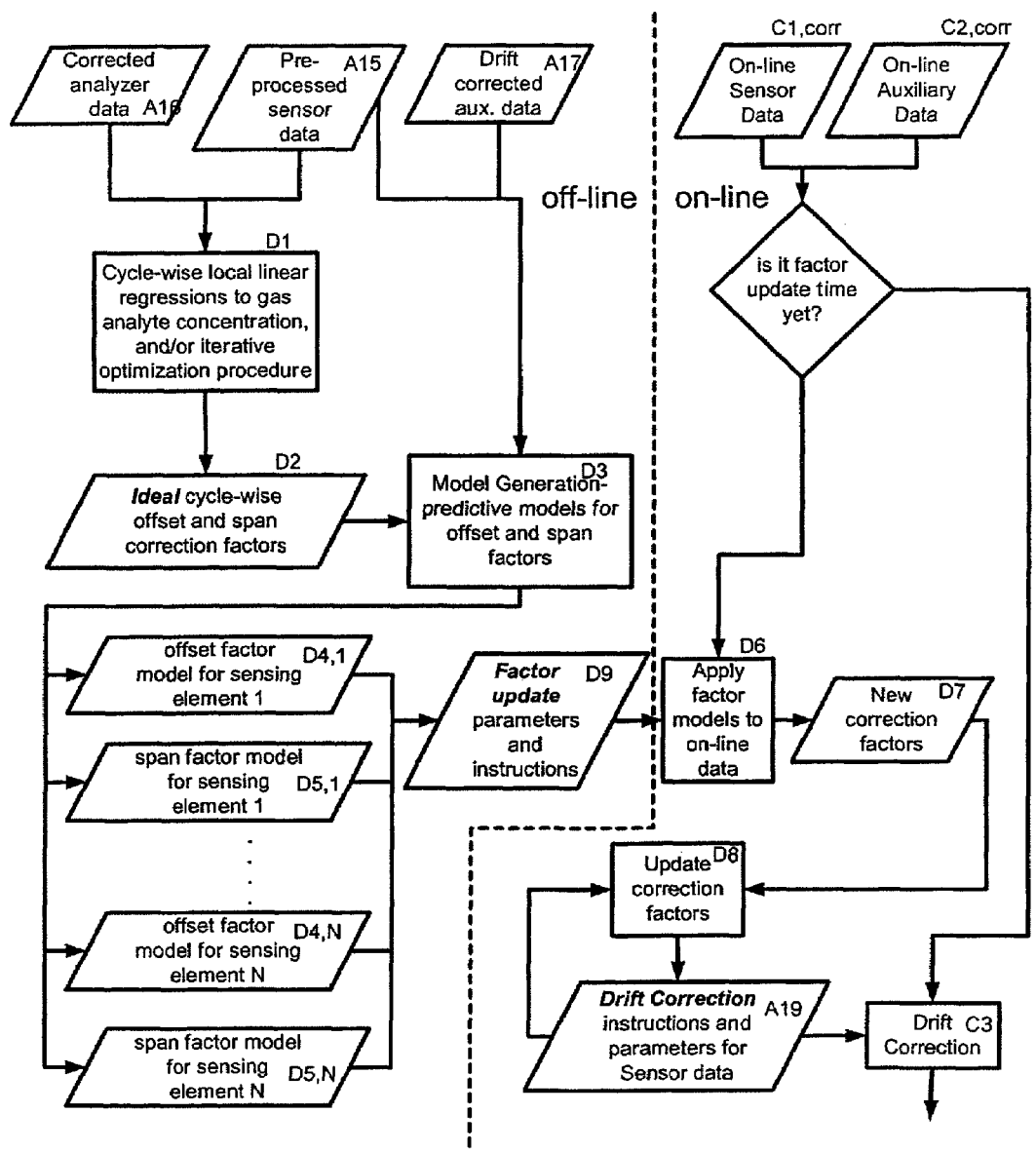
FIG. 17C is a flow chart showing the off-line process for development of the factor regression models used in the adaptive offset and span correction method, along with the execution of the correction method in the present invention.

The left side of the flow chart in FIG. 17C shows one such development process for the factor regression models used in the adaptive offset and span correction. These predictive models can be developed using data obtained from a special calibration experiment on the sensor, where not only sensor and engine data are available, but also data from an analyzer that independently measures the concentration of the analyte gas(es) of interest are available. First, the pre-processed sensor data A15 is processed further using a cycle-wise response zeroing procedure D1A, thus producing baseline-zeroed sensor data A15B. This response zeroing procedure is described as follows: the response of each sensor element at the update time is subtracted from all subsequent responses of that sensor element until the update time for the next GDI engine cycle. Then, the corrected analyzer data A16 and the baseline-zeroed sensor data A15B are used to determine the ideal offset and span factors for each sensing element, for each cycle. This process D1 can be done several ways, two of which are discussed below.

A series of local linear regressions of baseline-zeroed sensor element responses to the known analyte concentrations can be done for each sensor element, for each engine cycle.

$$g_j = b_{i,j} * s_{i,j} + a_{i,j} \quad (1)$$

where $g_j$ contains the analyte gas concentrations during cycle j, and $s_{i,j}$ contains the baseline-zeroed response of sensor element i during cycle j. This results in a set of regression slopes ($b_{i,j}$) and offsets ($a_{i,j}$), one for each sensor element/cycle combination. For each of the local linear regressions, the offset and the slope of the local regression line are the ideal offset and span adjustment factors, respectively, for that sensing element/cycle combination. As a result, a series of NC×NE sets of ideal offset and span adjustment factors D2 are obtained, where NC is the number of cycles in the calibration data, and NE is the number of sensing elements in the sensor array. As used herein, a GDI cycle is defined as the time interval between rich-to-lean engine transitions. The local linear regressions described above can use either all of data points obtained during a cycle, or any subset of the data points obtained during a cycle.

The ideal offset and span factors could also be determined using an iterative/recursive optimization procedure, in which different sets of values for these factors for each sensor element/cycle combination are tested, and then evaluated and adjusted based on the fit error of the regression model of sensor responses to analyte gas concentration(s) obtained from sensor data that is corrected using these factors. The ideal correction factors estimated by the method described in the previous paragraph (Equation 1) could be used as starting values for this recursive method.

Once the ideal offset and span correction factors D2 are calculated for a set of test data, a set of predictive models for estimating these correction factors (hereby referred to as "correction factor models") in real time can be developed (process D3). The inputs for these correction factor models may include, but are not limited to, pre-processed sensor data A15, baseline-zeroed sensor data A15B, and drift-corrected auxiliary data A17 that are collected at the update time, and/or such data that was collected before the update time. These correction factor models can be developed using a variety of tools, such as Linear Regression, Multiple Linear Regression, Projection to Latent Structures (PLS) (or other linear modeling methods), and Neural Networks (or other nonlinear modeling methods), which will be described in a later section. Once the set of NC×NE predictive models for the adaptive offset (D4) and span (D5) correction factors are calculated, their parameters and execution instructions D9 must be stored, so that they can be applied during real-time operation of the sensor device.

One obvious alternative to the Adaptive Drift Correction method as described above would be to bypass the baseline-zeroing step (D1A). For this alternative, only pre-processed sensor data A15 will be available to both estimate the ideal adaptive correction factors (process D1) and to generate the correction factor models (process D3).

Execution

The right side of the flow chart in FIG. 17C shows one possible execution scheme for the Adaptive Drift Correction method in a GDI engine in real-time, and the effects of this correction on sensor data obtained from a GDI engine are illustrated in FIG. 17B. In this specific case, baseline zeroing D6A is done to the sensor data first, and the baseline-zeroed sensor data D6C is used as input to the drift correction procedure C3. In addition, the update time is defined as a fixed time within each cycle for each sensing element, exactly $t_d$ after regeneration of the storage catalyst (see FIG. 17B). However, as mentioned earlier, the baseline zeroing step D6A can be bypassed. Furthermore, the update time need not be constant over time, nor be the same for each sensing element in the sensor array.

At any given time, the drift corrected sensor response is calculated according to the following equation:

$$s_{i,j,corr} = (s_{i,j} - a_{i,j}) / b_{i,j} \quad (2)$$

Where $s_{i,j}$ is the uncorrected response of sensing element i at a specified time during cycle j, $a_{i,j}$ is the currently valid offset correction factor for sensing element i during cycle j, and $b_{i,j}$ is the currently valid span correction factor for sensing element i during cycle j. At each specified update time within each cycle, this method first updates the response zeros to be used in the response zeroing process D6A. Then, it updates both the offset correction factor ($a_{i,j}$) and the span correction factor ($b_{i,j}$) for each sensing element in the sensor array. This correction factor update process D6 involves the application of the Correction Factor Models D9 (the development of which was discussed in the previous section) to the current on-line data. The on-line data that is applied to the Correction Factor Models was specifically defined during the development of the drift correction method (discussed in the previous section), and these may include, but are not limited to, pre-processed sensor data C1,corr, baseline-zeroed sensor data D6C, and drift-corrected auxiliary data C2,corr that are collected at the update time, and/or such data that was collected shortly before the update time. This correction factor update process D6 produces updated correction factors D7, which are then used to update the drift correction parameters A19.

The drift correction parameters A19 and response zeros D6D that were updated during the update time are applied to all subsequent sensor element responses until the update time for the next cycle, when these values are to be updated once again using the procedure described above.

EXAMPLE

Figure 22:
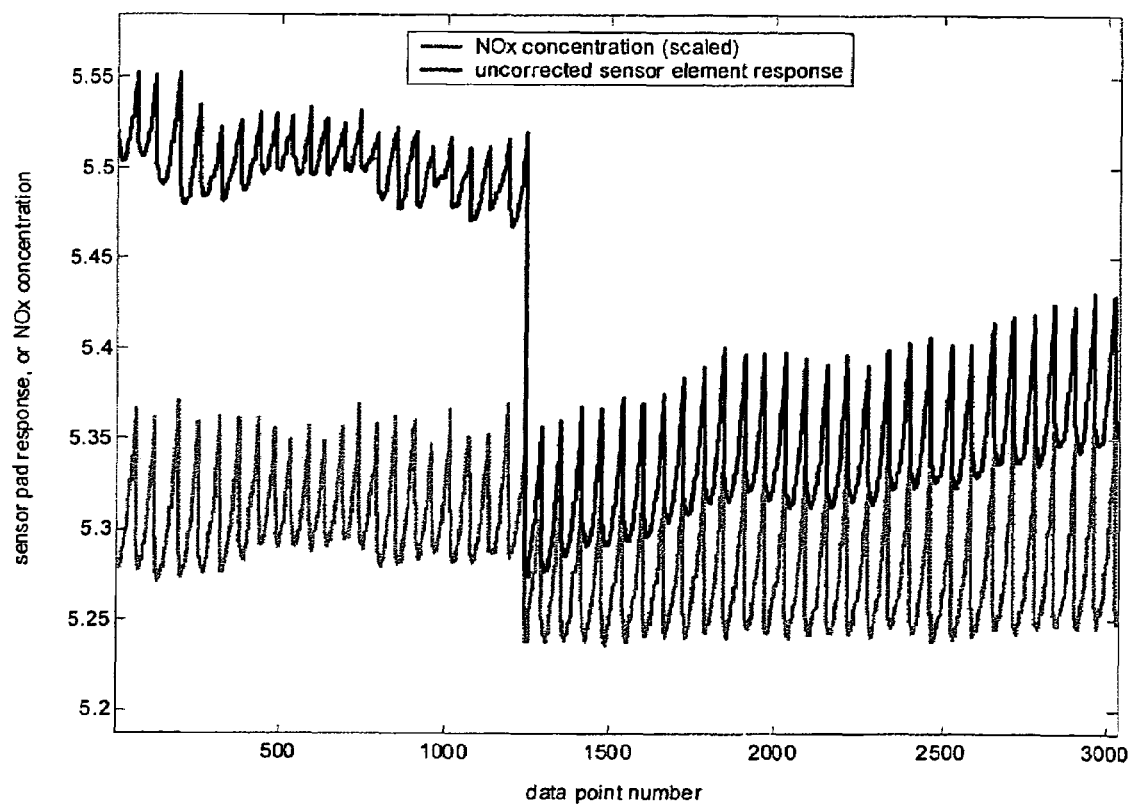
FIG. 22 is a graph showing a comparison of an uncorrected sensor element response and corresponding $NO_x$ concentration, for a test data set.

In this simplified example, the Adaptive Drift Correction method is applied to a single sensing element in a sensor array, so that it can be used to effectively predict $NO_x$ concentration in GDI engine exhaust. One set of data was used to build calibration models and a separate set of data was used to test the models. FIG. 22 compares the uncorrected sensor data and the $NO_x$ concentration, for the test set data.

Figure 23:
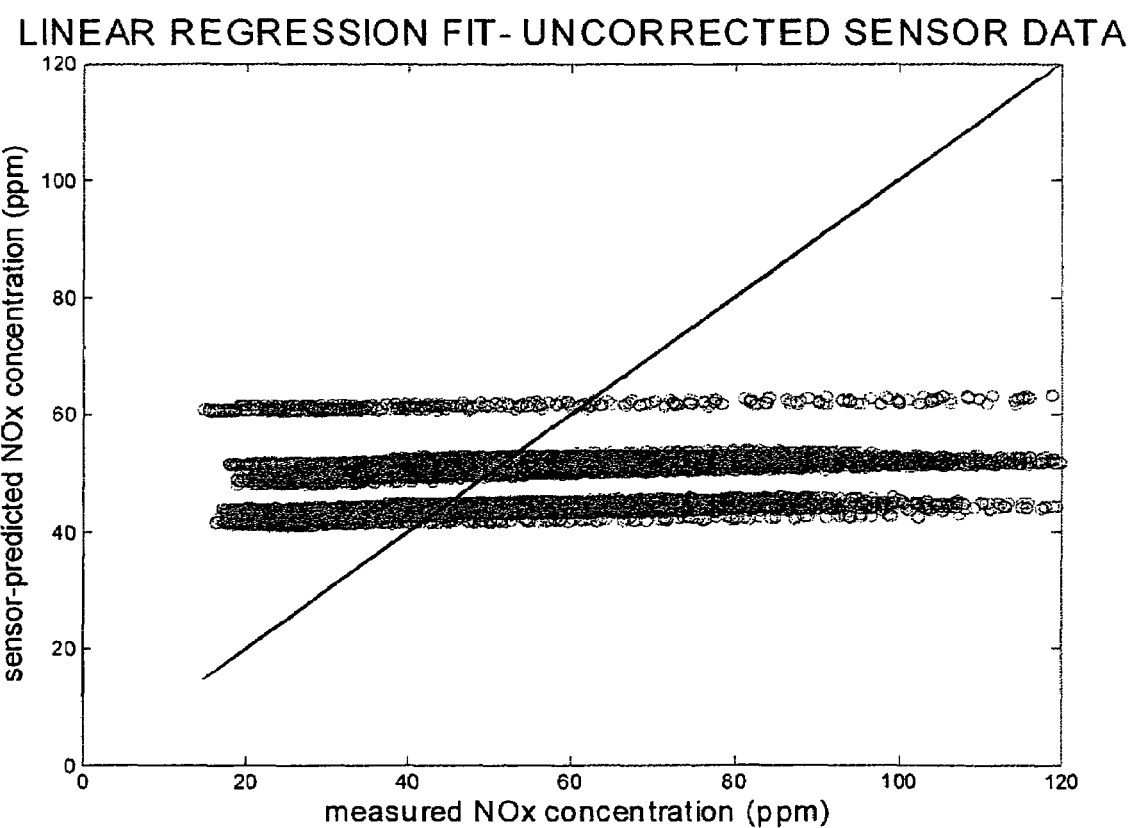
FIG. 23 is a graph showing sensor-predicted versus measured $NO_x$ concentration, for test set data, and a linear regression fit using a $NO_x$ calibration model developed from uncorrected sensor element responses.

Note that the sensor element responds well to short-term changes in the $NO_x$ concentration, but experiences drift and periodic changes in its baseline response during the course of the experiment. If uncorrected sensor data from the calibration data set is used to build a linear regression calibration model for $NO_x$, and then this model is applied to the test set data, the results shown in FIG. 23 are obtained. It is clear that the adaptive changes and long-term drift in sensor offset and span result in very poor prediction performance.

Figure 23B:
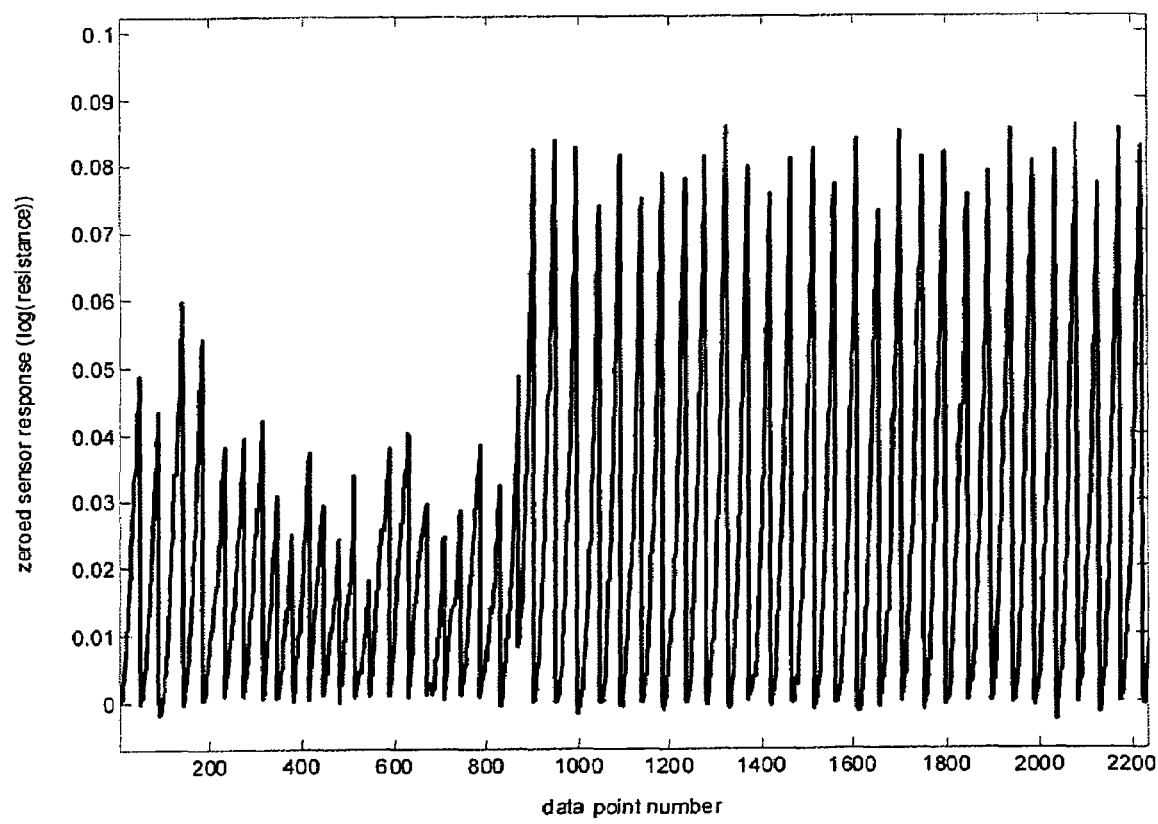
FIG. 23B is a graph showing zeroed sensor response versus data point number for test set data.

In this example, the correction method will be performed using baseline-zeroed sensor data. Furthermore, the update time will be defined as exactly 10 seconds after the rich-to-lean transition for each GDI cycle. FIG. 23B shows the sensor element's data after it has been baseline-zeroed using these update times.

Figure 24:
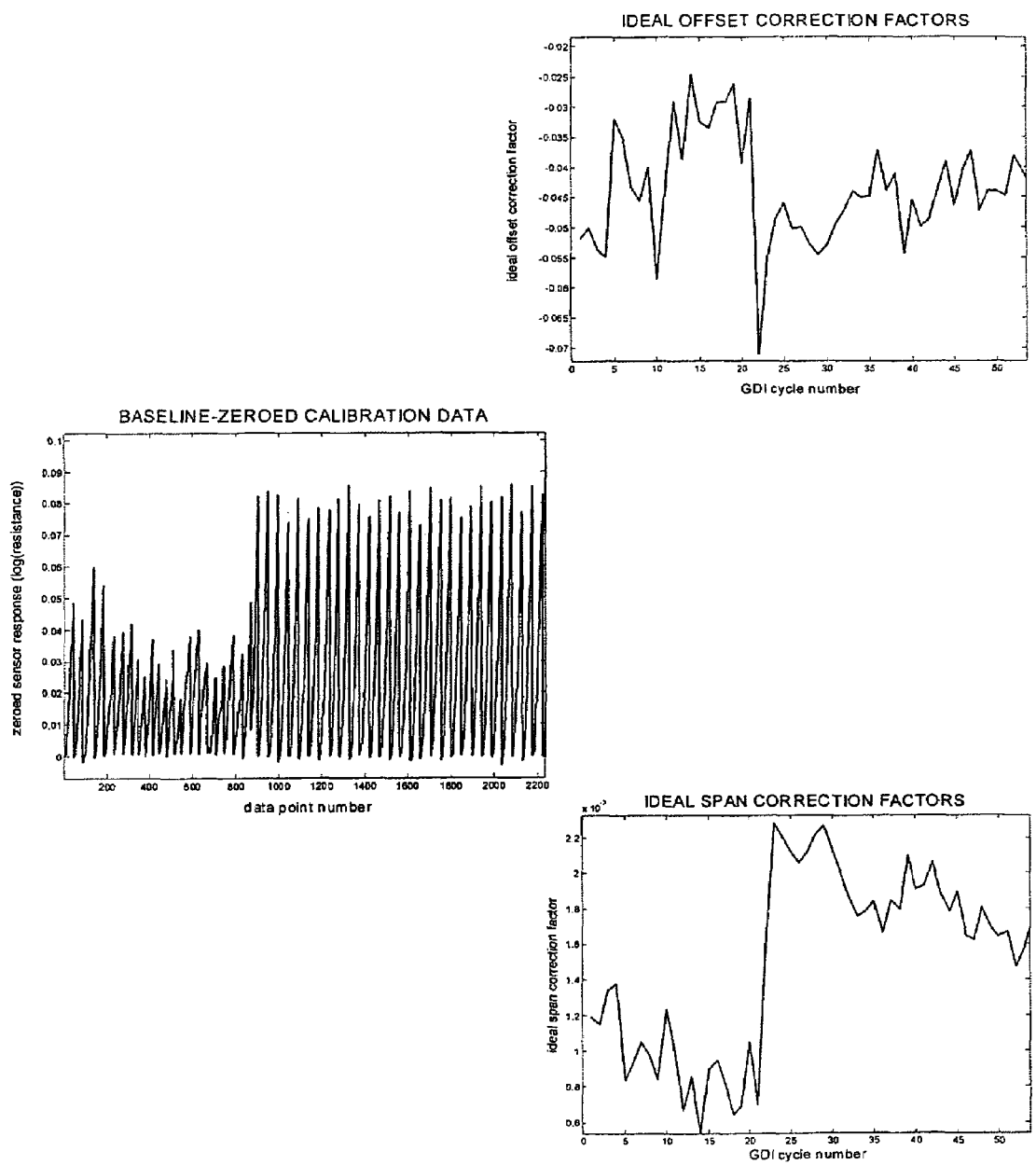
FIG. 24 are graphs showing the ideal adaptive offset and span correction factors determined for the calibration data, compared to baseline-zeroed calibration data.

Since there is only one sensing element being used in this example, there are a total of two correction factor models that need to be built: one for that sensing element's offset factor, and one for its span factor. The first step in building these models is to determine the ideal offset and span factors for each of the cycles in the calibration data set. In this example, this is done by performing a series of local linear regressions (one for each cycle) of the sensor responses to the measured $NO_x$ concentrations during the cycle, using corrected analyzer data A16 and baseline-zeroed sensor data A15B obtained from a calibration experiment. The resulting ideal offset and span factors for the calibration data are shown in FIG. 24, compared to the baseline-zeroed sensor data. For this example, the local linear regressions did not utilize all of the data points for each cycle, but rather a restricted set of data points, starting from the update time (10 seconds after the initiating rich-to-lean transition) to the time of the lean-to-rich transition.

Figure 25:
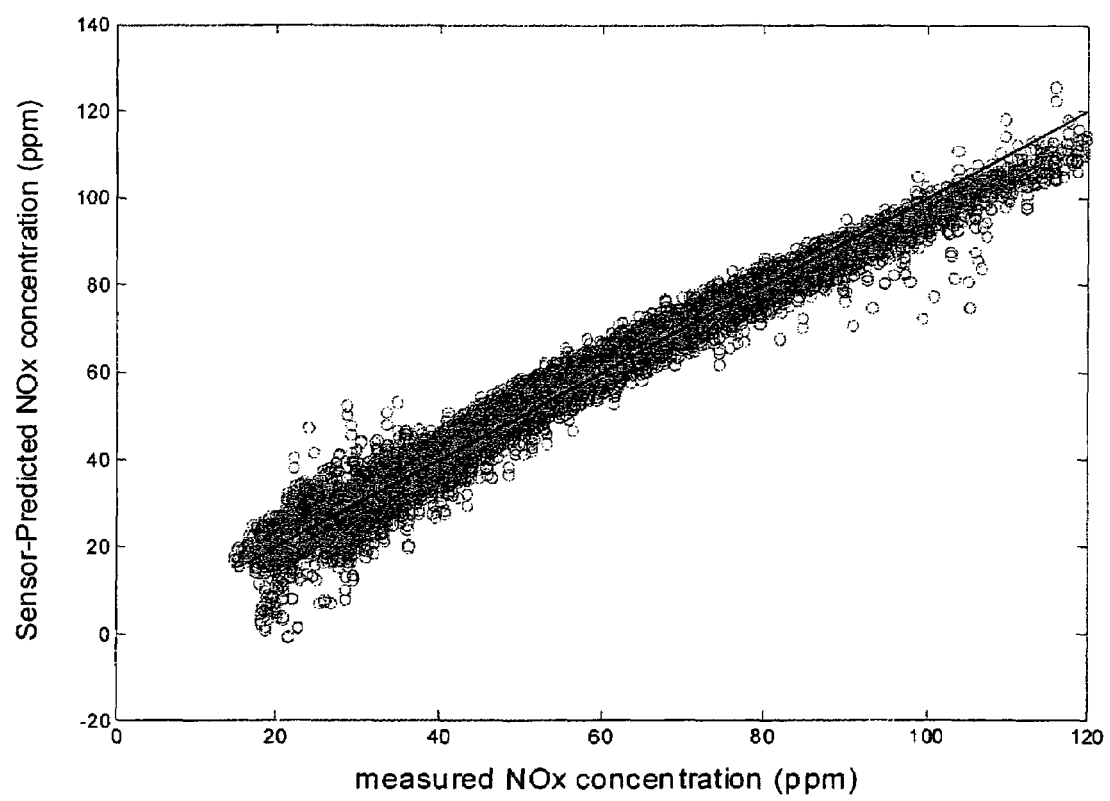
FIG. 25 is a graph showing the fit of a predictive $NO_x$ regression model built using linear regression on sensor element calibration data that was corrected using the ideal adaptive offset and span correction factors.

At this point, the calibration data can be corrected using the ideal correction factors determined above, and this corrected data can then be used to build a predictive $NO_x$ calibration. Since, in this example, there is only one sensing element used, this $NO_x$ calibration model is built using univariate linear regression. The resulting $NO_x$ calibration model is shown in FIG. 25. Note that the adaptive correction using the ideal correction factors results in a predictive $NO_x$ model that has a much better fit than the model built with uncorrected data (FIG. 23).

Once the ideal correction factors are obtained, one can then build predictive correction factor models for the offset and span correction factors. The predictor variables for such models can include any measurements that will be available to the sensor during normal operation of the engine, and can include: (1) data from any of the sensor elements in the device; (2) sensor chip temperature data, or other data taken by the sensor device; and (3) data from other sensors in the engine (lambda, RPM, torque, temperatures, airspeed, etc.). Furthermore, these predictor variables can include any of the above measurements taken at the update time as well as at some times shortly before the update time.

In this example, the two correction factor models were developed using Partial Least Squares (PLS) regression using a set of predictor variables from both the sensor and the engine. In this case, the sensor data that was considered as input to these models was restricted to baseline-zeroed sensor data, although this need not always be the case for all applications. The resulting correction factor models are shown in FIG. 26. These results clearly show that the adaptive offset and span correction factors of this sensing element for a given cycle can be reasonably estimated using information that is readily available in the engine.

Figure 28A:
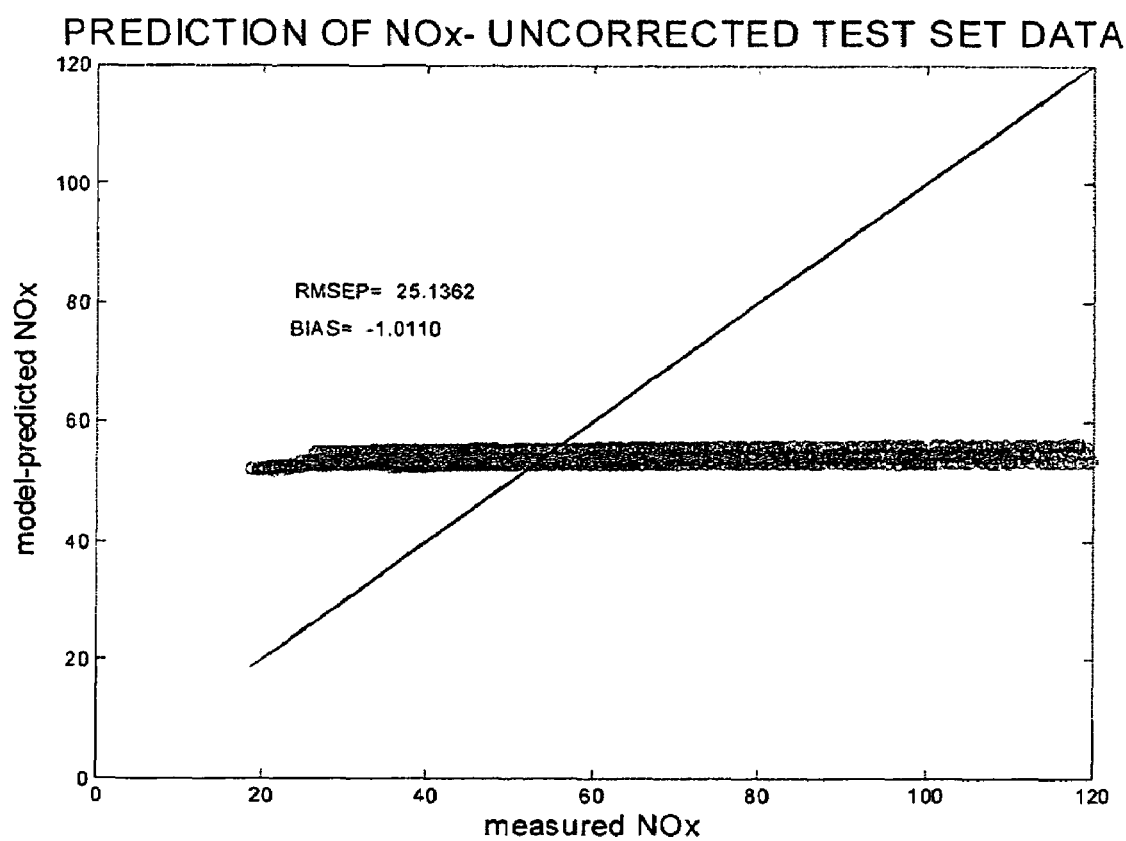
FIG. 28A is a graph showing the results of applying uncorrected test set data to the predictive $NO_x$ calibration model built using corrected calibration data.
Figure 28B:
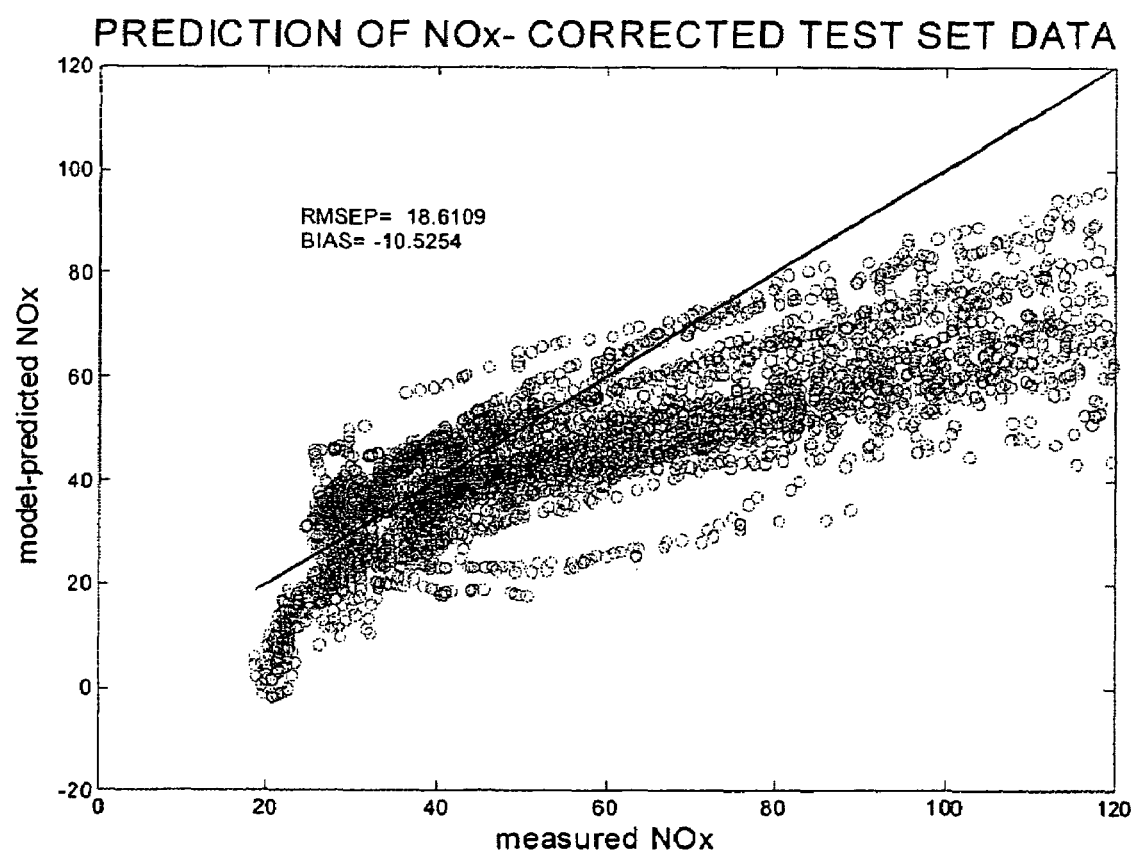
FIG. 28B is a graph showing the results of applying corrected test set data to the predictive $NO_x$ calibration model built using corrected calibration data.

Once the factor regression models have been developed, they can be applied to real-time sensor and engine data C1,corr and C2,corr at the appropriate update times in order to update the correction factors D7 for each cycle in this data. In this example, real-time drift correction is simulated by applying this method to a set of matching sensor and engine data that was not used to build the factor regression models (hereby referred to as the test set data). The sensor data in this test set before and after Adaptive Drift Correction are shown in FIG. 27. If the uncorrected sensor data is applied to the $NO_x$ calibration model built using uncorrected calibration data (FIG. 23 above), the results in the FIG. 28A are obtained. However, if the drift-corrected sensor data is applied to the $NO_x$ calibration model built using corrected calibration data (FIG. 25 above), the results in FIG. 28B are obtained. Note that the adaptive drift correction method results in greatly improved $NO_x$ prediction performance.

(d) Filtering (Orthogonalization)

The drift-corrected data may then be provided to another processing method, filtering or, more specifically, orthogonalization A20 (FIG. 16). A technique called orthogonal signal correction (OSC) and its variants comprise a class of techniques that are capable of removing (i.e., digitally filtering) effects in the sensor data that are irrelevant for calculating the concentrations of the analyte gas(es) of interest. To apply this class of methods, it is assumed that the origin of the unrelated effects in the signal input remains constant over the lifetime of the sensor. Parameters arising from the application of any such method(s) A21 must be stored for later use, when the sensors and associated measurement system are operating on-line to predict the concentration(s) or presence of specific analyte(s).

The corrected forms of data from the analyzer (A16), the sensor array (A22), and auxiliary data sources (A17) comprise the corrected data, which is used as input for the next process stage, model generation A23.

(e) Model Generation (Off-line Environment)

The corrected input data are then used to create one or more predictive models. Each model may be a univariate regression model, a multivariate regression model, a projection to latent structures model (PLS, or partial least squares) or another linear modeling method, a back-propagation neural network model or another nonlinear modeling method, or a combination of the above. Each of these types of modeling methods can generate multiple models when applied to the same corrected input data. Each of these models will be specific to the input data that was used to develop them, and thus to the specific materials used in the sensor array 100, and the type of engine exhaust system in which the sensor was placed in order to generate the input data for calibration (i.e., the sensor environment).

(i) Linear Regression

This model building method uses the corrected data from a single selected input (for example, a single sensing element in the sensor array, or a single variable in the auxiliary data), and performs a linear regression between this data and a matching set of known concentrations of the analyte of interest (for example, analyzer-measured $NO_x$ concentrations) according to the following equation:

$$y = bx + c \quad (1)$$

where x contains the data from the single input, and y contains the corresponding gas analyte concentration data. Given x and y, the model coefficients b and c are estimated using the Least Squares method. For univariate regression, these parameters (b and c) constitute the model parameters in parallelogram A24 of FIG. 16.

(ii) Multiple Linear Regression (MLR)

This model building method uses the corrected data from more than one input (for example, two or more sensing elements in the sensor array, or at least one sensing element and at least one input from the auxiliary data). The modeling method then performs multiple linear regression between these data inputs and the known concentrations of the gas analyte of interest (for example, $NO_x$), according to the following equation:

$$y = b_1 x_1 + b_2 x_2 + \ldots b_n x_n + c \quad (2)$$

where $x_1, x_2 \ldots x_n$ are the data from the multiple inputs 1, 2 ... n, and y contains the corresponding gas analyte concentrations. Given $x_1, x_2 \ldots x_n$ and y, the MLR model coefficients $b_1, b_2 \ldots b_n$ and c are calculated using the Multiple Least Squares method. For multiple linear regression, these model coefficients constitute the model parameters in parallelogram A24 of FIG. 16.

(iii) Projection to Latent Structures

This model building method requires the use of corrected data from more than one input (for example, two or more sensing elements in the sensor array, or at least one sensing element and at least one input from the auxiliary data). However, unlike the MLR method described above, the PLS method performs two different operations: (1) a compression of the original n input variables into a fewer number of latent variables, which are both completely independent of one another (and therefore account for any redundancies in the behaviors of the original n inputs) and explain most of the information contained in the original n variables; and (2) a multiple linear regression of these latent variables to the gas analyte concentration of interest. The final form of the PLS model is the same as that of an MLR model (equation 2), namely:

$$y = b_{1,PLS} x_1 + b_{2,PLS} x_2 + \ldots b_{n,PLS} x_n + c_{PLS} \quad (3)$$

However, the model coefficients $b_{1,PLS}, b_{2,PLS} \ldots b_{n,PLS}$ and $c_{PLS}$ are determined in a different manner, and thus can be quite different from those determined using MLR. For a PLS model, coefficients $b_{1,PLS}, b_{2,PLS} \ldots b_{n,PLS}$ and $c_{PLS}$ constitute the model parameters in parallelogram A24 of FIG. 16.

(iv) Neural Network Models

The neural network model building method requires the use of corrected data from more than one input (for example, two or more sensing elements in the sensor array, or at least one sensing element and at least one input from the auxiliary data). Unlike the modeling method discussed above, which results in models that can be executed through a simple linear mathematical operation (Equations 1-3), Neural Network models are typically executed through a series of more than one linear or non-linear operations.

Figure 18:
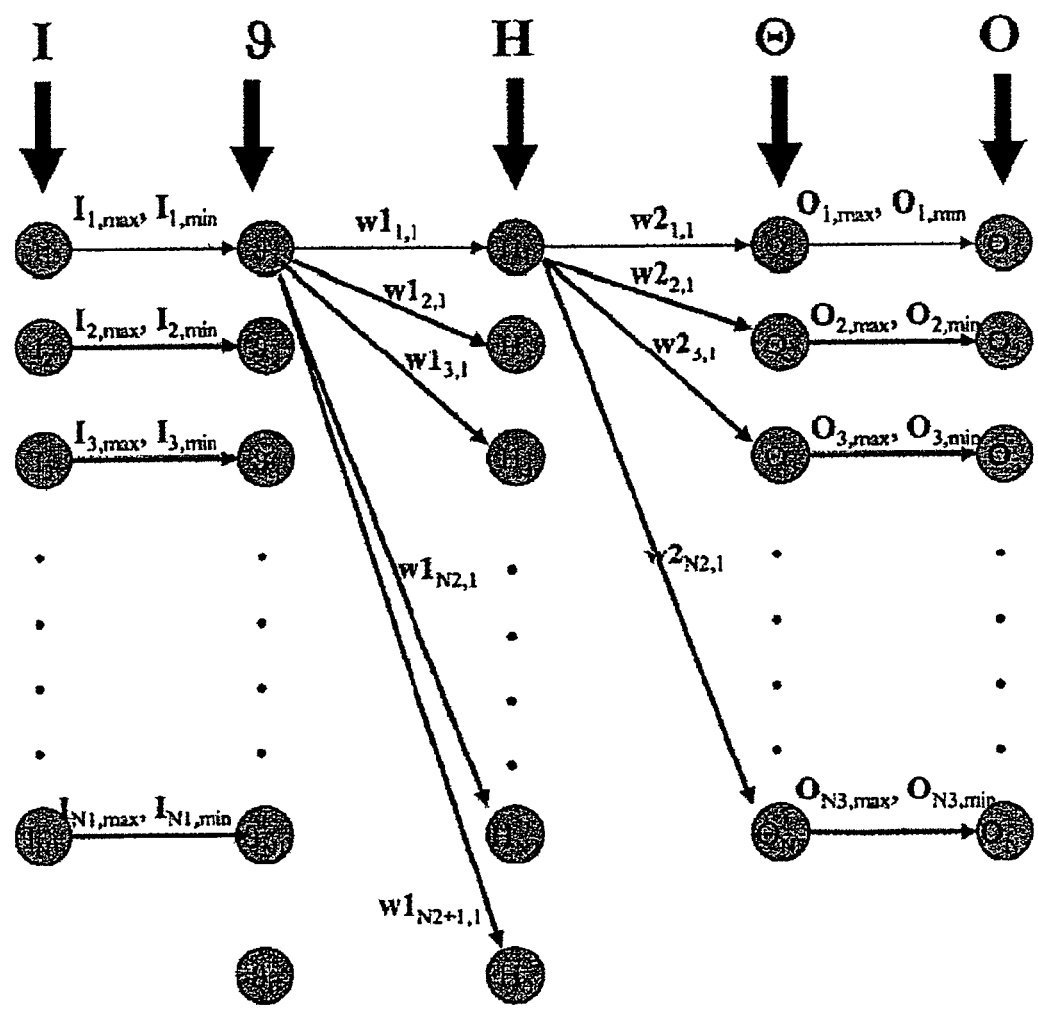
FIG. 18 is a chart showing a typical Neural Network model execution scheme capable of use with the present invention.

A typical Neural Network model execution scheme is shown in FIG. 18. The corrected input data is contained in the raw input vector I on the left side of FIG. 18, and the gas analyte concentration(s) of interest are contained in the raw output vector O, on the far right side of FIG. 18. The vector θ represents the scaled input vector, and the vector Θ represents the scaled output vector. The vector H, in the center of the figure, is called the "hidden" or "intermediate" vector. The coefficients that are used to translate the scaled inputs into the hidden vector are contained in the matrix w1, and the coefficients that are used to translate the hidden vector values to scaled outputs are contained in the matrix w2. The specific steps in the Neural Network model execution are described below.

Step 1: The linear scaling operation is performed on the corrected input vector, I, for each variable so that the scaled input vector, θ, has values between 0.1 and 0.9. For linear scaling, the scaled input vector, θ, is computed from the input vector, I, using the data minimum and maximum of each input variable:

$$\vartheta_i = \frac{\vartheta_0 0.8 * (I_i - I_{i,\min})}{(I_{i,\max} - I_{i,*\min})} + 0.1 \quad (4)$$

for $i = 0, 1, 2, \ldots N_1$, where $N_1$ is the number of inputs, $I_{i,min}$ and $I_{i,max}$, are the minimum and maximum values of the raw inputs for input variable i respectively, and $\theta_0$, an adjustment term for bias, is equal to 1. The column vector, θ, is comprised of $N_1+1$ elements (rows).

Step 2: Each value in the scaled input vector, θ, is then multiplied by a weight matrix, w1. The weight matrix, w1, computes the contribution of each separate input to each node in the network's hidden (intermediate) layer:

$$H_j = \left[1 + e^{-\left(\sum_{i=0}^{N_1}(w1_{j,i} * \vartheta_i)\right)}\right]^{-1} \quad (5)$$

for $j = 0, 1, 2, \ldots N_2$, where $N_2$ is the number of nodes in the hidden layer, and $w_{1,0}$, an adjustment term for bias, is equal to 1. The weight matrix, w1, is $N_2+1$ rows by $N_1+1$ columns in size, and the column vector, H, is comprised of $N_2+1$ elements (rows). The transformation between the scaled inputs and the hidden layer (Equation 5) is a non-linear transformation.

Step 3: Each value in the intermediate vector, H, is then multiplied by a weight matrix, w2. The matrix w2 is used to compute the contribution of each individual node in the hidden layer to each element of Θ, the network's scaled output vector:

$$\Theta_k = \left[1 + e^{-\left(\sum_{j=0}^{N_2}(w2_{k,j} * H_j)\right)}\right]^{-1} \quad (6)$$

for $k = 1, \ldots N_3$, where $N_3$ is the number of outputs and $w_{2,0}$, an adjustment term for bias, is equal to 1. The weight matrix, w2, is $N_3$ rows by $N_2+1$ columns in size, and the column vector, Θ, is comprised of $N_3$ elements (rows). The number of gas species for which concentrations must be computed determines the number of output units $N_3$. For example, in an application where only one gas analyte concentration output (for example, $NO_x$) is required, there is only one output unit ($N_3=1$). For an application where three gas analyte concentration outputs (for example, $NO_x$, oxygen and total hydrocarbons) are required, there are three output units ($N_3=3$). The transformation between the hidden layer nodes and the scaled outputs (Equation 6) is a non-linear transformation.

Step 4: To compute the raw output vector, O, from the scaled output vector, Θ, an inverse linear transformation is computed, using the data minimum and maximum values:

$$O_k = O_{k,\min} + \frac{(\Theta_k - 0.1) * (O_{k,\max} - O_{k,\min})}{0.8} \quad (7)$$

where $O_{k,min}$ and $O_{k,max}$ are the minimum and maximum values of the raw outputs for output variable k respectively. The contents of raw output vector, O, are related to the gases of interest and are in a form that will yield the concentrations when the appropriate inverse operations are applied to O in the post-processing step discussed below.

For a Neural Network model with one hidden vector, which is typical for many neural network applications, the model parameters are the maximum and minimum raw input values (vectors $I_{min}$ and $I_{max}$), the maximum and minimum raw output values (vectors $O_{min}$ and $O_{max}$), and the weight matrices w1 and w2. Although $I_{min}$, $I_{max}$, $O_{min}$ and $O_{max}$ are easily calculated from the raw input and output data, the calculation of the weight matrices w1 and w2 is more complicated. The present invention may utilize conventional methods, such as Back-Propagation and "Stiff" Back-Propagation, to calculate the weight matrices from raw input and raw output data. For a Neural Network model with one hidden vector, the parameters $I_{min}$, $I_{max}$, $O_{min}$, $O_{max}$, w1 and w2 constitute the model parameters in the parallelogram A24 in FIG. 16.

Figure 20:
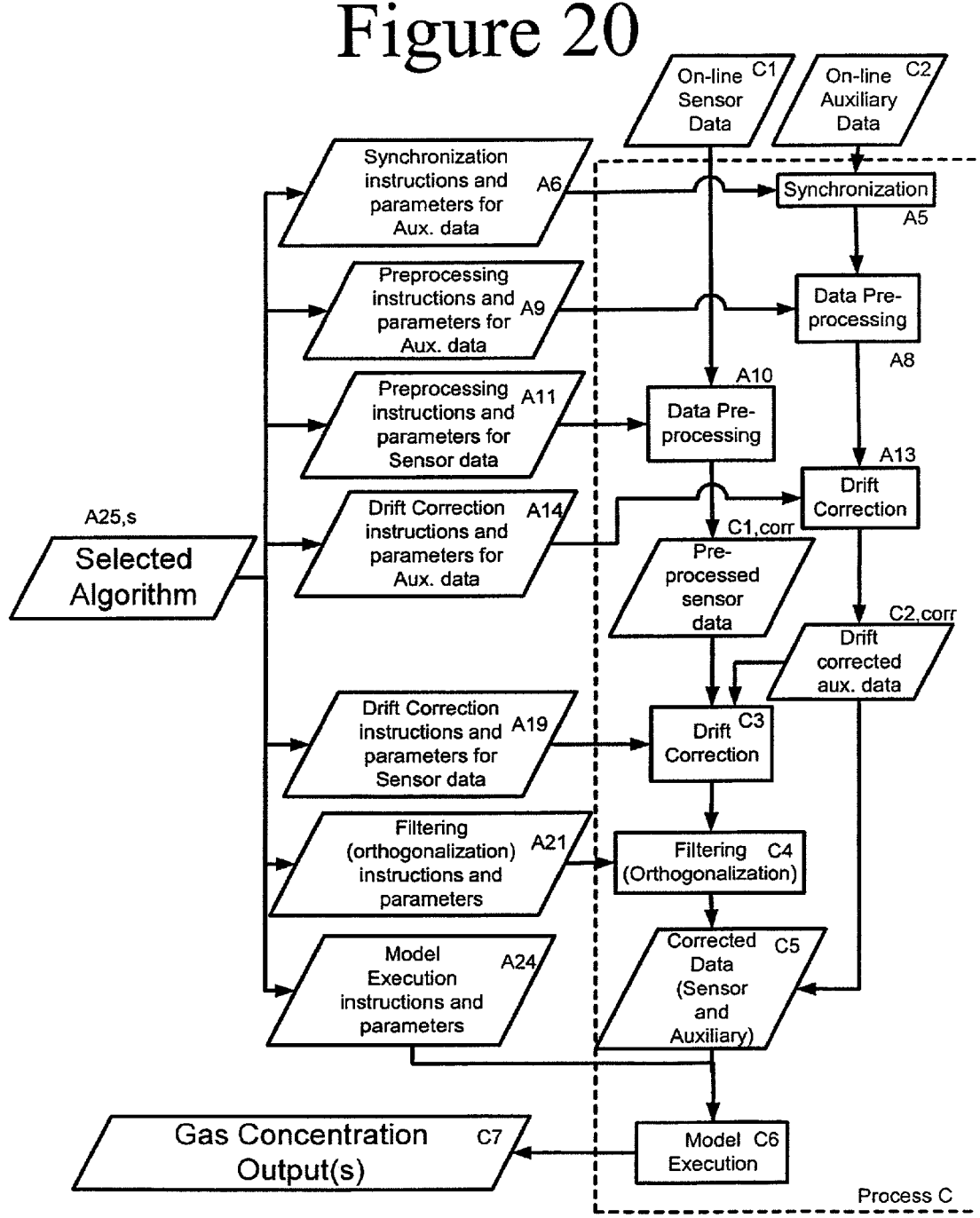
FIG. 20 is a flow chart showing the on-line execution of an algorithm of the present invention.

With regard to algorithm development, the sequence of steps illustrated in FIGS. 16 and 20, and described above, is only one example of a data processing sequence, and the steps may be executed in different sequences. For example, an algorithm could be developed in which filtering/orthogonalization (A20) is performed before drift correction (A12, A13, A18), or the auxiliary data could be pre-processed (A8) before synchronization (A5).

b. Algorithm Selection in the Off-line Environment

Algorithm selection may be done on-line (i.e., real-time, while the sensor is operating in an engine) or off-line. In this section, algorithm selection in the off-line environment is presented.

As used herein, the term "algorithm" is defined as a set of parameters and data processing instructions for data pre-processing, auxiliary data synchronization, drift correction, data filtering, and model execution (see parallelogram A25 in FIG. 16). For a given sensor device in a given engine exhaust application, several different algorithms may be prepared, each of which could use different sets of preprocessing, synchronization, drift correction, filtering and model execution elements, in a different chronological order.

Figure 19:
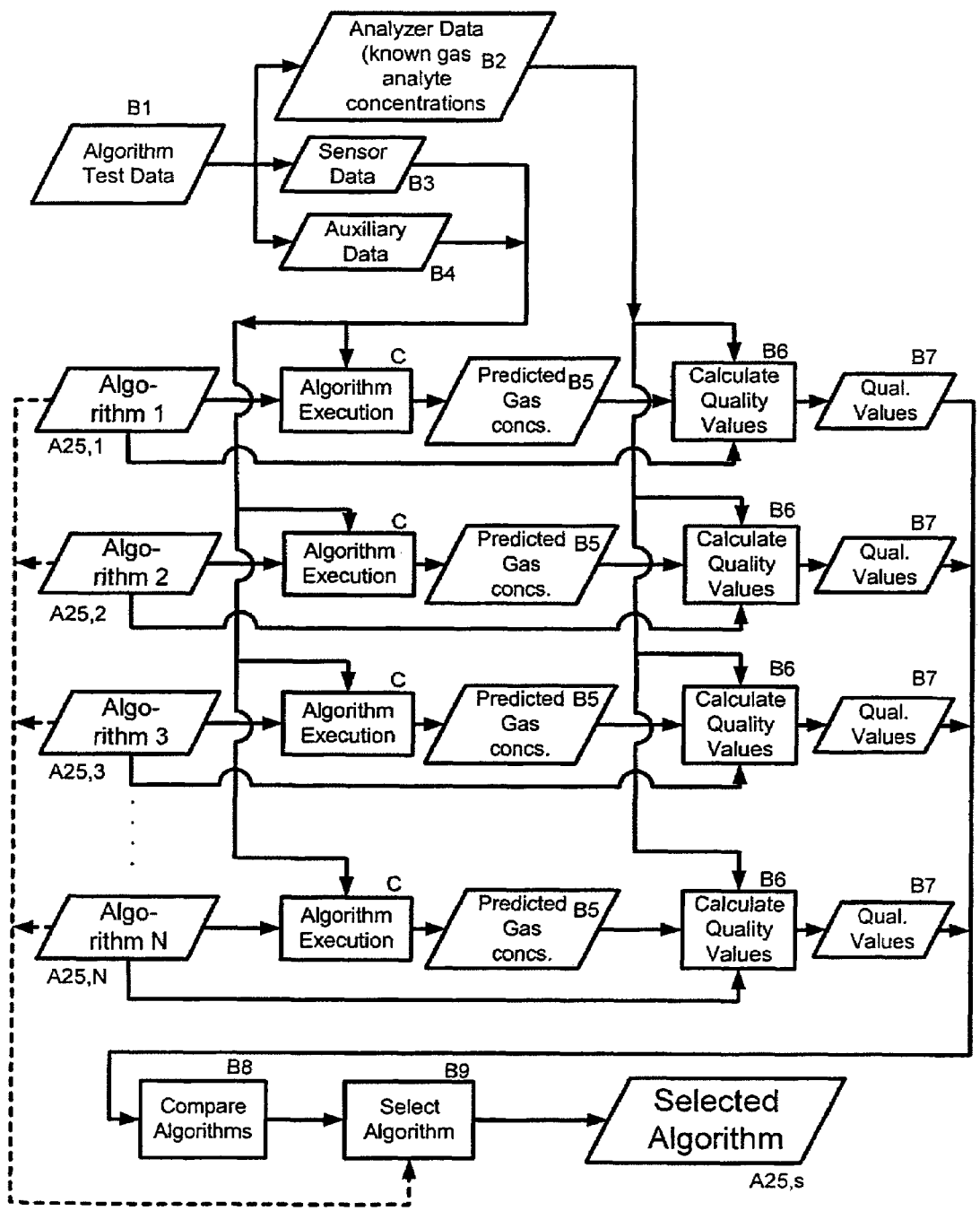
FIG. 19 is a flow chart showing the off-line algorithm selection process of the present invention.

Algorithms generated A25 by the previously-described method (as described in Section C.2.a) are sent to the algorithm selection process. FIG. 19 shows the substeps involved in the algorithm selection process. First, each algorithm candidate (A25,1, A25,2, . . . A25,N) is applied to a previously collected set of sensor and auxiliary data (B3 and B4) that also has a matching set of analyzer data B2 (which contains the known gas analyte concentrations). This previously-collected set of data is commonly referred to as the test data (B1). The detailed steps involved with the application of an algorithm to a set of new input data (process C) is summarized below and shown in FIG. 20. It is preferred that the test data not include any data that was used to generate any of the algorithm candidates (A25,1, A25,2, . . . , A25,N). The application of each algorithm candidate (A25,1, A25,2, . . . A25,N) to the test data (B1) results in a set of predicted gas analyte concentrations (B5) for each algorithm candidate.

Once the set of predicted gas analyte concentrations for each algorithm candidate B5 are obtained, they are combined with the known gas analyte concentrations B2, along with other information from the algorithm A25, to generate several different quality values, B7, that constitute criteria that are used to evaluate the expected effectiveness of each algorithm candidate. Three commonly used quality values, B7, for this purpose are described below, although these do not represent an exhaustive list.

(1) Root Mean Squared Error (RMSE)

A common criterion for comparing the effectiveness of different algorithms is the Root Mean Squared Error, or RMSE. This statistic is calculated according to the equation below:

$$RMSE = \sqrt{\frac{\sum_{i}^{N}(Y_{known} - Y_{predicted})}{N-1}} \quad (8)$$

where N is the number of observations (or samples) in the test data, $Y_{known}$ are the known gas analyte concentrations (from the analyzer data), and $Y_{predicted}$ are the gas analyte concentrations predicted by the algorithm. A high RMSE implies that the algorithm will produce a large error in its predicted gas analyte concentrations, while a low RMSE implies that it will produce less error in its predicted gas analyte concentrations.

When the test data is the same as the data used to generate the algorithm, the RMSE statistic is commonly called the RMSEC, or Root Mean Square Error of Calibration. Because the same data is used for building and testing the model in this case, the RMSEC statistic is an optimistic estimate of the algorithm's effectiveness.

When the test data were obtained independently from the data used to generate the algorithm (for example, collected at a different time, on a different engine, or in a different location), the RMSE statistic is commonly called the RMSEP, or Root Mean Square Error of Prediction. Because different data are used for building and testing the model in this case, the RMSEP is commonly considered to be a more realistic assessment of the algorithm's performance.

(2) Algorithm Complexity

A second criterion for algorithm candidates is the overall complexity of the algorithm. If all other criteria are equal, a less complex algorithm is desired over a more complex algorithm, because it is easier to execute, easier to maintain, and less sensitive to unforeseen disturbances in the sensor and auxiliary data during normal operation. This criterion is a more qualitative and is based on the number of data processing operations in the algorithm, the number of inputs used in the regression model, the number of latent vectors in a PLS model (or another linear model), or the number of hidden vectors in a Neural Network model (or another nonlinear model). For example, if two algorithms that both use a PLS regression model produce the same RMSE statistic when applied to the same set of test data, and they each use a different number of latent vectors, the model with the fewest number of latent vectors would be less complex and thus, more likely to be selected.

(3) Magnitude of the Model Regression Coefficients

When comparing different multiple linear regression (MLR) and PLS models, the magnitude of the model coefficients $b_1$, $b_2$ . . . $b_n$ reflects the sensitivity of the model to unforeseen disturbances, or any other deviation from the conditions used to generate the algorithm, during normal operation. Therefore, it is desired that the magnitude of these coefficients for such models be as low as possible. One statistic that could be used to express the magnitude of the coefficients is the sum of squares of the coefficients (SSC):

$$SSC = b_1^2 + b_2^2 + \ldots b_n^2 \quad (9)$$

If all other criteria are equal, the model with the lowest SSC is considered to be the most favorable.

Once the quality values, B7, are calculated for each algorithm candidate, they are compared to one another (B8) to enable an overall quality assessment of each algorithm candidate. Based on these quality assessments, a single algorithm may be selected from the N candidates (A25,1, A25,2, . . .

A25,N), which becomes the selected algorithm (A25,s) for predicting the concentrations of analyte gas(es). Alternatively, the invention may provide sufficient computing capacity so that more than one predictive model may be evaluated in real time and the respective algorithm candidates' quality values, B7, may be used to compute a weighted estimate for the concentration of analyte gas(es).

C. Algorithm Execution (On-Line Environment)

The selected algorithm is then provided to the algorithm execution step C. This step represents the operation of the algorithm in real-time, while the sensor is installed in an engine exhaust system. FIG. 20 shows the substeps involved in the algorithm execution process C. As can be seen from FIG. 20, this step is simply a series of execution steps that were previously defined in the selected algorithm A25,s during its algorithm development (FIG. 16), applied to a matching set of sensor (C1) and auxiliary data (C2) obtained from an engine at a particular instance in time. The parameters and instructions for each of these execution steps must be identical to those defined in the selected algorithm (A6, A9, A11, A14, A19, A21, A24), and the sequence of steps during algorithm execution must match that of the selected algorithm A25,s.

The data inputs for the algorithm execution process (C) are the on-line sensor data (C1) and the on-line auxiliary data (C2). These data are similar to those used to develop the algorithm (A2 and A3) except that they are collected in real-time during actual operation of the sensor device in an engine. The sensor data C1 is the data collected from the sensing elements in the array at any given point in time. The auxiliary data C2 is the data obtained from other parts of the combustion system, such as the engine control unit (ECU) or other data sources located on the vehicle. Such data can include, but is not limited to, the fuel-to-air ratio, the engine speed in revolutions per minute, the engine torque, the engine power, the engine inlet air temperature, and the exhaust gas temperature.

First, the auxiliary data (if it is being used in the algorithm) must be synchronized A5 according to the stored parameters and instructions in the algorithm (A6), preprocessed A8 according to the stored parameters and instructions in the algorithm (A9), and drift-corrected according to the stored parameters and instructions in the algorithm (A14). The sensor data must also be preprocessed according to the stored parameters and instructions in the algorithm (A11). This preprocessing might include temperature compensation, as discussed below. Then, the pre-processed sensor data C1,corr is combined with the drift-corrected auxiliary data C2,corr to perform drift correction C3 on the sensor data according to the stored parameters and instructions in the algorithm (A19). Such drift compensation might be the Adaptive Drift Correction Method described above. Then, if necessary, the sensor data is filtered/orthogonalized according to the stored parameters and instructions in the algorithm (A21). Finally, the calibration model A24 is executed (C6) using the corrected sensor and auxiliary data C5 as inputs, to generate gas analyte concentration(s) C7. The gas analyte concentration information C7 may then be utilized to adjust a parameter in the system generating the multi-component gas system under analysis.

The temperature variations on a sensor pad may correlate with resistance fluctuations. If these fluctuations are large, they may corrupt the predictive ability of the algorithm, if the algorithm is built on resistance data from a narrow temperature range. Compensating for the variations in resistances due to temperature would produce better predictions from this type of model. This can be done in several ways. In one method, a past certain length of time is reviewed, and the past variations in temperature are used to predict the resistance. Thus, models of the following form are sought:

$$R - \bar{R} = k(T - \bar{T})$$

where $\bar{R}$ and $\bar{T}$ are the mean resistance and temperature over that range of data in the past length of time. Using the least squares technique, k may then be found. The term $k(T-\bar{T})$ defines the variation in resistance due to temperature. The corrected R can be obtained by subtracting $k(T-\bar{T})$ from $\bar{R}$. A problem arises if $\bar{T}$ is not the preset temperature of the sensors which generated the data. The baseline of the data becomes corrupted and one problem is replaced with another. The baseline can be restored by adding back into the resistance, $k(T_s-\bar{T})$, where $T_s$ is the setpoint or the desired temperature for the sensor pad. This will correct the fluctuations in temperature with minimal corruption to the baseline.

The technique can be modified so that the value of k is adaptively found with an exponential forgetting time. To do this, the model needs to be modified slightly to give $R(t)=\alpha T(t)+\beta$, with R being the resistance and T the temperature at time t.

If $\hat{\theta}(t)$ is the estimate of the transpose vector $[\alpha \ \beta]^T$ at the time t, and the previous estimate is $\theta$ (t−1), then the new estimate can be evaluated by:

$$\theta\ (t) = \theta\ (t-1) + K(t)(R(t) - \phi^T(t)\theta\ (t-1)) \text{ where } \phi(t) = [T(t) 1].$$

The gain factor $K(t)$ is $K(t) = P(t)\phi(t) = P(t-1)\phi(t)(\lambda I - \phi^T(t)P(t-1\phi(t))^{-1}$ where $P(t)$ is the variance-covariance of temperature, I is the identity matrix, $\lambda$ is the forgetting factor, and $P(t) = (I - K(t)\phi^T(t))P(t-1)/\lambda$. There are other variations of this theme that could be applied, such as the projection algorithm that simplify somewhat the computation involved.

The vector $\hat{\theta}(t)$ can be used to estimate the contribution of temperature on resistance. The correction for not being at the right mean can then be modified as before.

This technique can be used on-line to provide a mechanism for correcting the resistance measurements for variations resulting from temperature. This is critical if the temperature of the sensor device is outside the range of the temperatures used when the calibration data was taken for developing the algorithm. This could occur because the controller on the chip is not maintaining a stable temperature, when ambient temperature is below the device set temperature, or when the ambient temperature is above the device set temperature.

d. Real-Time Quality Diagnostic for Chemical Sensor Array

Figure 21:
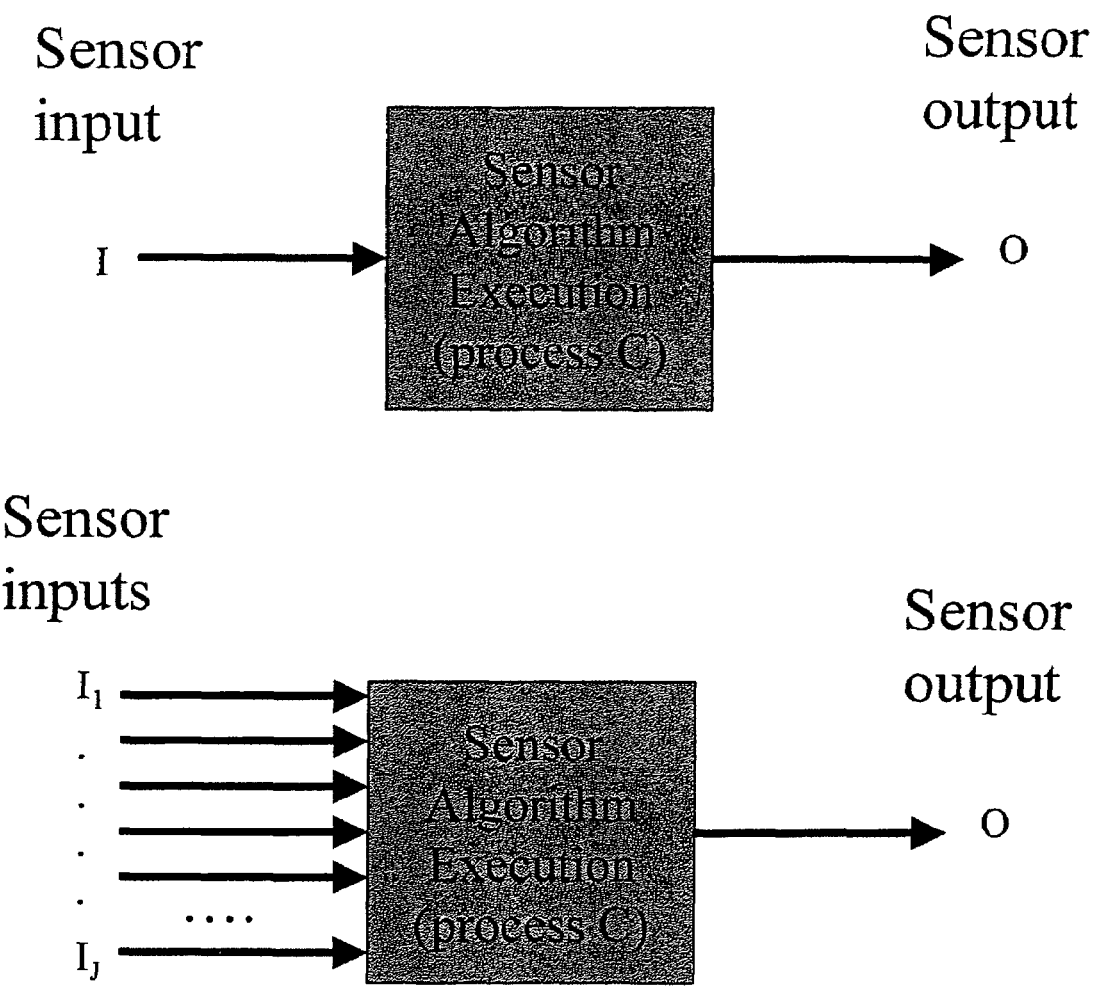
FIG. 21 is a greatly simplified schematic showing an algorithm execution scheme for a single sensing element (top) and for an array of sensing elements (bottom)

The present invention provides a real-time signal quality assessment diagnostic statistic for a sensor array device, which may provide an alarm at those times when the sensor is operating in a sampling space for which it was not calibrated, and would therefore be prone to generating inaccurate estimates of the analyte gas(es) concentration(s). A greatly simplified example of signal processing schemes for a sensor with a single sensing element and a sensor array device are illustrated in FIG. 21.

A sensor array of n sensing elements produces n inputs. These inputs are then operated on by a series of mathematical operations (the selected sensor algorithm) to generate a quantitative sensor output (such as NOx concentration, or NH3 concentration) (see bottom example in FIG. 21).

(1) Background

For a sensor in which a single sensing element is used to generate a response (top of FIG. 21), this single sensing element must be very selective for the sample constituent of interest (e.g., $NO_x$). This leads to a very simple calibration procedure and a very simple algorithm:

$$\text{output} = \text{constant} * \text{input} + \text{offset} \quad (1)$$

With such a simple algorithm, it is easy to determine whether the sensor is operating in a condition in which it was not calibrated (hereinafter referred to as an "outlier condition"): simply determine whether the sensor input or the output at the current time is within the range of sensor outputs that were generated during calibration. A good example is a pH sensor based on a single electrode that is certified to be accurate from pH 4 to pH 10. If a reported pH is outside this range, then the sensor reading is suspect. It is not even necessary to know whether the sensor input (the pH electrode current or potential measurement) is within the range of inputs used for calibration, because, if the sensor output is within range, then the direct input/output relationship implies that the sensor input is also within range.

The situation is much different if an array of sensor inputs is used to generate an output. Such a situation becomes necessary if none of the individual sensing elements have exclusive sensitivity to individual sample constituents (and cross-sensitivities exist). In this case, a more elaborate calibration procedure must be done in order to generate a more complex algorithm. This has two immediate consequences: (1) the algorithm is more likely to generate erroneous outputs during outlier conditions, thus making the detection of such outlier conditions more critical; and (2) the detection of such outlier conditions during sensor operation cannot be done by just monitoring for "out of range" values of the sensor output, and cannot even be done by monitoring for "out of range" conditions of each of the J sensor inputs in FIG. 21. Instead, it is necessary to build a mathematical model that describes the sensor input values obtained during sensor calibration conditions, and apply this model in real-time during sensor operation in order to determine whether such a potentially misleading outlier condition exists.

(2) Overview of the Sensor Quality Factor

Once the calibration data for a sensor device A2 is collected, a Quality Factor model of the sensor array element responses obtained during calibration is developed, using, for example, Principal Components Analysis (PCA). Parameters from this Quality Factor model may then be made resident on the on-board sensor electronics, and may be mathematically applied to the sensor array inputs as they are collected in real time. Subsequent model outputs from the predictive, qualitative model are then used to calculate a Quality Factor, which indicates whether the set of sensor inputs at that time are valid for safe application of the quantitative algorithm. In the case of PCA, the model outputs that are most useful for calculating the Quality Factor are called residual and leverage. The outcome of the Quality Factor computations can then trigger several possible actions, such as avoidance of sending the current input data to the quantitative algorithm to generate an output, an alarm on the control system in which the sensor is used, or collection and storage of sensor and other data to be later used for sensor re-calibration.

(3) Mathematical Details of the Sensor Quality Factor

Figure 29:
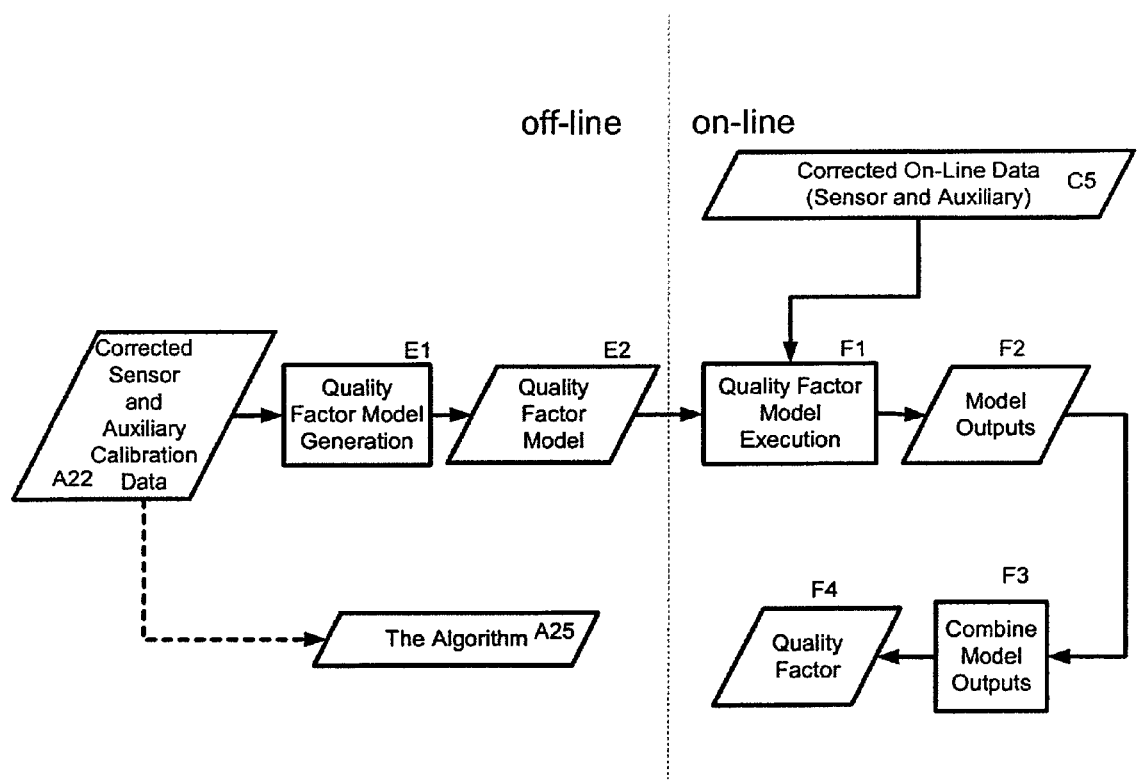
FIG. 29 is a flow chart showing the development process for a quality factor model in the off-line environment, along with its application in the on-line environment.

FIG. 29 illustrates the development of the Quality Factor model, as well as its execution in real time. The Quality Factor model is developed using sensor array data collected during a calibration experiment where the array is exposed to a set of sample conditions that are expected to be representative of the conditions that the array will experience during normal operation. Typically, the calibration experiment is the same one used to obtain data for constructing the quantitative, predictive model for the analyte gas(es). The data collected during such an experiment A22 can be arranged in a matrix, called S:

$$S = \begin{bmatrix} s_{1,1} & s_{1,2} & \Lambda & s_{1,J} \\ s_{2,1} & s_{2,2} & \Lambda & s_{2,J} \\ M & M & M & M \\ s_{I,1} & s_{I,2} & \Lambda & s_{I,J} \end{bmatrix} \quad (2)$$

where $s_{i,j}$ is the response of sensor element j at sample condition i. In the context of the algorithm development process (FIG. 16), S typically contains the corrected sensor and auxiliary/engine data A22, but can contain various pre-corrected forms of the calibration data (A15, A17, or A20).

Several different modeling tools could then be used to build a sensor array response model E1. Linear modeling methods are commonly used, but nonlinear methods may also be applied. One linear modeling tool is Principal Components Analysis (PCA), where the response data S is decomposed into a set of NC Principal Components (PCs) that describe most of the variation in the data:

$$S = T \cdot P + E \quad (3)$$

where T is a scores matrix of (i by NC) elements containing the "intensities" of each of the sample conditions for each PC, P is a loadings matrix of (NC by j) elements containing the "definitions" of the PCs with respect to the original j sensing elements' measurement space, and E is the residual matrix, which contains the information in S that is not explained by the PCA model. In the case of PCA, the scores and loadings matrices, T and P, constitute the Quality Factor model E2.

Once the Quality Factor model is developed, it can be applied (F1) to any subsequent array of sensor data in real time to produce various model outputs F2. In the case of a Quality Factor model developed using PCA, there are several possible outputs that can be produced from application of the model to a sensor data array. Only two of these outputs, sample residual and sample leverage, will be described here.

If a new set of sensor array data, obtained from a new sample of the sensor array responses, is denoted by the vector $s_p (= \{s_{p,1} \ s_{p,2} \ldots s_{p,J}\})$, then application of the PCA Quality Factor Model involves calculating the PCA scores of this new set of data $(t_p)$ through matrix multiplication of the PCA model loadings (P) with the new data vector $(s_p)$:

$$t_p = P \cdot s_p' \quad (4)$$

At this point, a model-estimate of the new sensor array responses $(s_{p,est})$ can be calculated:

$$s_{p,est} = t_p \cdot P \quad (5)$$

The residual of the new sample (RES) is the sum of the squares of the differences between the elements of the real sensor array response vector and the model-estimated sensor array response vector:

$$\text{RES} = (s_p - s_{p,est}) * (s_p - s_{p,est})' \quad (6)$$

This statistic describes the extent to which the PCA Quality Factor model explains the data in the new sample vector $s_p$.

The leverage of the new sample (LEV) is simply the magnitude of the new sample's scores vector $(t_p)$, where each of the NC elements in the scores vector is weighted by the amount of information that is explained by that principal component:

$$LEV = (1/i) + t_p' \cdot (T' \cdot T)^{-1} \cdot t_p \quad (7)$$

where I is the number of samples used to develop the model. This statistic describes how extreme the new sample is within the PCA model's space, once it is applied to the PCA model.

Once the model outputs F2 (e.g., residual and leverage) of the new sample are obtained, there are many ways in which they can be combined to provide a single Quality Factor F4. For example, each of these statistics can be divided by a reference value of these statistics, $RES_{ref}$ and $LEV_{ref}$, for the calibration data set, to obtain a residual ratio (RR) and leverage ratio (LR):

$$RR = RES/[trace((S - T \cdot P) \cdot (S - T \cdot P)')/i] = RES/RES_{ref} \quad (8)$$

$$LR = LEV/(1 + NC/i) = LEV/LEV_{ref} \quad (9)$$

A value of RR or LR much greater than one indicates that the pattern of the new sample data vector does not closely match any of the data patterns observed during the calibration experiment. Therefore, the new data might produce erroneous results if applied to a quantitative gas concentration prediction algorithm that was developed using the calibration data. The reference values may be the average residual and leverage obtained during model calibration.

$$RES_{ref} = RES_{avg} \quad (10)$$

$$LEV_{ref} = LEV_{avg} \quad (11)$$

or other statistically-determined values related to a specific confidence limit for the parameters (e.g., 95% confidence limit) known to the art:

$$REF_{ref} = RES_{95\%} \quad (12)$$

$$LEV_{ref} = LEV_{95\%} \quad (13)$$

The RR and LR can be combined into a single Quality Factor in many different ways, depending on the application and how they are to be used. For example, the Quality Factor can simply be the sum of the RR and LR, a weighted sum of the RR and LR, or the sum of the RR and LR minus the product of the fractional parts of the RR and LR.

For a sensor device application, where there might not be a large amount of available resources on the data processing hardware to store model information and to enable processing of large data arrays, it is critical to compress the Quality Factor model E2 into a form that uses a minimal amount of data storage space, and leads to a minimum of online data processing steps. In the case of a Quality Factor model built using PCA, the complete model contains a total of $(i \cdot NC) + (j \cdot NC)$ parameters, coming from the (i by NC) scores matrix T and the (NC by j) loadings matrix P. Although the complete loadings matrix P is required to enable online application of the model (Equation 4), the complete scores matrix T is not needed for the online application as described above. The scores matrix can be compressed into a sum-of-squares score vector $t^2$, which contains the sum of the squares of the scores for each of the NC principal components:

$$t^2 = \text{diagonal elements of } (T' \cdot T) \quad (10)$$

This reduced representation of the model scores still enable on-line calculation of sample leverage via a modified form of Equation 7:

$$LEV = (1/i) + t_p' \cdot (\text{diag}(t^2))^{-1} \cdot t_p \quad (11)$$

The vector $t^2$ contains only NC parameters, where the T matrix contains $NC \cdot i$ parameters. In a typical case where a calibration data set might have 1000 observations (i=1000) and the number of principal components is 4, the number of parameters that must be stored drops from 4000 to 4.

In addition, the reference sample residual of the calibration data ($RES_{ref}$), used to calculate the RR (Equation 8) will not change once the model is developed. Therefore, it can be calculated and stored with the other compressed model parameters on the device data processing hardware, and applied as in Equation 8. This scheme greatly reduces the complexity of the on-line data processing needed in order to calculate the RR for each new sample array.

(4) Variants on the Quality Factor

Variations of the Quality Factor described above may also be used. For example, a response modeling method other than PCA may be used to generate the Quality Factor model, such a Linear Discriminant Analysis (LDA). A weighted Quality Factor model may be built where the sensor array inputs are each weighted by the magnitude of their regression coefficient for the quantitative gas concentration prediction algorithm, or according to prior knowledge of their importance in the quantitative algorithm. Different mathematical operations on the model outputs F2 may be used to calculate the Quality Factor. Several Quality Factor models may be used for a single sensor device, wherein each one is designed to monitor for different types of outlier conditions.

(5) Uses of the Quality Factor (a) Rejection of Dangerous Predictions

Figure 30:
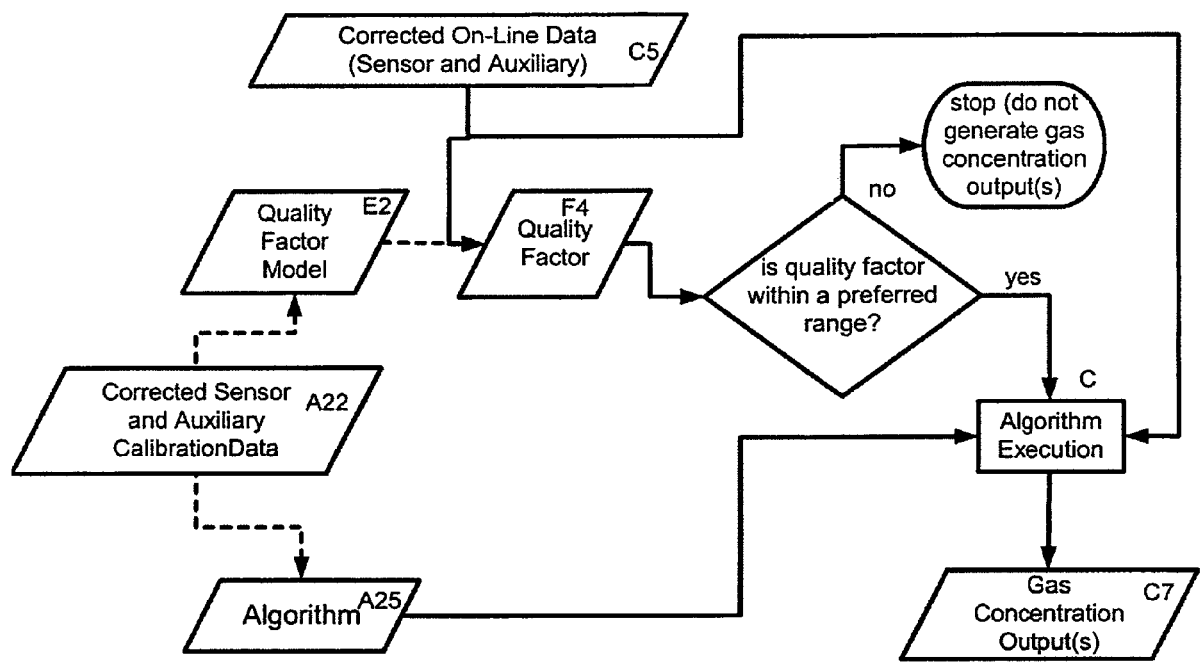
FIG. 30 is a flow chart showing the use of the quality factor for the rejection of dangerous gas concentration predictions from the sensor device.

The Quality Factor can be used to assess whether a gas concentration output C7 from a quantitative algorithm A25 is suspect, due to the current on-line sensor array responses not being within the range of sensor array responses observed in the calibration data used for quantitative algorithm development. FIG. 30 illustrates this use of the Quality Factor. In this case, it is important that the calibration data A22 used to build the Quality Factor Model is identical to the data used to build the quantitative algorithm. If the Quality Factor obtained on-line F4 indicates an outlier condition, then an instruction can be sent to the data processor to avoid executing the quantitative algorithm and reporting a gas concentration. Several criteria can be used to determine the range of quality factor values that reveal an outlier condition. For example, in the case of a PCA Quality Factor model, a 95% confidence limit on the RR or LRs obtained using the calibration data can be determined, and an alarm set for any on-line data that generates an RR or LR outside of these limits.

Figure 30A:
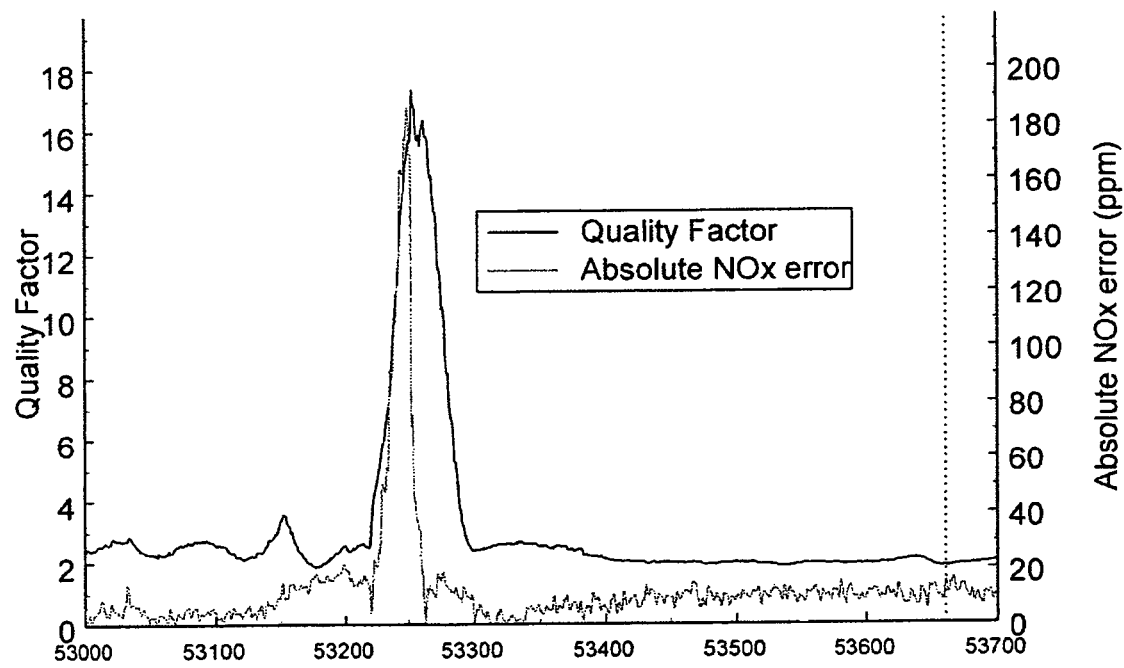
FIG. 30A is a graph showing the quality factor and absolute $NO_x$ error.

An example of the utility of the Quality Factor for detecting dangerous predictions is illustrated in FIG. 30A. In this case, a quantitative algorithm for predicting $NO_x$ concentration was developed using eight different sensing elements. The quality factor model was built using the exact same data obtained from the eight sensing elements, using the PCA modeling method. FIG. 30A displays two curves: one that shows the absolute difference between the $NO_x$ concentration predicted by the quantitative model and the known concentration, and one that shows the value of the quality factor during the same period of time. In this case, the Quality Factor is defined as the sum of the residual ratio (RR) and leverage ratio (LR) obtained for each data point. Note that the Quality Factor increases at precisely the same time as the $NO_x$ prediction error increases. In a real application, one does not have the benefit of knowing the actual $NO_x$ prediction error. As a result, this example indicates that the Quality Factor can provide a very useful alarm for dangerous quantitative predictions during a real-time engine application. In this specific example, a threshold in the Quality Factor can be defined such that all data points with a Quality Factor above this threshold will result in an alarm, and not generate a $NO_x$ concentration output.

(b) Calculating Tolerance Limits on Predicted Concentrations

Figure 31:
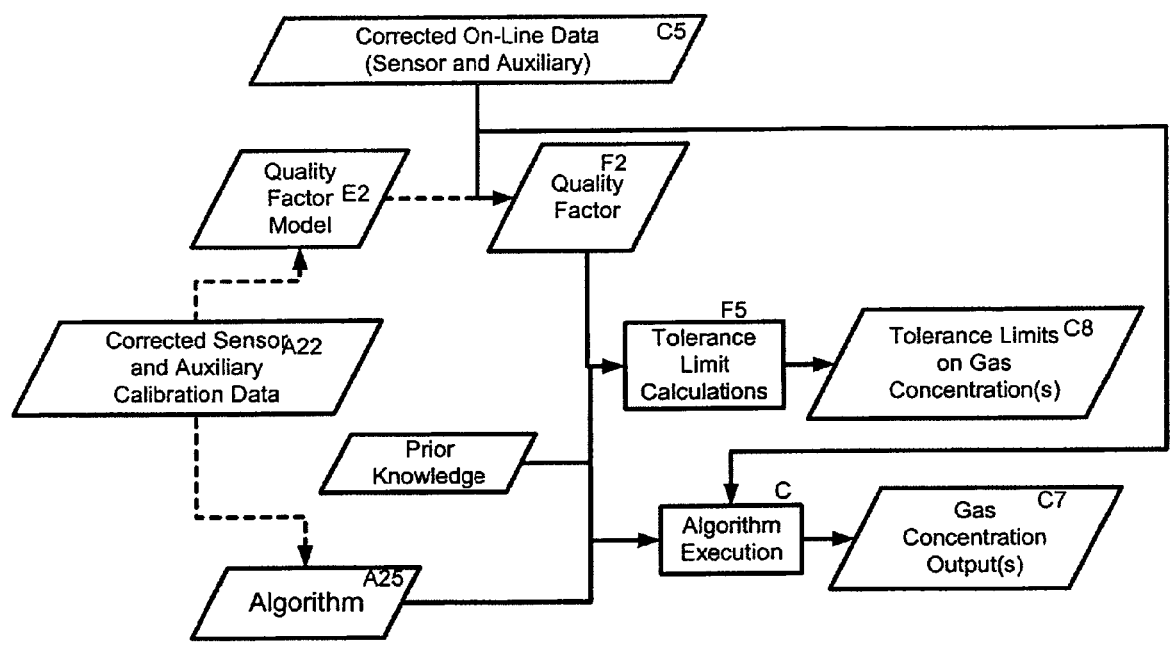
FIG. 31 is a flow chart showing the use of the quality factor for the calculation of tolerance limits on the predicted concentration(s) from the sensor device.

Because the Quality Factor provides a continuous measure of the extent to which a sensor response is in an outlier condition, and this extent influences the error in the gas concentration output C7 from the quantitative model, the Quality Factor can be used to calculate tolerance limits on the gas concentration output. FIG. 31 illustrates this use of the Quality Factor. In this case, it is important that the calibration data A22 used to build the Quality Factor Model is identical to the data used to build the quantitative algorithm. The Quality Factor can be used along with data from the quantitative algorithm A25, the calibration data used to build the algorithm A22, or other prior knowledge to calculate a tolerance limit. For example, if the noise in the analyzer calibration data used to build the algorithm is known, then a tolerance limit could be calculated as this noise value multiplied by a scaled value of the Quality Factor.

(c) Calculating a Composite Predicted Concentration from Several Algorithms

Figure 32:
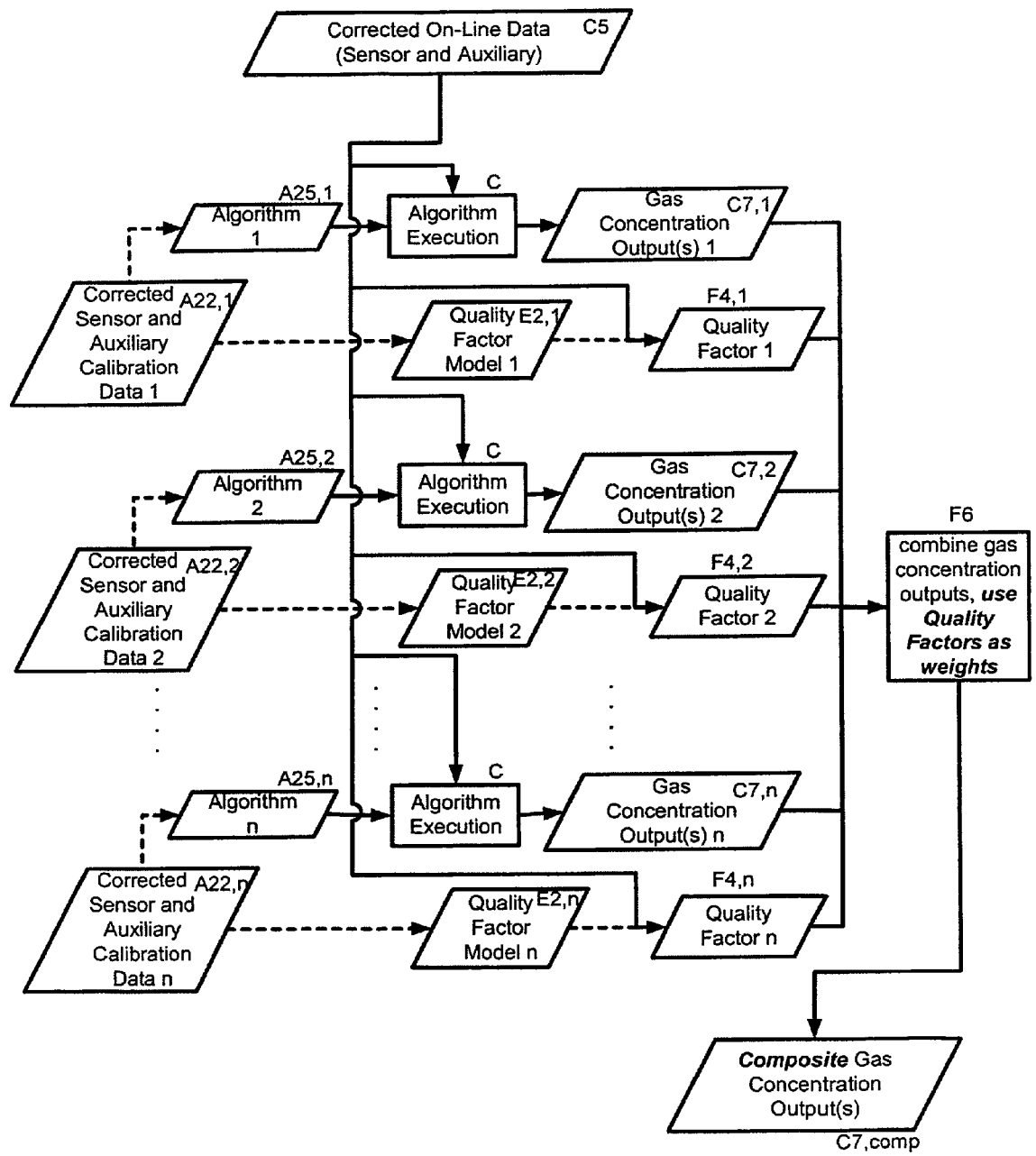
FIG. 32 is a flow chart showing the use of the quality factor for the calculation of a composite predicted gas concentration from more than one algorithm.

If several different quantitative algorithms A25 are developed, Quality Factors corresponding to each of these algorithms can be used along with their quantitative gas concentration predictions to provide a composite prediction value of the gas concentration. FIG. 32 illustrates this use of the Quality Factor. For this application, it is important that, for each quantitative algorithm, the calibration data A22 used to build the Quality Factor Model is identical to the data used to build the algorithm. In this application, the composite gas concentration C7,comp could be a weighted average of the concentrations obtained from the different quantitative algorithms, where the weight for each algorithm is proportional to the algorithm's corresponding Quality Factor. If the Quality Factor increases with improved prediction of the quantitative algorithm, then the weights could be directly proportional to the Quality Factors. If the Quality Factor decreases with improved prediction of the quantitative algorithm, then the weights could be inversely proportional to the Quality Factors.

(d) Triggering a Corrective Action

Figure 33:
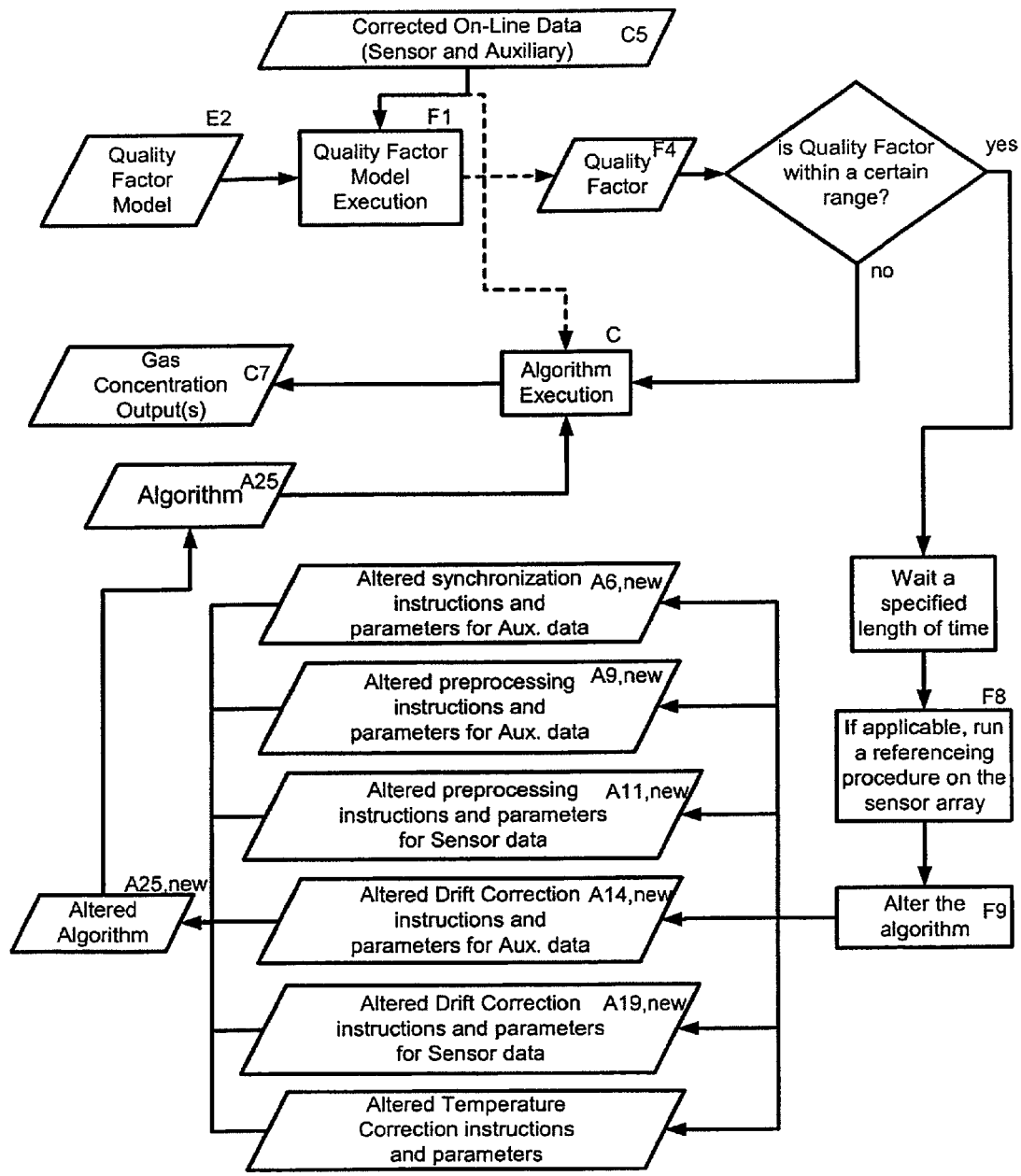
FIG. 33 is a flow chart showing the use of the quality factor to trigger corrective action on the sensor device itself and/or on the algorithm used to predict gas concentrations.

Specialized Quality Factor models can be developed that are sensitive to specific failure mode conditions for the sensor device and algorithm. As a result, the Quality Factor can be used to detect such failure modes during real-time operation. FIG. 33 illustrates this use of the Quality Factor. In this application, it is not necessary that the calibration data A22 used to build the Quality Factor Model be identical to the data used to build the quantitative algorithm, just that the model be developed so that it is sensitive to a specific condition. When the Quality Factor lies within a certain pre-determined range, a corrective action is triggered after a pre-determined delay time. This corrective action might involve a physical procedure on the sensor device itself, an alteration of the algorithm(s) being used on the device, or both.

This use of the Quality Factor is particularly helpful in situations where gradual drift of the sensor responses causes quantitative prediction performance to steadily degrade over time. Such degradation could originate from several sources, such as aging of the sensor or gradual fouling of the sensor surfaces over time. In such cases, there are several examples of corrective actions that can be triggered by the Quality Factor. In one example, the Quality Factor can be used to trigger a referencing procedure on the sensor device, in which the temperature of the array is temporarily increased, the lambda signal is measured, and the scaling (preprocessing) parameters for the sensor data are adjusted. In another example, the Quality Factor can be used to determine the optimal time for updating the drift correction factors used in the Cycle-Wise Drift Correction method, or other drift correction method.

Figure 33A:
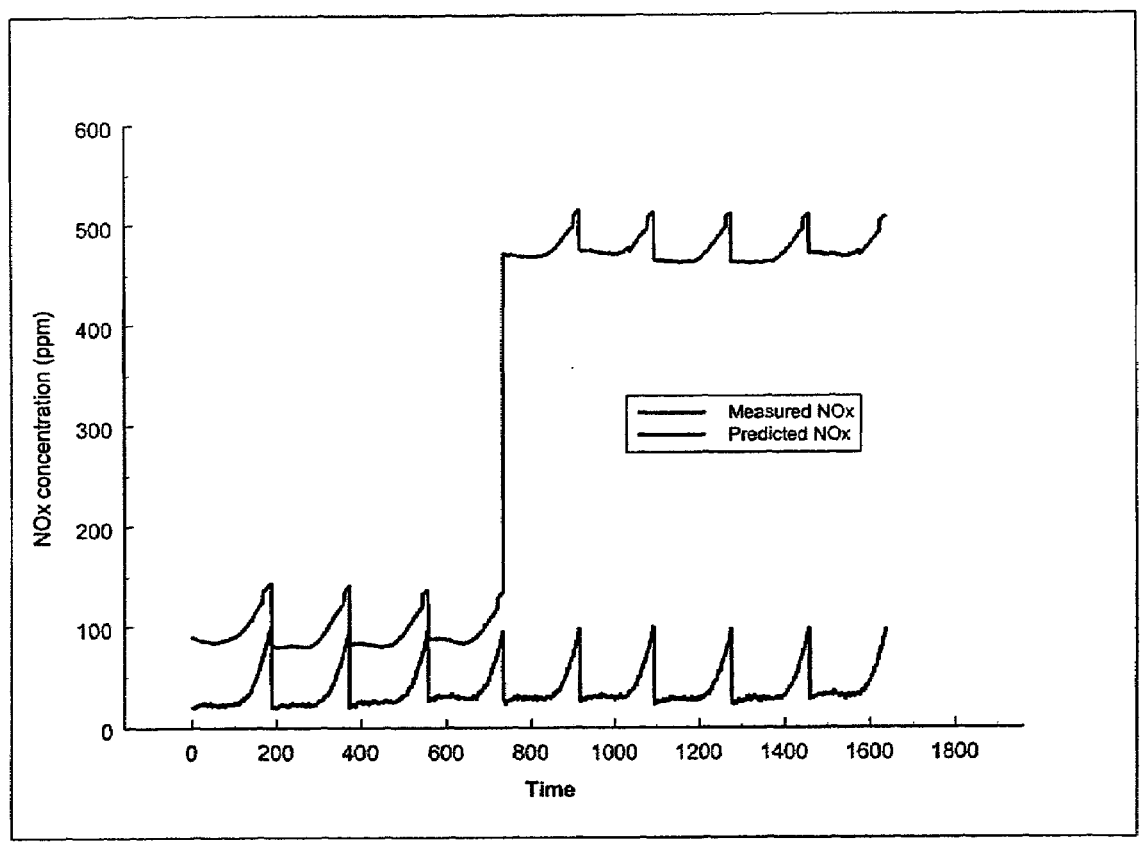
FIG. 33A shows the departure of the $NO_x$ concentration precidtion of one sensor in an array compared to those of the other sensors in the array.
Figure 33B:
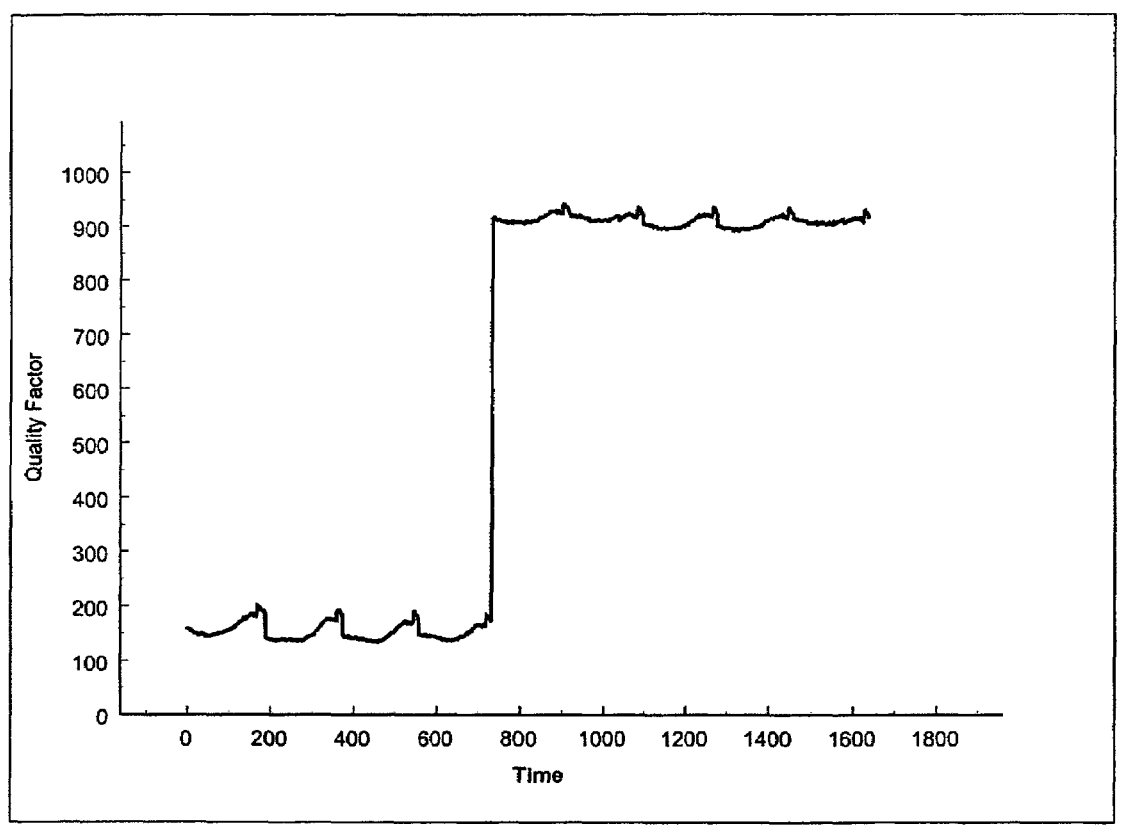
FIG. 33B shows a change in the $NO_x$ concentration prediction of a sensor as processed by Quality Factor model.

Specific Quality Factor models can also be developed to detect other failure modes in the sensor device, such as the failure of a sensor heater, failure of an electrical lead, or the failure of one or more of the sensing elements. In these cases, the Quality Factor can be used to trigger an alarm on the sensor, modification of the existing algorithm, or the selection of a new algorithm that does not rely upon the failed sensing element(s). In one specific example (FIGS. 33A and 33B), the Quality Factor is used to detect the failure of one of 12 sensing elements in the sensor array. The failure of one of the sensor elements at time point 735 corresponds to a large bias in the predicted $NO_x$ concentration (FIG. 33A). The Quality Factor model used in this example was a PCA model of sensor element responses that were not corrected for baseline offset or drift, and the Quality Factor was defined as the sum of the Residual Ratio (RR) and the Leverage Ratio (LR). As a result, the Quality Factor was sensitive to large absolute changes in the responses of any of the sensing elements, and it clearly detects the failure of the sensing element in the form of a large increase (see FIG. 33B).

(e) Facilitating Real-Time Algorithm Selection

Figure 34:
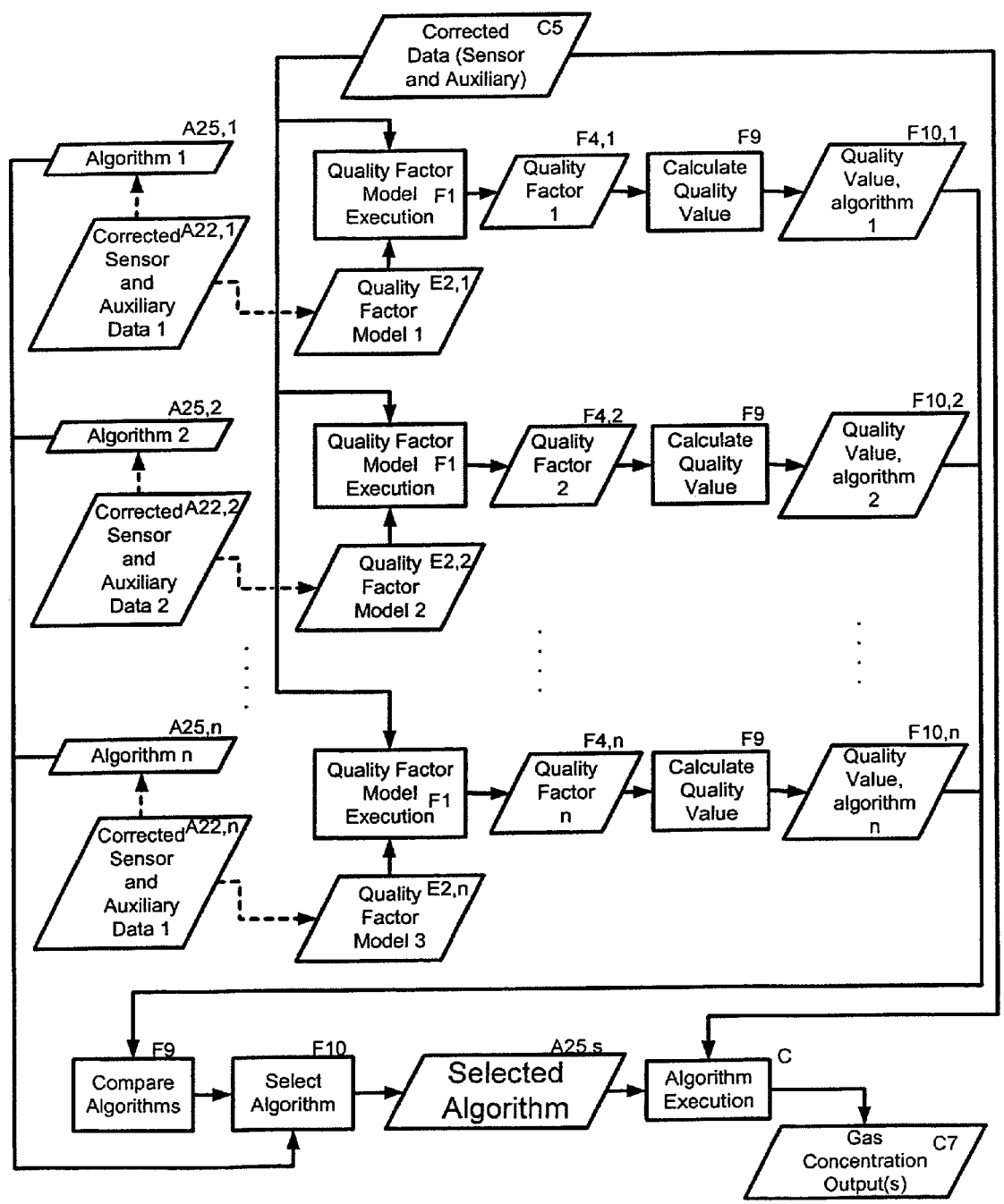
FIG. 34 is a flow chart showing the use of the quality factor to facilitate real-time algorithm selection.

If several different quantitative algorithms A25 are developed, real-time Quality Factors corresponding to each of these algorithms can be used to select the most appropriate quantitative algorithm. FIG. 34 illustrates this use of the Quality Factor. For this application, it is important that, for each quantitative algorithm, the calibration data A22 used to build the Quality Factor Model is identical to the data used to build the algorithm. During real-time operation, the different quality factors F4 corresponding to the different quantitative algorithms A25 are generated, using the different quality factor models and the current on-line data C5. Then, these quality factors are compared in order to select the most appropriate algorithm to apply to the current data C5. For example, the algorithm whose corresponding quality factor indicates the least severe outlier condition can be selected at each time during real-time operation.

Figure 34A:
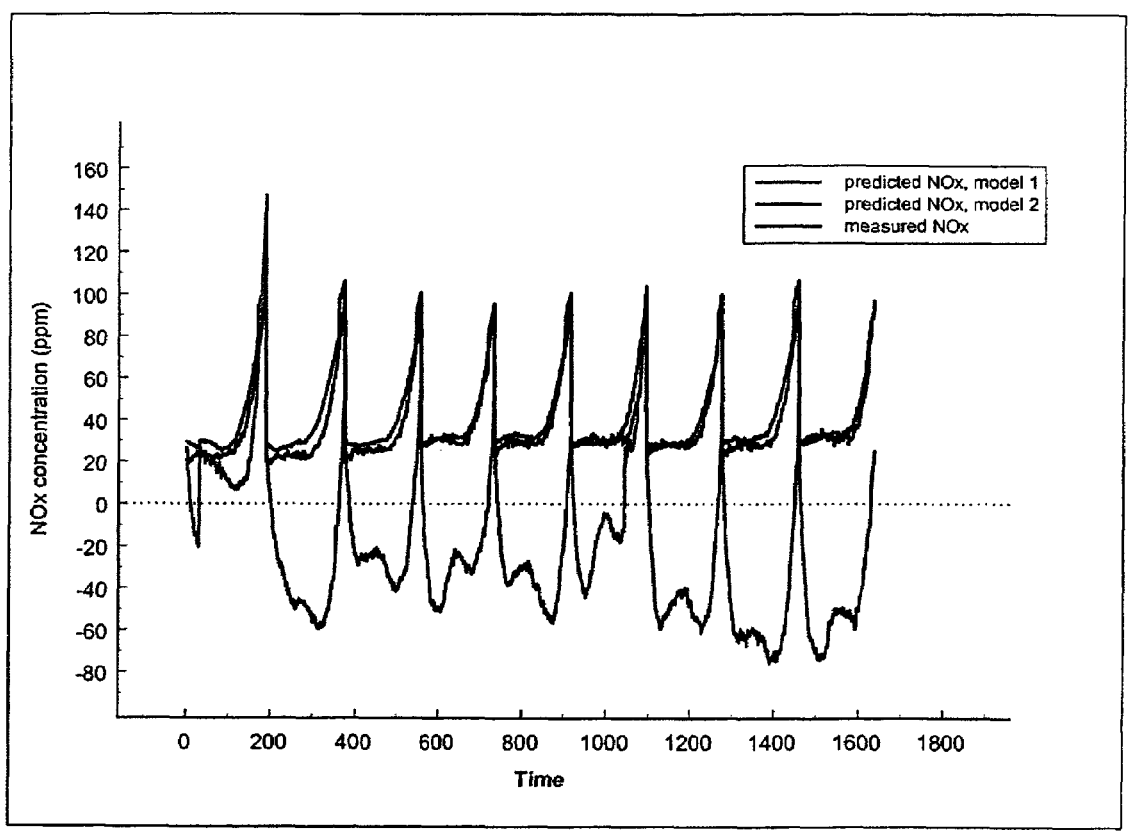
FIG. 34A shows the relative performance of two different algorithm in the determination of $NO_x$ concentration as compared to measured, actual results.
Figure 34B:
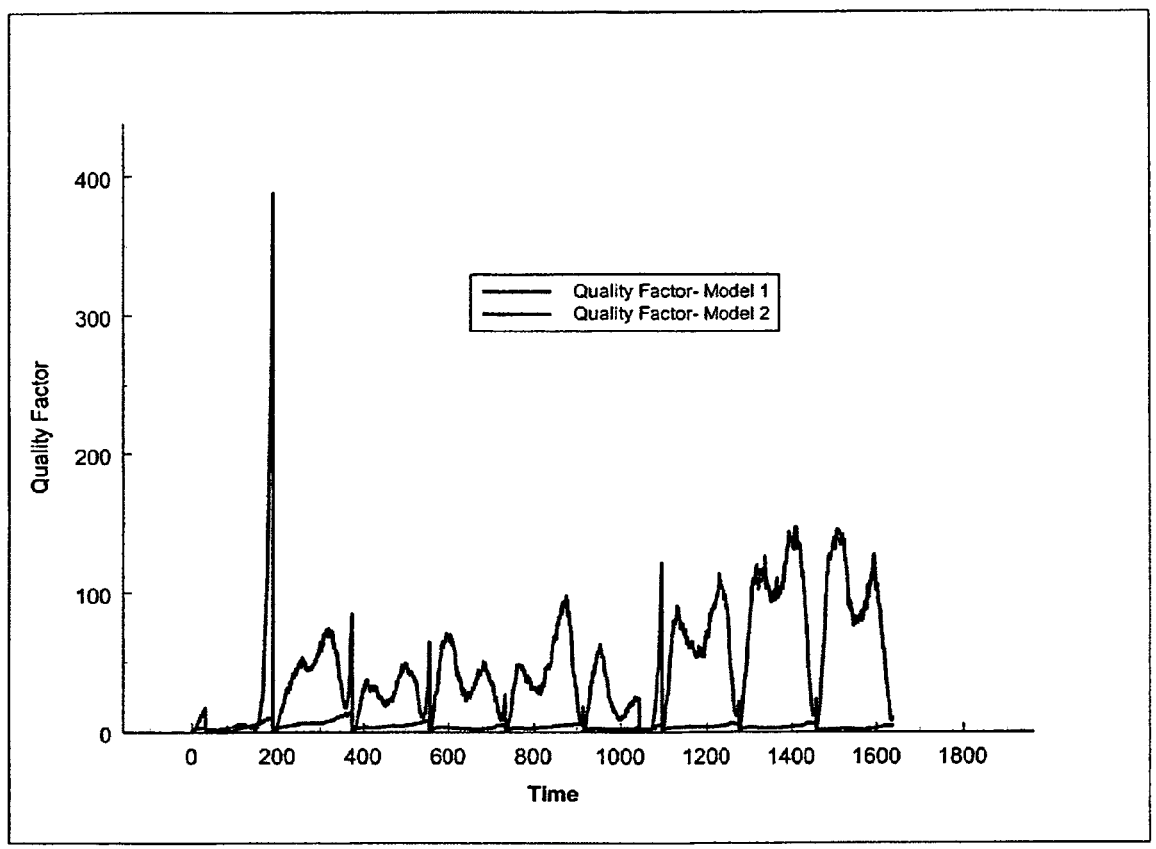
FIG. 34B shows the relative performance of two different Quality Factor models in the determination of $NO_x$ concentration.
Figure 35:
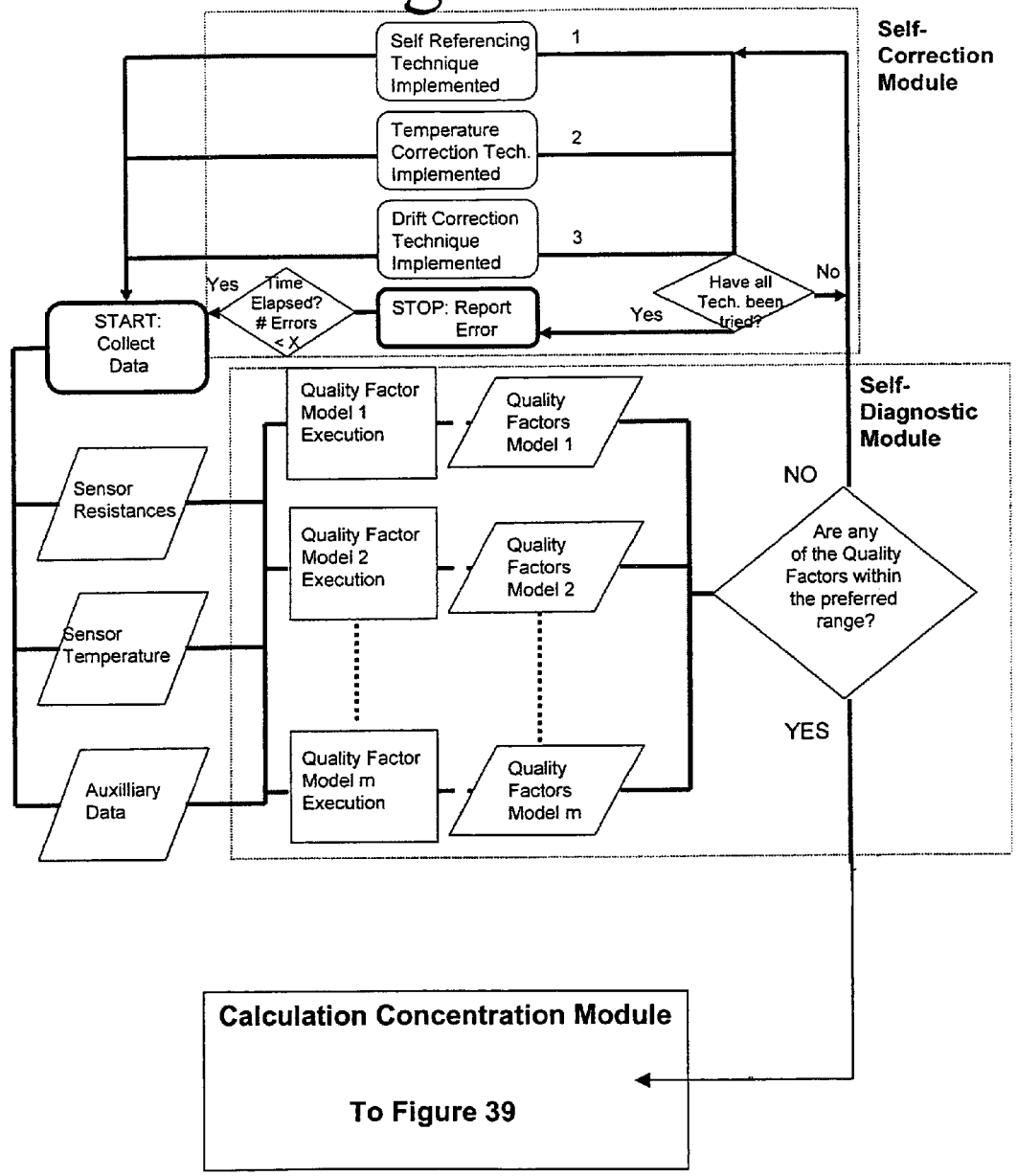
FIG. 35 is a flow chart showing the overall scheme of the functioning real-time algorithm.
Figure 36:
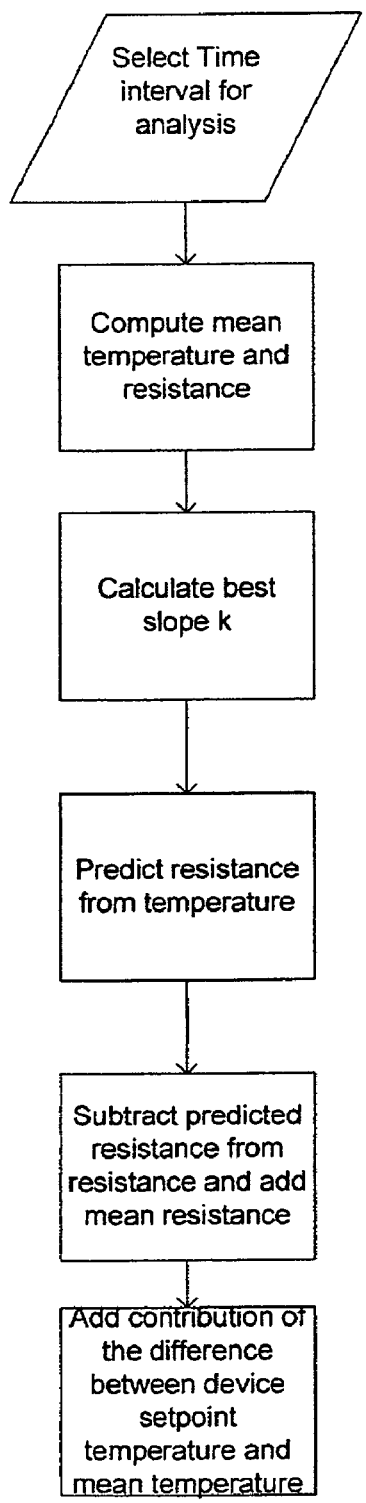
FIG. 36 is a flow chart showing the temperature correction technique using a predetermined, time invariant relationship between temperature and resistance.
Figure 37:
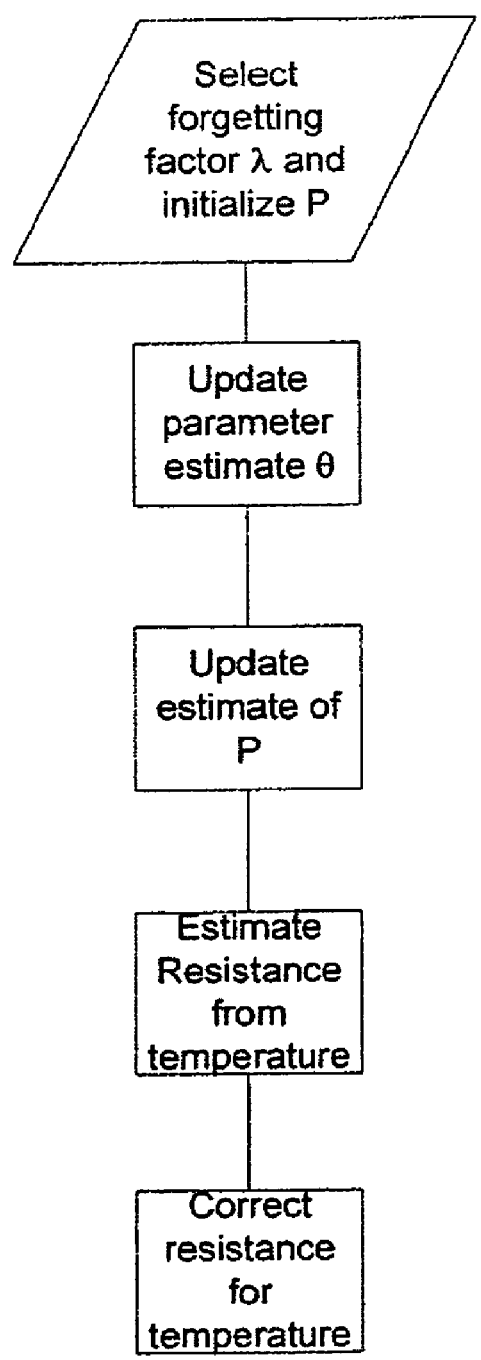
FIG. 37 is a flow chart showing the temperature correction technique using an adaptively computed time-varying relationship between temperature and resistance.
Figure 38A:
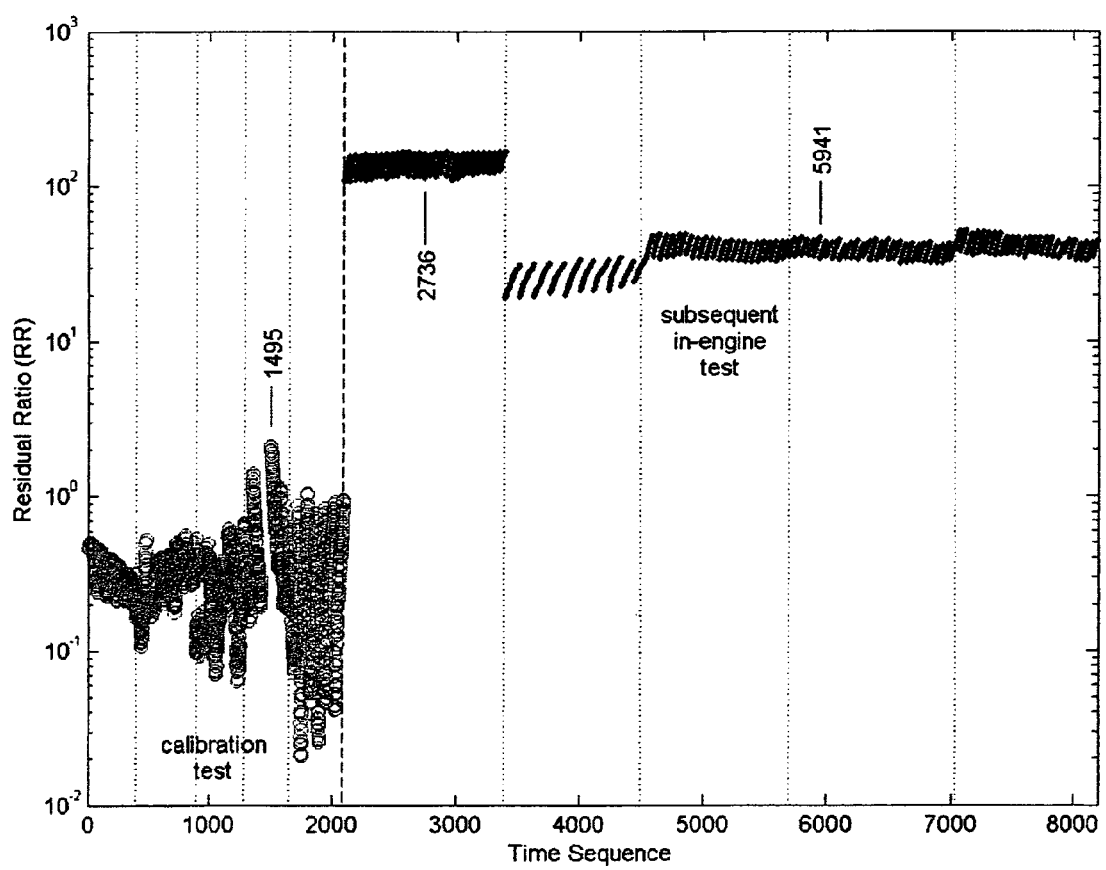
Figure 38B:
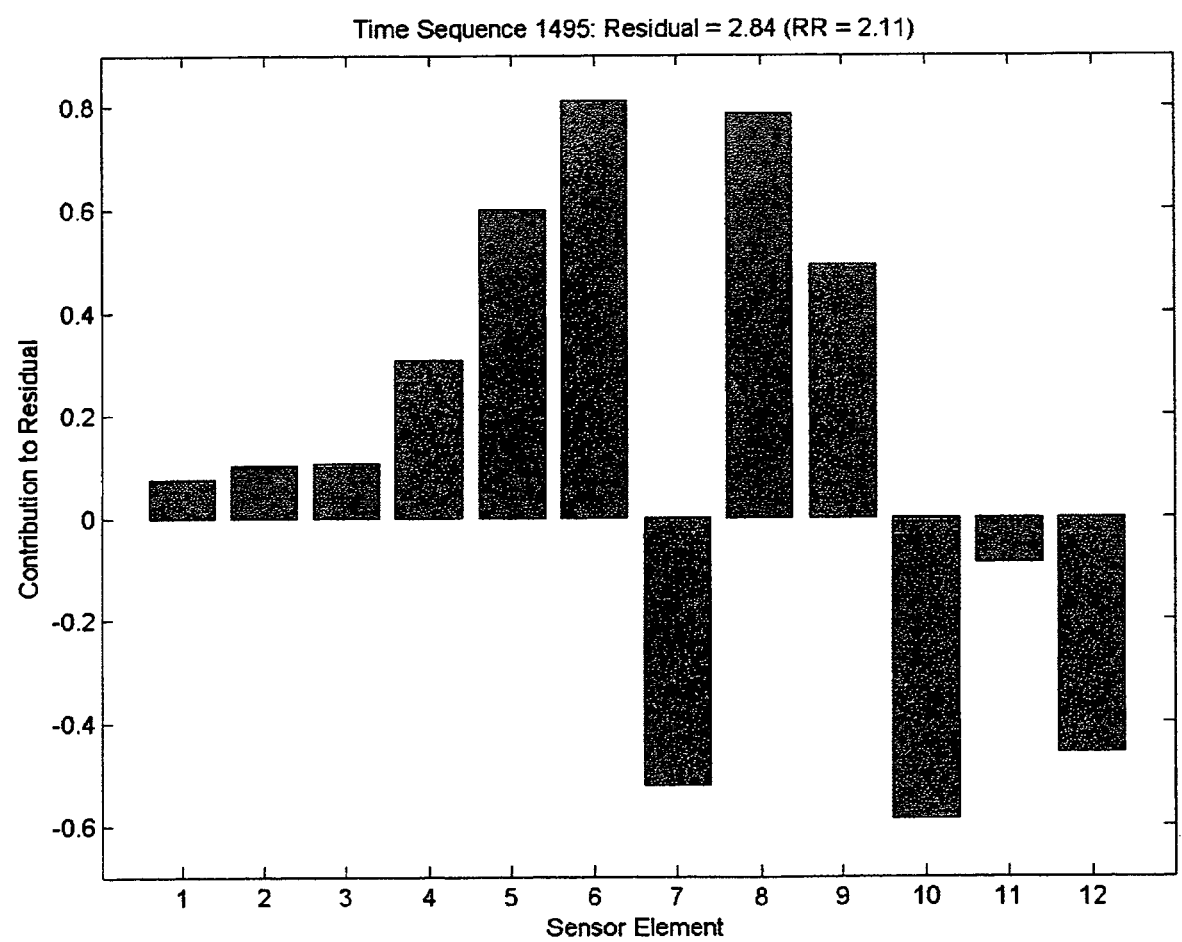
Figure 38C:
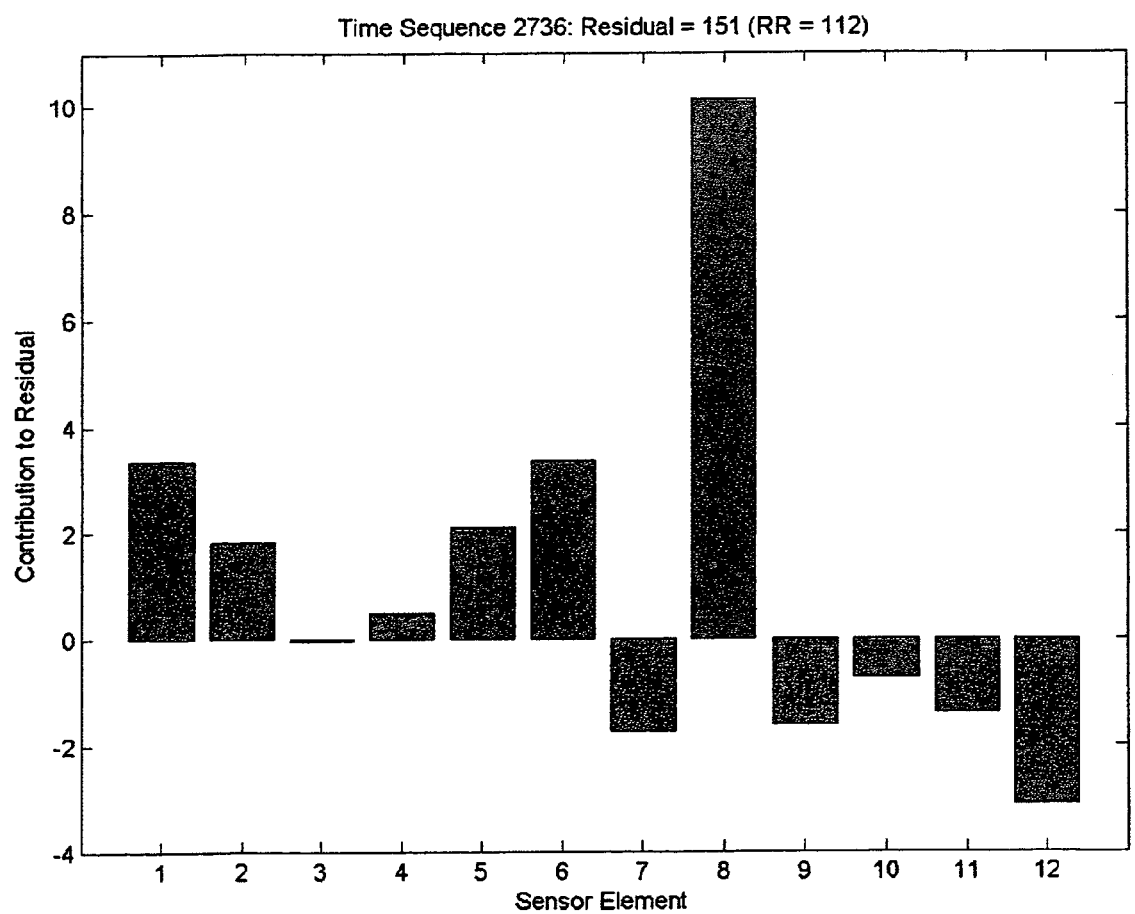
Figure 38D:
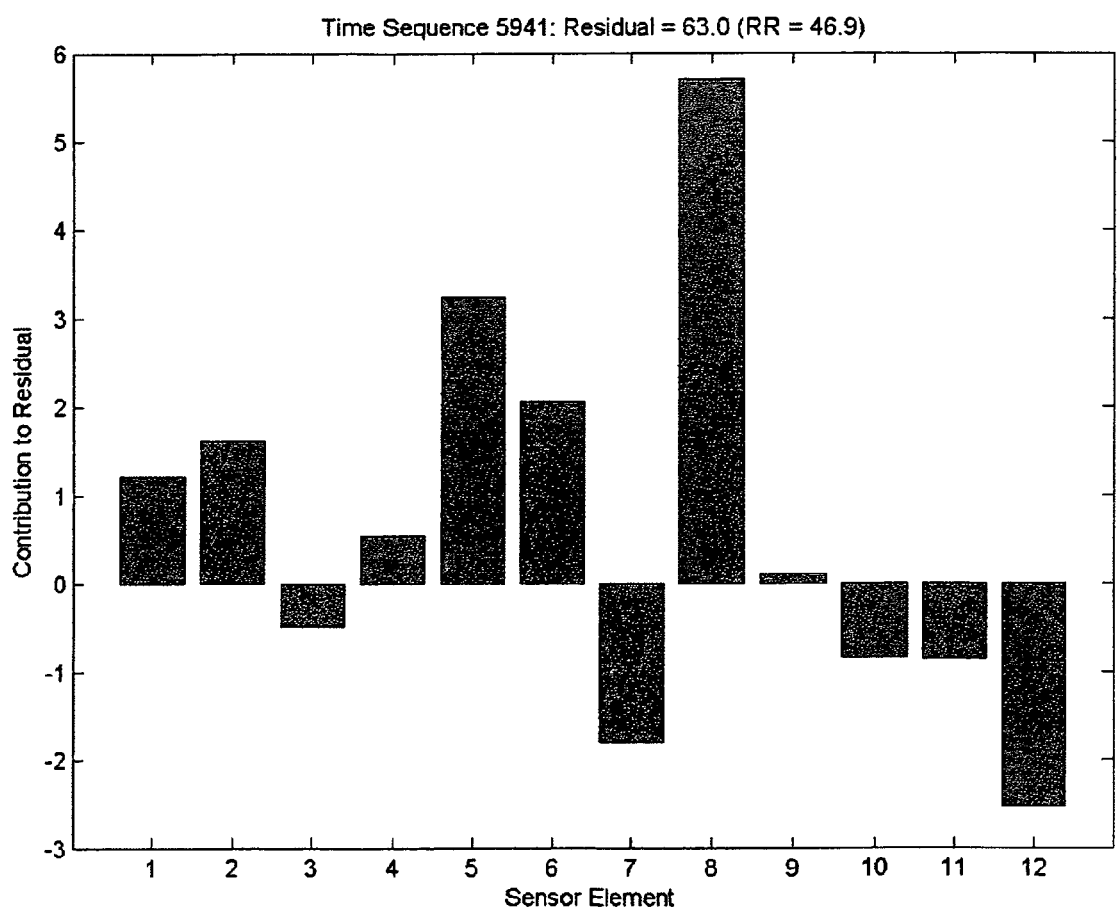
Figure 38E:
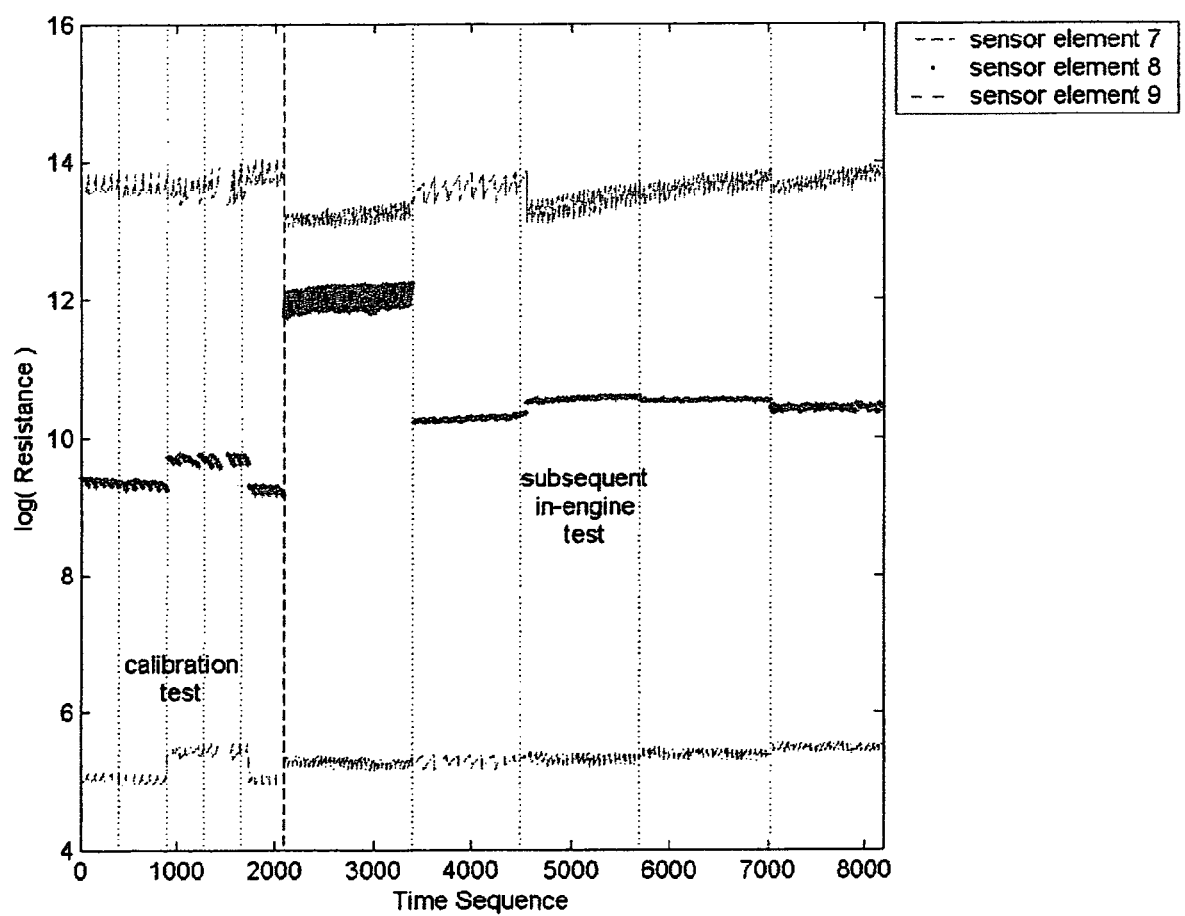
Figure 39:
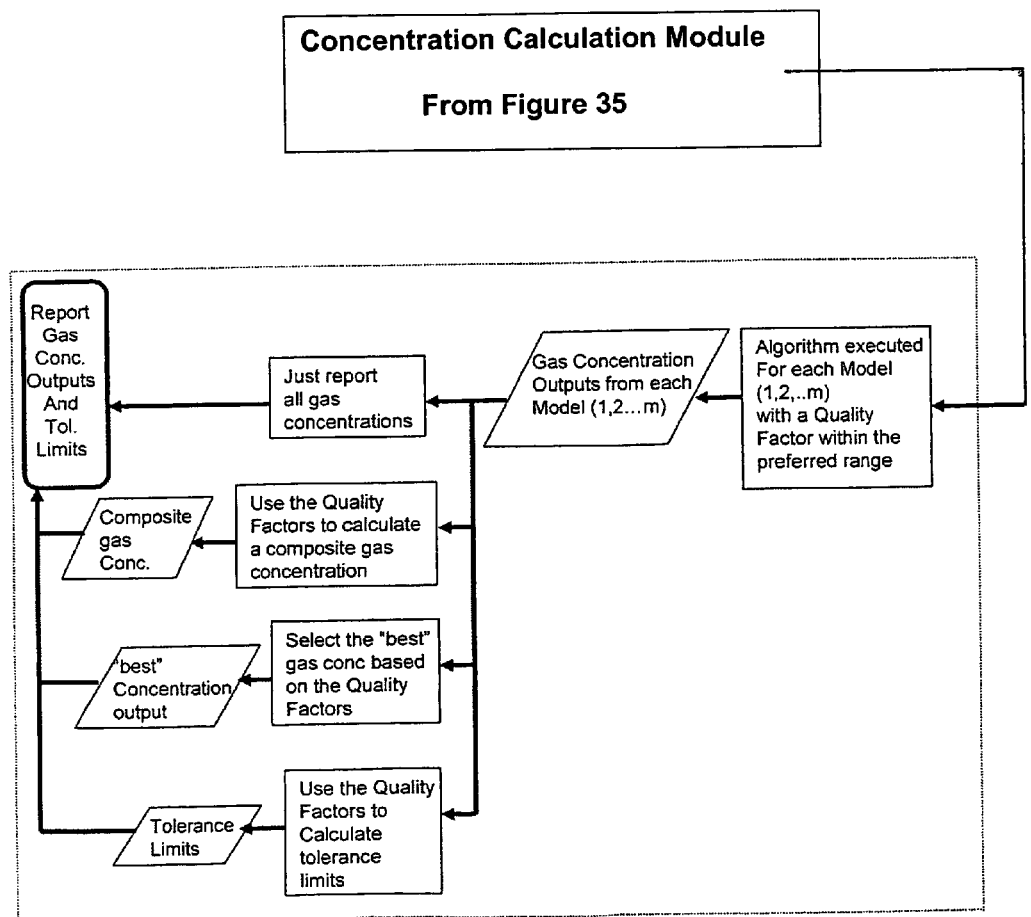
FIG. 39 is a flow chart showing the concentration calculation module of the algorithm.

FIGS. 34A and 34B illustrate how algorithm-specific Quality Factors can be used to enable real-time algorithm selection. In this example, two different algorithms were developed, and each of them has an associated Quality Factor model that was built using the identical calibration data. Although both algorithms have similar calibration model fits, one clearly performs better than the other when applied on-line (FIG. 34A). The Quality Factors corresponding to each of these algorithms are shown in FIG. 34B, where the Quality Factors in each case are defined as the sum of the Residual Ratio (RR) and Leverage Ratio (LR). It is clear that algorithm 1's Quality Factor is always less than algorithm 2's, which suggests that Algorithm 1 is the most appropriate one to use for the current data. This is confirmed by the $NO_x$ prediction results in FIG. 34A.

It will be apparent to those skilled in the art that various modifications and variations can be made in the computer-implemented system and method for sensing and analyzing certain gases, including $NO_x$, hydrocarbons, carbon monoxide and oxygen in a multi-component gas system using chemical sensors and chemical sensor arrays of the present invention and in construction of this system and method without departing from the scope or spirit of the invention. Examples of which have been previously provided.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for converting the responses of an array of metal oxide sensors into constituents and concentrations of a multi-component gas provided around the sensor array, the method comprising:
   providing a self-diagnostic module to calculate quality factors associated with corresponding prediction models, and to determine if the responses of the sensor array are within a preferred range;
   providing a self-correction module to compensate for changes in the responses over time so that quality factors can be obtained which are within the preferred limits, or to stop the responses and report an error; and
   providing a concentration calculation module to calculate the gas concentration outputs from each prediction model, corresponding tolerance limits, and gas concentration outputs determined by weighting the outputs from the prediction models by corresponding quality factors and determining weighted tolerance limits, so that the gas concentration outputs with the lowest tolerance limits can be reported as the actual constituents and concentrations of the multi-component gas.

2. A method as recited in claim 1, wherein the self-diagnostic module performs one of a linear transformation or a nonlinear transformation on one of the sensor responses, sensor temperature values, or any values of any auxiliary sensor data.

3. A method as recited in claim 2, wherein the self-diagnostic module performs a real-time quality factor calculation for the sensor array.

4. A method as recited in claim 3, wherein the real-time quality factor calculation utilizes a Principal Component Analysis model of one of transformed sensor responses, sensor temperature values, or auxiliary data obtained during calibration experiments.

5. A method as recited in claim 4, wherein the Principal Component Analysis model is compressed by reducing the model scores matrix to a sum of squares scores vector, thus reducing the number of model parameters that must be stored.

6. A method as recited in claim 3, wherein the real-time quality factor calculation evaluates one of the sensor responses, sensor temperature values, or auxiliary data obtained during calibration experiments to determine whether the sensor array is operating within predetermined limits.

7. A method as recited in claim 3, wherein the real-time quality factor calculation determines the pattern of one of the sensor responses, sensor temperature values, or auxiliary data obtained during calibration experiments.

8. A method as recited in claim 3, wherein the real-time quality factor calculation determines the covariance of one of the sensor responses, sensor temperature values, or auxiliary data obtained during calibration experiments.

9. A method as recited in claim 3, wherein the real-time quality factor calculation determines that the sensor array is not operating within the preferred range for any of the prediction models and that the self-correction module must be used.

10. A method as recited in claim 3, wherein the real-time quality factor calculation determines that the sensor array is operating within the preferred range for one or more of the prediction models and outputs from all prediction models are transferred to the concentration calculation module.

11. A method as recited in claim 3, wherein the concentration calculation module calculates the gas concentration outputs and tolerance limits weighted by the real-time quality factor calculation.

12. A method as recited in claim 1, wherein the concentration calculation module calculates the gas concentration outputs and tolerance limits for each prediction model.

13. A method as recited in claim 12, wherein the gas concentration outputs and tolerance limits for each prediction model are calculated using at least one of a Projection to Latent Structures (PLS) model or another linear model.

14. A method as recited in claim 12, wherein the gas concentration outputs and tolerance limits for each prediction model are calculated using at least one of a neural network model or another nonlinear model.

15. A method as recited in claim 12, wherein the gas concentration outputs and tolerance limits for each prediction model are calculated using at least one of a Projection to Latent Structures (PLS) model, a neural network model, or other linear and nonlinear models.

16. A method as recited in claim 1, wherein the self-correction module provides a temperature correction process for the sensor array in real-time.

17. A method as recited in claim 16, wherein the temperature correction process comprises removing variations in the sensor responses due to temperature using a fixed relationship between temperature and resistance.

18. A method as recited in claim 16, wherein the temperature correction process comprises removing variations in the sensor responses due to temperature using a recursive algorithm to provide a time-varying relationship between temperature and resistance.

19. A method as recited in claim 1, wherein the self-correction module provides a self-referencing process for the sensor array in real-time.

20. A method as recited in claim 19, wherein the self-referencing process comprises increasing the temperature of the sensor array, measuring the air/fuel ratio around the sensor array, and scaling the sensor responses to responses at a predetermined reference state.

21. A method as recited in claim 1, wherein the self-correction module provides a drift correction process for the sensor array in real-time.

22. A method as recited in claim 21, wherein the drift correction process comprises adjusting the sensor responses for both offset and span, and determining the offset and span correction factors at any given time using real-time sensor responses, sensor temperature, and available auxiliary engine data.

23. A method as recited in claim 1, wherein the self-correction module determines that the self-correction module cannot compensate for the changes in the sensor responses, stops the sensor array from processing data for a predetermined time, reports an error to the sensor array, and begins processing data again after the predetermined time.

24. A method as recited in claim 1, wherein the self-correction module determines that the self-correction module cannot compensate for the changes in the sensor responses, stops the sensor array from processing data for a predetermined time, reports an error to the sensor array, and does not begin processing data again if the number of sequential errors is greater than a predetermined number.

25. A method as recited in claim 1, wherein the concentration calculation module determines the most accurate gas concentration outputs using the tolerance limits.

26. A method for converting the responses of an array of metal oxide sensors into constituents and concentrations of a multi-component gas provided around the sensor array, the method comprising:

providing a self-diagnostic module to calculate quality factors associated with corresponding prediction models, and to determine if the responses of the sensor array are within a preferred range; and providing a concentration calculation module to calculate the gas concentration outputs from each prediction model, corresponding tolerance limits, and gas concentration outputs determined by weighting the outputs from the prediction models by corresponding quality factors and determining weighted tolerance limits, so that the gas concentration outputs with the lowest tolerance limits can be reported as the actual constituents and concentrations of the multi-component gas.

27. A method as recited in claim 26, further comprising a step of providing a self-correction module to compensate for changes in the responses over time so that quality factors can be obtained which are within the preferred limits or to stop the responses and report an error.

28. A method as recited in claim 27, wherein the self-correction module provides a temperature correction process for the sensor array in real-time.

29. A method as recited in claim 28, wherein the temperature correction process comprises removing variations in the sensor responses due to temperature using a fixed relationship between temperature and resistance.

30. A method as recited in claim 28, wherein the temperature correction process comprises removing variations in the sensor responses due to temperature using a recursive algorithm to provide a time-varying relationship between temperature and resistance.

31. A method as recited in claim 27, wherein the self-correction module provides a self-referencing process for the sensor array in real-time.

32. A method as recited in claim 31, wherein the self-referencing process comprises increasing the temperature of the sensor array, measuring the air/fuel ratio around the sensor array, and scaling the sensor responses to responses at a predetermined reference state.

33. A method as recited in claim 27, wherein the self-correction module provides a drift correction process for the sensor array in real-time.

34. A method as recited in claim 33, wherein the drift correction process comprises adjusting the sensor responses for both offset and span, and determining the offset and span correction factors at any given time using real-time sensor responses, sensor temperature, and available auxiliary engine data.

35. A method as recited in claim 27, wherein the self-correction module determines that the self-correction module cannot compensate for the changes in the sensor responses, stops the sensor array from processing data for a predetermined time, reports an error to the sensor array, and begins processing data again after the predetermined time.

36. A method as recited in claim 27, wherein the self-correction module determines that the self-correction module cannot compensate for the changes in the sensor responses, stops the sensor array from processing data for a predetermined time, reports an error to the sensor array, and does not begin processing data again if the number of sequential errors is greater than a predetermined number.

\* \* \* \* \*